US007618936B2

(12) United States Patent
You et al.

(10) Patent No.: US 7,618,936 B2
(45) Date of Patent: Nov. 17, 2009

(54) METHODS FOR TREATING AND DIAGNOSING CANCER WITH WNT INHIBITORY FACTOR-1 (WIF-1)

(75) Inventors: Liang You, San Francisco, CA (US); Biao He, South San Francisco, CA (US); Zhidong Xu, San Francisco, CA (US); David M. Jablons, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 11/136,619

(22) Filed: May 23, 2005

(65) Prior Publication Data

US 2005/0288226 A1 Dec. 29, 2005

Related U.S. Application Data

(60) Provisional application No. 60/664,241, filed on Mar. 21, 2005, provisional application No. 60/573,197, filed on May 21, 2004.

(51) Int. Cl.
*A61K 38/00* (2006.01)
*A61K 39/00* (2006.01)
(52) U.S. Cl. ............... 514/2; 424/185.1; 424/192.1
(58) Field of Classification Search ............... 514/2
See application file for complete search history.

(56) References Cited

U.S. PATENT DOCUMENTS

| 6,844,422 | B1 | 1/2005 | Niehrs et al. |
| 2002/0192216 | A1 | 12/2002 | Lamb et al. |
| 2003/0040051 | A1 | 2/2003 | Bhanot et al. |
| 2004/0126359 | A1 | 7/2004 | Lamb et al. |
| 2004/0171153 | A1 | 9/2004 | Andrews et al. |
| 2005/0049195 | A1 | 3/2005 | Zou |

FOREIGN PATENT DOCUMENTS

| EP | 1489168 | | 12/2004 |
| GB | 9913350.6 | | 6/1999 |
| WO | WO 97/39357 | A1 | 10/1997 |
| WO | WO 99/22000 | A1 | 5/1999 |
| WO | WO 00/74706 | A1 | 12/2000 |
| WO | WO 02/077204 | A2 | 10/2002 |
| WO | WO 02/080952 | A2 | 10/2002 |
| WO | WO 02/090992 | A2 | 11/2002 |
| WO | WO 2004/058949 | A2 * | 12/2003 |
| WO | WO 2004/026908 | A1 | 4/2004 |
| WO | WO 2004/058949 | A2 | 7/2004 |

OTHER PUBLICATIONS

Bowie et al (Science, 1990, 247:1306-1310).*
Freshney (Culture of Animal Cells, A Manual of Basic Technique, Alan R. Liss, Inc., 1983, New York, p. 4).*
Dermer (Bio/Technology, 1994, 12:320).*
Taniguchi et al, Oncogene 2005, 24:7946-7952.*
Lin et al (Human Gene Therapy, 2007, 18:379 abstract only).*
He, Biao et al.; "A Monoclonal Antibody against Wnt-1 Induces Apoptosis in Human Cancer Cells"; 2004, *Neoplasia*, vol. 6, No. 1, pp. 7-14.
Hsieh, Jen-Chih et al.; "A new secreted protein that binds to Wnt proteins and inhibits their activites"; 1999, *Nature*, vol. 398, pp. 431-436.
Wissmann, Christoph et al.; "WIFI, a component of the Wnt pathway, is down-regulated in prostate, breast, lung, and bladder cancer"; 2003, *J. Pathol.*, vol. 201, pp. 204-212.
He Biao et al, "Blockade of Wnt-1 signaling induces adoptosis in human colorectal cancer cells containing downstream mutations", Oncogene, vol. 24, No. 18, Apr. 18, 2005, pp. 3054-3058, XP002470043, ISSN:0950-9232.
Laird PW, "The Power and The Promise of DNA Methylation Markers", Nature Reviews. Cancer, Nature Publishing Group, London, GB, Vol. 3, No. 4, Apr. 2003, pp. 253-266, XP009044309, ISSN: 1474-175X.
Mazieres J et al, "Wnt signaling in ling cancer", Cancer Letters, New York, NY, US, vol. 222, No. 1, May 10, 2005, pp. 1-10, XP004856230, ISSN: 0304-3835.
Cebrat, Malgorzata et al.; "Wnt inhibitory factor-1: a candidate for a new player in tumorigenesis of intestinal epithelial cells"; 2004, Cancer Letters, vol. 206, pp. 107-113.
Chen, Shaoqiong et al.; "Wnt-1 Signaling Inhibits Apoptosis by Activating β-Catenin/T Cell Factor-mediated Transcription"; 2001, *The Journal of Cell Biology*, vol. 152, pp. 87-96.
Herman, James G. et al.; "Gene Silencing in Cancer in Association with Promoter Hypermethylation"; 2003, *The New England Journal of Medicine*, vol. 349, pp. 2042-2054.
Iiyas, Mohammad; "Wnt signalling and the mechanistic basis of tumour development"; 2005, *Journal of Pathology*, vol. 205, pp. 130-144.
Mazieres, Julien et al.; "Wnt Inhibitory Factor-1 is Silenced by Promoter Hypermethylation in Human Lung Cancer"; 2004, *Cancer Research*, vol. 64, pp. 4717-4720.
Ohigashi, T. et al.; "Inhibition of Wnt Signaling Downregulates Akt Activity and Induces Chemosensitivity in PTEN-Mutated Prostate Cancer Cells"; 2005, *The Prostate*, vol. 62, pp. 61-68.
Reguart, Noemi et al.; "Cloning and characterization of the promoter of human Wnt inhibitory factor-1"; 2004, *Biochemical and Biophysical Research Communications*, vol. 323, pp. 229-234.
Taniguchi, Hiroaki et al.; "Frequent epigenetic inactivation of Wnt inhibitory factor-1 in human gastrointestinal cancers"; 2005, *Oncogene*, pp. 1-7.
You, Zongbing et al.; "Wnt signaling promotes oncogenic transformation by inhibiting c-Myc-induced apoptosis"; 2002, *The Journal of Cell Biology*, vol. 157, No. 3, pp. 429-440.
Zochbauer-Muller, Sabine et al.; "Aberrant Promoter Methylation of Multiple Genes in Non-Small Cell Lung Cancers"; 2001, *Cancer Research*, vol. 61, pp. 249-255.

\* cited by examiner

*Primary Examiner*—Laura B Goddard
(74) *Attorney, Agent, or Firm*—Michael B. Rubin; Bozicevic, Field & Francis, LLP

(57) ABSTRACT

This invention provides compositions, methods and kits for the diagnosis and treatment of cancers wherein Wnt Inhibitory Factor-1 (WIF-1) is underexpressed.

41 Claims, 29 Drawing Sheets

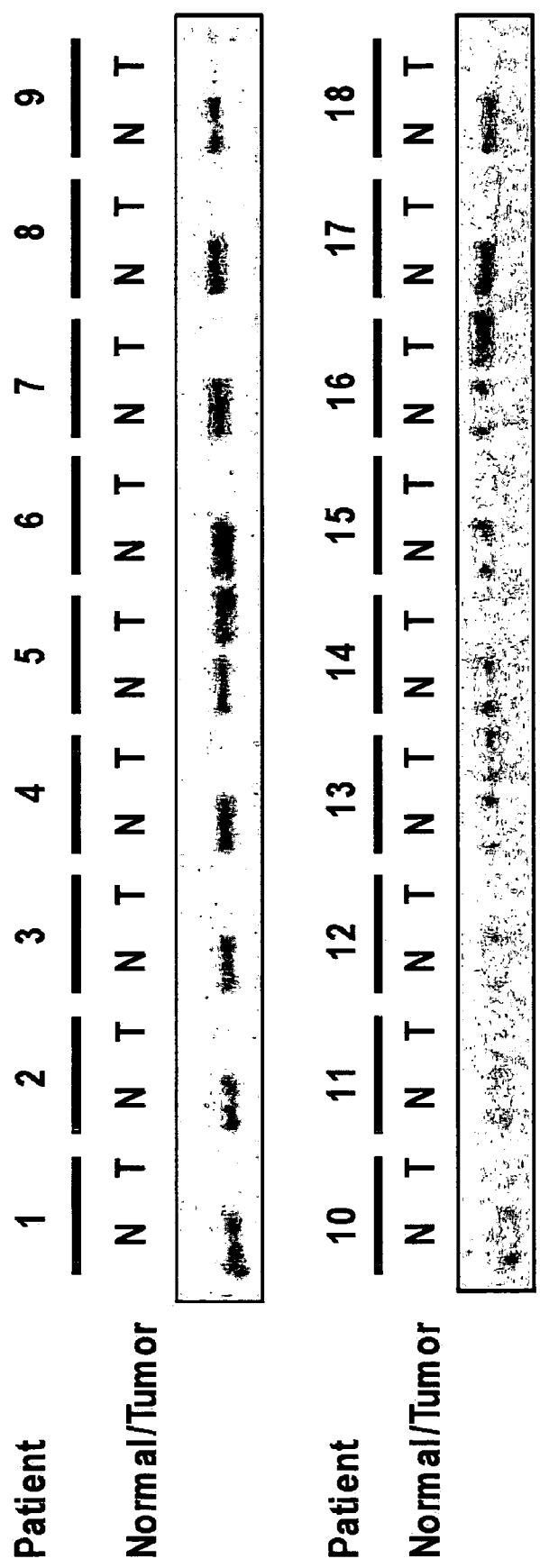

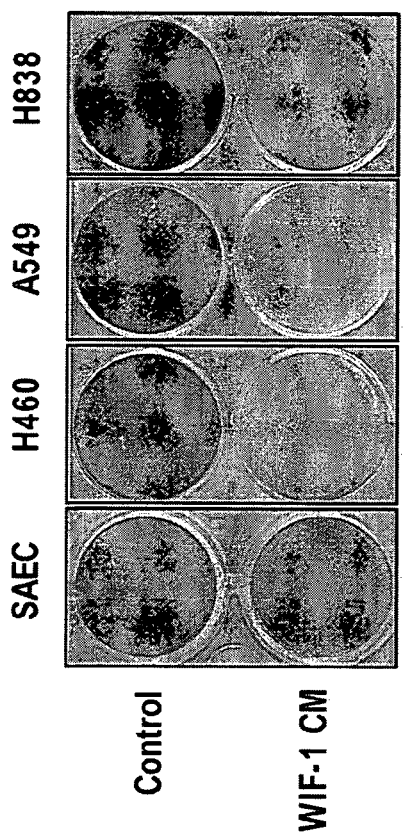
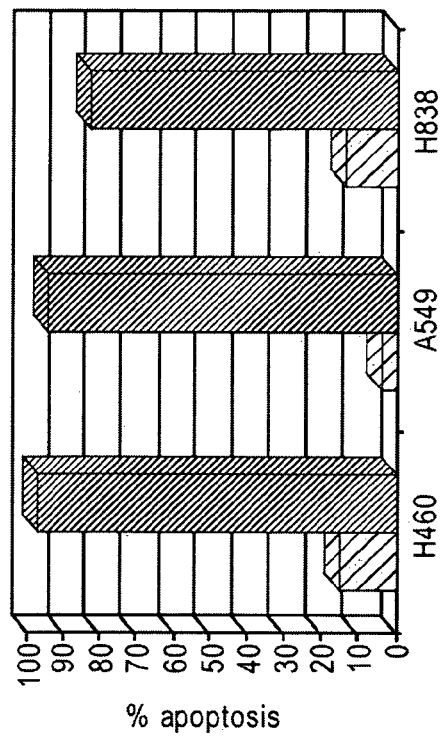
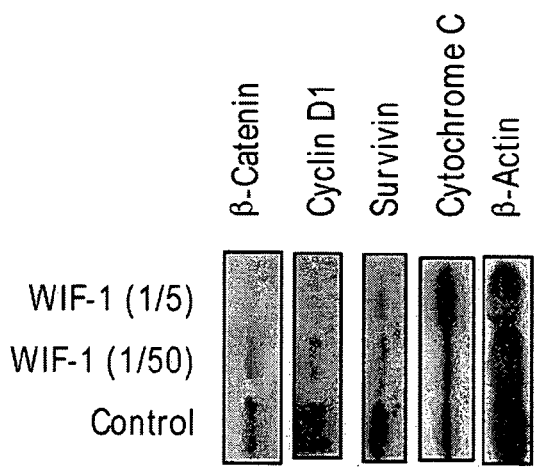
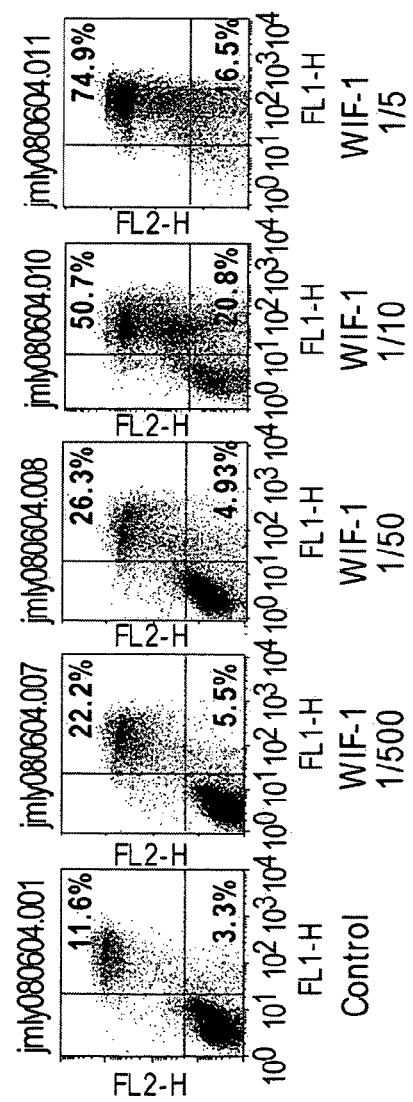
FIG. 7A
FIG. 7B
FIG. 7C
FIG. 7D

```
mWIF-1  MARRRAFPAFALRLWSILPCLLLLRADAGQPPEESLYLWIDAHQARVLIGFEEDILIVSE  60
rWIF-1  MARRRAFPAFVLRLWSILPCLLLLRADAGQPPEESLYLWIDAHQARVLIGFEEDILIVSE  60
hWIF-1  MARRSAFPAAALWLWSILLCLLALRAEAGPPQEESLYLWIDAHQARVLIGFEEDILIVSE  60
xWIF-1  MSLTGYFAAP---LCSIFLFILAH-ADAGQ-QEDSLYMWIDAHQARVLIGFEEDILIVAE  55
zWIF-1  MAFR--TPAVQLHLKACVLLLLGGLLEAAYQERGTMYMWIDANQARILIGFEEDILIVSE  58
         *:     .*      *  .:*    :*. . ::*:**:*:**********:* mWIF-1  GKMAPFTHDFRKAQQRMPAIPVNIHSMNFTWQAAGQAEYFYEFLSLRSLDKGIMADPTVN  120
rWIF-1  GKMAPFTHDFRKAQQRMPAIPVNIHSMNFTWQASGQAEYFYEFLSLRSLDKGIMADPTVN  120
hWIF-1  GKMAPFTHDFRKAQQRMPAIPVNIHSMNFTWQAAGQAEYFYEFLSLRSLDKGIMADPTVN  120
xWIF-1  GKMAPFTHDFRKAQQRMPAIPVNIHAMNFTWQATGQAEYFYEFLSLRSLDKGIMADPTVN  115
zWIF-1  GKMAPFTHDFRKAQQRMPAIPVNIHHVNFTWQATDQAEYFYEFQTLRSLDKDIMDDPTVN  118
        ***********************.*:.**** :*. ***** mWIF-1  VPLLGTVPHKASVVQVGFPCLGKQDGVAAFEVNVIVMNSEGNTILRTPQNAIFFKTCQQA  180
rWIF-1  VPRLGTVPHKASVVQVGFPCLGKQDGVAAFEVNVIVMNSEGNPILRTPQNAIFFKTCQQA  180
hWIF-1  VPLLGTVPHKASVVQVGFPCLGKQDGVAAFEVDVIVMNSEGNTILQTPQNAIFFKTCLQA  180
xWIF-1  MPLLGTVPHKATVIQVGFPCLGNQDGVAAFEVNVIVMNSEGNVILQTPQNAIFFKTCQQA  175
zWIF-1  VPLLGSVPHKASVVQVGFPCRGDQDGVAAFEVTILVMDAGGNIILRTPHNAIFFKTCQRA  178
         *  : :**** *.******  ::   ::******  :* mWIF-1  ECPGGCRNGGFCNERRVCECPDGFYGPHCEKALCIPRCMNGGLCVTPGFCICPPGFYGVN  240
rWIF-1  ECPGGCRNGGFCNERRVCECPDGFYGPHCEKALCIPRCMNGGLCVTPGFCICPPGFYGVN  240
hWIF-1  ECPGGCRNGGFCNERRICECPDGFHGPHCEKALCTPRCMNGGLCVTPGFCICPPGFYGVN  240
xWIF-1  KCTGGCRNGGFCNDRHVCECPDGFYGPHCEKALCMPRCMNGGLCVTPGLCICPPGYYGIN  235
zWIF-1  KCPGGCRNGGYCNERQVCECQDGFYVHCEKALCSPRCLNGGLCMSPGVCICPPGYFGSS  238
        :*.*******:**:*::*** ***:*  *******  *** *****::** *****::*  .

mWIF-1  CDKANCSTTCFNGGTCFYPGKCICPPGLEGEQCELSKCPQPCRNGGKCIGKSKCKCPKGY  300
rWIF-1  CDKANCSATCFNGGTCFYPGKCICPPGLEGEQCELSKCPQPCRNGGKCIGKSKCKCPKGY  300
hWIF-1  CDKANCSTTCFNGGTCFYPGKCICPPGLEGEQCEISKCPQPCRNGGKCIGKSKCKCSKGY  300
xWIF-1  CDKVNCTTHCLNGGTCFYPGKCICPSGYEGEQCETSKCQQPCRNGGKCSGKNKCKCSKGY  295
zWIF-1  CERANCSTTCLNGGTCFHPGKCICAVSFEGVRCELSKCRQPCRNGGKCTGRNKCKCSKGY  298
        *:: **:: *:***.**.    : * ********* *:.**.* mWIF-1  QGDLCSKPVCEPGCGAHGTCHEPNKCQCREGWHGRHCNKRYGASLMHAPRPAGAGLER-H  359
rWIF-1  QGDLCSKPVCEPGCGAHGTCHEPNKCQCREGWHGRHCNKRYGASLMHAPRPAGAGLER-H  359
hWIF-1  QGDLCSKPVCEPGCGAHGTCHEPNKCQCQEGWHGRHCNKRYEASLIHALRPAGAQLRQ-H  359
xWIF-1  QGDLCSKPVCEPSCGAHGTCIEPNKCQCKEGWNGRYCNKKYGSNLMNALRPTGSRNRQ-H  354
zWIF-1  HGDLCSKAVCEPSCGAHGTCVEPNRCQCREGWHGRHCNKRFRGGVSNSQRVSPSKHKSPS  358
         ******.****.******* ***:*** ***:**:****:     ..:  ::  * : .

mWIF-1  TPSLKKAEDRRDPPESNYIW  379
rWIF-1  TPSLKKAEGRRDPPESNYIW  379
hWIF-1  TPSLKKAEERRDPPESNYIW  379
xWIF-1  TPSPKRTEDRQALPESNYIW  374
zWIF-1  VAAAKEAPETSQPSETNYVV  378
         ..: *.:      .*:**:
```

FIG. 25

METHODS FOR TREATING AND DIAGNOSING CANCER WITH WNT INHIBITORY FACTOR-1 (WIF-1)

CROSS-REFERENCE TO RELATED APPLICATIONS

This application claims benefit of provisional application Ser. No. 60/573,197, filed May 21, 2004 and of provisional application Ser. No. 60/664,241, filed Mar. 21, 2005, the disclosures of which are incorporated in their entirety herein by reference.

BACKGROUND OF THE INVENTION

Cancer is a major killer throughout the world, and lung cancer is the leading cause of cancer mortality in most countries, causing over 1 million deaths worldwide each year. Further, more than 170,000 newly diagnosed lung cancer cases per year are reported in the United States (Fong et al., *Thorax* 58:892-900 (2003); Minna et al., *Cancer Cell* 1:49-52 (2002)).

The incidence of a number of different tumor types has risen in the last two decades. Recently, significant progress has been made in the understanding of molecular genetics of cancer. For instance, proto-oncogenes and tumor suppressor genes are cellular genes that regulate other genes involved in the control of normal cellular growth and differentiation. These genes code for growth factors, growth factor receptors, kinases that phosphorylate diverse cellular substrates, and DNA binding proteins that regulate expression of numerous cellular genes. Oncogenesis may occur through activation of dominant growth promoting proto-oncogenes where mutation (e.g., ras) or overexpression (e.g., Her-2/neu, and c-myc) of the gene product induces malignancy, and inactivation of growth inhibitory tumor suppressor genes (such as p53 and Rb) where the absence of expression or function of these genes results in malignancy. Such cancers have a genetic basis in that the changes responsible for the cancer are at the level of the nucleotide sequence of one or more genes in an individual.

In addition to above genetic changes, cancer also can be caused through epigenetic mechanisms. One epigenetic mechanism involves silencing of gene expression due to methylation of the gene sequence, particularly in CpG-rich regions (CpG islands). Aberrant methylation of normally unmethylated CpG islands has been associated with transcriptional inactivation of defined tumor suppressor genes in human cancers. Epigenetic mechanisms such as methylation silencing of gene transcription provide markers useful for determining whether a cell is susceptible to loss of normal growth control and, therefore, potentially a cancer cell. Cancer often is a silent disease that does not present clinical signs or symptoms until the disease is well advanced. As such, the use of markers that allow the identification of individuals susceptible to a cancer, or even that allow detection of a cancer at an early stage, are of great benefit.

Unfortunately, such markers are not available for most cancers. For example, early non-small-cell lung cancer (NSCLC) is routinely resected with survival rates of 35 to 85%, depending on tumor stage. Unfortunately, most lung cancers are detected late, so that the overall five-year survival rate for NSCLC is only 15%. A major factor in the high mortality of lung cancer patients is the presence of metastatic tumors in approximately two-thirds of patients at time of diagnosis. Detection of cancer in these patients at earlier stages could potentially increase survival rates. DNA methylation detection is a promising approach for identifying lung cancer-specific biomarkers, and it is also a non-invasive method for the detection of biomarkers at an early stage.

The Wnt family of secreted glycoproteins is a group of signaling molecules that is widely involved in developmental processes and oncogenesis (WO 04/032838). The proto-oncogenic effects of Wnt were discovered more than 20 years ago. Since then numerous reports have demonstrated aberrant activation of Wnt signaling pathway in disparate human cancers such as colorectal cancer, head and neck carcinoma (Rhee et al., *Oncogene* 21:6598-605 (2002)), melanoma (Weeraratna et al., *Cancer Cell*. 1:279-88 (2002)) and leukemia (Jemal et al., *Cancer J. Clin.* 54:8-29 (2004)).

Recently, it was reported that Dvl proteins are overexpressed in mesothelioma and NSCLC (Uestema et al., *Oncogene* 22:7218-7221 (2003)). It was also demonstrated that inhibition of Wnt-1 induces apoptosis and inhibits tumor growth in lung cancer cell lines (Li et al., *J. Biol. Chem.* 277:5877-81 (2002)). Wnt antagonists can be divided into two groups according to the mechanisms of their functions: the first group includes the secreted Frizzled-related protein (sFRP) family, WNT-Inhibitory Factor-1 (WIF-1) and Cerberus. These antagonists inhibit Wnt signaling by direct binding to Wnt molecules. The second group includes the Dickkopf (DKK) family, which inhibits Wnt signaling by binding to the LRP5/LRP6 component of the Wnt receptor complex (Kawano et al., *J. Cell Sci.* 116:2627-34 (2003)).

WIF-1 is a naturally secreted Wnt signaling antagonist. WIF-1 is made as 379 amino acid residue protein. WIF-1 has an N-terminal signal sequence of 28 amino acid residues, a unique WIF domain (WD) of approximately 150 amino acid residues, five epidermal growth factor (EGF)-like repeats and a 45 amino aci residue C-terminal hydrophilic domain (Hsieh et al., *Nature* 398:431-436 (1999); GenBank NP_009122). WIF-1 does not share any similarities with the CRD (cysteine rich domain) of Fz or sFRP (Bui et al., *Oncogene* 14(10): 1249-53 (1997); Melkonyan et al., *Proc. Natl. Acad. Sci. USA* 94(25):13636-41 (1997); Shimizu et al., *Cell. Growth Differ.* 8(12):1349-58 (1997); and Todd et al., *Cancer Res.* 57(7): 1344-52 (1997)). WIF-1 has been implicated in the regulation of several developmental processes. For example, it was shown that overexpression of WIF-1 in *Xenopus* embryos blocks the Wnt-8 pathway and induces abnormal somitogenesis (Hsieh et al., *Proc. Natl. Acad. Sci. USA* 96:3546-51 (1999)).

Despite advances in the therapy of lung cancer during the past decades, the 5-year survival rate for lung cancer remains under 15%. NSCLC accounts for 75-80% of all lung cancers. A better understanding of molecular mechanisms for lung cancer pathogenesis should improve the treatment of patients with lung cancer. The present invention provides compositions, methods and kits useful for the detection and treatment of cancer wherein WIF-1 expression is down-regulated, such as lung cancer, and for inducing apoptosis in cells wherein WIF-1 expression is down-regulated.

BRIEF SUMMARY OF THE INVENTION

One aspect of this invention is based on the discovery that frequent hypermethylation in CpG islands of a WIF-1 promoter correlates with its transcription silencing in cancer cells and with underexpression of WIF-1. Thus, in some aspects of the present invention, compositions are provided that are useful in a variety of ways, for example for inhibiting the proliferation of a cancer cell that underexpresses WIF-1, for inducing apoptosis in a cancer cell that underexpresses WIF-1, for inhibiting Wnt signaling in a cancer cell and for treating a disease associated with underexpression of WIF-1.

In a preferred embodiment of the present invention, a composition comprises a Wnt-Inhibitory Factor-1 (WIF-1) subdomain polypeptide that binds to a Wnt polypeptide. Preferred is a WIF-1 subdomain polypeptide that inhibits Wnt signaling. In a preferred embodiment, the WIF-1 subdomain polypeptide comprises an amino acid sequence that corresponds to about amino acid residues 1-180 of SEQ ID NO:2. Other preferred WIF-1 subdomain polypeptides comprises an amino acid sequence that corresponds to about amino acid residues 29-180 of SEQ ID NO:2, amino acid residues 29-176 of SEQ ID NO:2 or amino acid residues 39-176 of SEQ ID NO:2. Also preferred is a WIF-1 subdomain polypeptide which is fused to an amino acid sequence that is heterologous to a WIF-1 polypeptide.

The present invention provides a method of inhibiting proliferation of a cancer cell that underexpresses WIF-1. This method comprises the step of contacting the cancer cell with an amount of a WIF-1 polypeptide effective to inhibit the proliferation of the cancer cell. In a preferred embodiment of the present invention, the cancer cell comprises a hypermethylated WIF-1 promoter and the step of contacting the cancer cell comprises increasing expression of WIF-1 in the cancer cell by decreasing the methylation of the WIF-1 promoter.

In another preferred embodiment of the present invention, the amount of a WIF-1 polypeptide induces apoptosis in the cancer cell.

The step of contacting the cancer cell can comprise expressing the WIF-1 polypeptide in the cancer cell from an isolated polynucleotide comprising a sequence that encodes the WIF-1 polypeptide.

This invention further provides a method of inducing apoptosis in a cancer cell that underexpresses WIF-1. This method comprises the step of contacting the cancer cell with a polypeptide having WIF-1 activity in an amount effective to induce apoptosis in the cancer cell.

Another preferred method of the present invention is a method of inhibiting Wnt signaling in a cancer cell comprising the step of contacting the cancer cell with an amount of a WIF-1 polypeptide effective to inhibit Wnt signaling in the cancer cell.

This invention also provides a method of treating a disease associated with underexpression of WIF-1. This method comprises the step of administering to a subject in need of such treatment an amount of a polypeptide having WIF-1 activity effective for treating the disease. A preferred disease is cancer.

The present invention also provides a method for detecting a hypermethylated WIF-1 promoter. In a preferred embodiment, this method comprises the step of contacting the hypermethylated WIF-1 promoter with an oligonucleotide comprising a sequence that specifically hybridizes to the hypermethylated WIF-1 promoter, in an amount effective to detect the hypermethylated WIF-1 promoter.

Cancer cells that find use in the methods of the present invention, or cancers that can be diagnosed and/or treated using a composition, method or kit of the present invention include lung cancer, breast cancer, colorectal cancer, melanoma, colon cancer, mesothelioma, ovarian cancer, gastric cancer, kidney cancer, bladder cancer, prostate cancer, uterus cancer, thyroid cancer, pancreatic cancer, cervical cancer, esophageal cancer, head and neck cancer, hepatocellular carcinoma, brain tumor, vulval cancer, testical cancer, sarcoma, leukemia, lymphoma, glioma and glioblastoma.

A preferred WIF-1 polypeptide that can be used in the methods of the present invention is a WIF-1 subdomain polypeptide. The WIF-1 subdomain polypeptide may comprise an amino acid sequence that corresponds to about amino acid residues 1-180 of SEQ ID NO:2, an amino acid sequence that corresponds to about amino acid residues 29-180 of SEQ ID NO:2, an amino acid sequence that corresponds to about amino acid residues 29-176 of SEQ ID NO:2 or an amino acid sequence that corresponds to about amino acid residues 39-176 of SEQ ID NO:2. Also preferred is a WIF-1 subdomain polypeptide which is fused to an amino acid sequence that is heterologous to a WIF-1 polypeptide.

The methods of the present invention can be practiced in vitro and in vivo.

The present invention also provides pharmaceutical compositions comprising a WIF-1 polypeptide and a pharmaceutically acceptable excipient, carrier, and/or diluent. Pharmaceutical compositions embrace the WIF-1 polypeptides described herein.

BRIEF DESCRIPTION OF THE DRAWINGS

FIG. 4A shows WIF-1 expression in primary human lung cancer tissue samples.

FIG. 7 shows that WIF-1 CM induces apoptosis in NSCLC cell lines. Panel A shows 0.5% Crystal Violet staining of SAEC cells and three NSCLC cell lines (H460, A549, and H838) after the WIF-1 CM treatment (~5-7 days after treatment). Panel B shows that WIF-1 CM induces apoptosis in three NSCLC cell lines (H460, A549, and H838). This panel shows examples of apoptosis analysis by flow cytometry. NSCLC cells were treated with WIF-1 CM for about 5-7 days (dark bar). Serum-free medium collected from 293T cells was used as control (light bar). Panel C shows a flow cytometry analysis of H460 cells (5 days after treatment) as an example of dose-dependent apoptosis induction. FL1-H represents Annexin V-FITC staining. Panel D shows a Western analysis before ("control") and after WIF-1 CM treatments of 72 hrs (WIF-1 (1/50)" and "WIF-1 (1/5)"). This analysis shows that human WIF-1 inhibits Wnt signaling pathway in the lung cancer cell line H460. Expression of β-catenin, Survivin, Cyclin D1, and Cytochrome C was analyzed. β-Actin served as a loading control. Cytosolic proteins were prepared. Whole cell protein was used for cyclin D1 analysis.

FIG. 25 shows an alignment of WIF-1 amino acid sequences for human (hWIF-1; se SEQ ID NO:2 and GenBank Accession No. NP_009122) and the corresponding sequences from mouse (mWIF-1; see SEQ ID NO:22 and GenBank Accession No. NP_036045), rat (rWIF-1; see SEQ ID NO:23 and GenBank Accession No. Q61N38), Xenopus (xWIF-1; see SEQ ID NO:24 and GenBank Accession No. AAD25404) and zebrafish (zWIF-1, see SEQ ID NO:25 and GenBank Accession No. Q9W6F9). "*" indicates identity of WIF-1 amino acid residues at the indicated position in the WIF-1 sequences aligned; ":" indicates positions where conserved amino acid substitutions are found; "." indicates positions where non-conserved amino acid substitutions are found.

DETAILED DESCRIPTION OF THE INVENTION

I. Definitions

Figure 1:
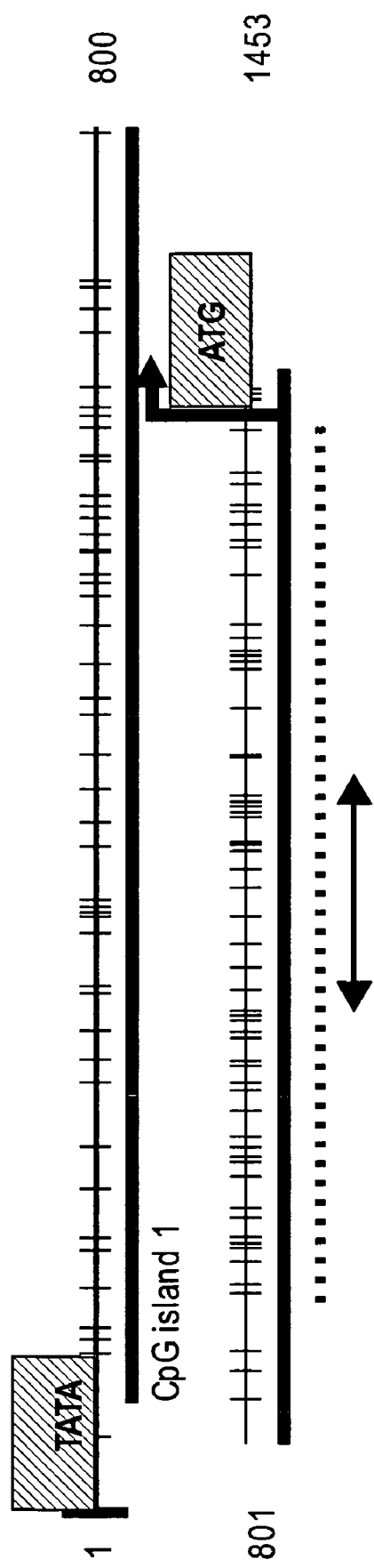
FIG. 1 shows CpG island in the human WIF-1 promoter region.

The term "WIF-1" refers to nucleic acids, polypeptides and polymorphic variants, alleles, mutants, and interspecies homologues thereof and as further described herein, that: (1) have an amino acid sequence that has greater than about 60% amino acid sequence identity, 65%, 70%, 75%, 80%, 85%, 90%, preferably 91%, 92%, 93%, 94%, 95%, 96%, 97%, 98% or 99% or greater amino acid sequence identity, preferably over a region of at least about 25, 50, 75, 100, 150, 200, 250, 300, 350, or 379 amino acids, to a WIF-1 sequence shown below; (2) bind to antibodies, e.g., polyclonal antibodies, raised against an immunogen comprising an amino acid sequence shown below, or conservatively modified variants thereof; (3) bind to a Wnt protein; (4) interfere with Wnt binding to a Wnt binding molecule; (5) inhibit at least partially the Wnt signaling pathway; (6) specifically hybridize under stringent hybridization conditions to a nucleic acid sequence shown below, or conservatively modified variants thereof; (7) have a nucleic acid sequence that has greater than about 90%, preferably greater than about 96%, 97%, 98%, 99%, or higher nucleotide sequence identity, preferably over a region of at least about 30, 50, 100, 200, 500, 1000, 1,500, 2000 or more nucleotides, to SEQ ID NO:1; SEQ ID NO: 3, SEQ ID NO:17, SEQ ID NO:18 or SEQ ID NO:19; and/or (8) have at least 25, often 50, 75, 100, 150, 200, 250, 300, 350, or 379 contiguous amino acid residues of SEQ ID NO:2, SEQ ID NO: 14, SEQ ID NO:15, SEQ ID NO:16, SEQ ID NO:26, SEQ ID NO:27, SEQ ID NO:28, SEQ ID NO:29 or SEQ ID NO:30; or at least 25, often 50, 75, 100, 150, 200, 250, 300, 350, 400, 500, 600, 700, 800, 900, 1,000, 1,200, 1,500, 2,000 or more contiguous nucleotides of SEQ ID NO:1, SEQ ID NO: 3, SEQ ID NO:17, SEQ ID NO:18 or SEQ ID NO:19.

A WIF-1 polynucleotide or polypeptide sequence is typically from a human, but may be from other mammals, but not limited to, a non-human primate, a rodent, e.g., a rat, mouse, or hamster; a cow, a pig, a horse, a sheep, or other mammal. A "WIF-1" polypeptide and polynucleotide include both naturally occurring or recombinant forms. Therefore, in some embodiments, a WIF-1 polypeptide and a WIF-1 subdomain polypeptide as described herein can comprise a sequence that corresponds to a human WIF-1 sequence. Thus, exemplary WIF-1 are provided herein and are known in the art. For example, GenBank accession numbers for human WIF-1 polypeptides are AAD25402, AAQ88710, AAH18037, NP_009122 and Q9YSW5. There is some amino acid sequence heterogeneity with respect to amino acid residue 178 of the full-length WIF-1. Leucine and glutamine amino acid residues have been reported at this position. GenBank accession numbers for mouse WIF-1 polypeptides are, for example, Q9WUA1, NP_036045 and AAD25403; for rat WIF-1, Q61N38; for bovine, XP_582244; for *Xenopus laevis*, AAD25404 and Q9W6F8; and for zebrafish, Q9W6F9 and AAD25405.

The terms "Wnt," "Wnt polypeptide" or "Wnt ligand" refer to a family of mammalian proteins related to the *Drosophila* segment polarity gene, wingless. In humans, the Wnt family of genes typically encode 38 to 43 kDa cysteine rich glycoproteins having hydrophobic signal sequence, and a conserved asparagine-linked oligosaccharide consensus sequence (Shimizu et al., *Cell Growth Differ* 8(12):1349-58 (1997)). The Wnt family contains at least 19 mammalian members. Exemplary Wnt proteins include Wnt1, Wnt2, Wnt3, Wnt3A, Wnt4, Wnt5A, Wnt5B, Wnt6, Wnt7A, Wnt7B, Wnt8A, Wnt8B, WNT10A, Wnt10B, Wnt11, Wnt12, Wnt13, Wnt14, Wnt15, and Wnt16. Preferably a Wnt polypeptide is a mammalian Wnt polypeptide, more preferably, a human Wnt polypeptide.

The terms "Wnt-binding subdomain protein" "WIF-1 domain protein, "WIF-1 subdomain polypeptide," "WD protein" or grammatical equivalents thereof in the context of a WIF-1 protein refer to a fragment of WIF-1 protein which can bind to a Wnt polypeptide or which can interfere with a Wnt signaling pathway.

A "WIF-1 related" polypeptide as used herein, refers to a WIF-1 homolog, a WIF-1 isoform, a WIF-1 ortholog, a WIF-1 fusion protein or fragments of the foregoing or any combination thereof.

A "WIF-1 homolog" refers to a polypeptide that comprises an amino acid sequence similar to that of WIF-1 but does not necessarily possess a similar or identical function as WIF-1.

A "WIF-1 isoform" refers to a variant of WIF-1 that is encoded by the same gene, but differs in its pI or MW, or both. Such isoforms can differ in their amino acid composition (e.g., as a result of alternative splicing or limited proteolysis) and in addition, or in the alternative, may arise from differential post-translational modification (e.g., glycosylation, acylation or phosphorylation).

A "WIF-1 ortholog" as used herein refers to a non-human polypeptide that (i) comprises an amino acid sequence similar to that of human WIF-1 and (ii) possess a similar or identical function to that of human WIF-1.

A "WIF-1 fusion protein" as used herein refers to a polypeptide that comprises (i) an amino acid sequence of a WIF-1, a WIF-1 fragment, a WIF-1 subdomain polypeptide, a WIF-1 related polypeptide or a fragment of a WIF-1 related polypeptide and (ii) an amino acid sequence of a heterologous polypeptide (i.e., a non-WIF-1, non-WIF-1 fragment or non-WIF-1 related polypeptide).

A "full length" WIF-1 polypeptide or nucleic acid refers to a WIF-1 polypeptide or polynucleotide sequence, or a variant thereof, that contains all of the elements normally contained in one or more naturally occurring, wild type WIF-1 polynucleotide or polypeptide sequences. The "full length" may be prior to, or after, various stages of post-translation processing or splicing, including alternative splicing and signal peptide cleavage.

The term "hypermethylation" refers to methylation of cytosine at a position that is normally unmethylated in the WIF-1 gene sequence, e.g., the WIF-1 promoter. As appreciated by one of skill in the art, detection of hypermethylation in a region of the WIF-1 gene such as the promoter does not require that every CpG residue in the promoter be analyzed. One or more CpG residues may be the target in a methylation analysis. Thus, typically, "hypermethylation" in the context of a polynucleotide sequence refers to an increase in the number of methylated bases as compared to a control (e.g., a cancer cell vs. a non-cancer cell). "Hypermethylation" also refers to the number or frequency of cytosine residues comprising an added methyl group as compared to a control.

The "WIF-1 promoter" refers to a sequence comprising one or more regulatory regions that control transcription of "WIF-1". In some embodiments, a WIF-1 promoter is a human WIF-1 promoter. An exemplary human WIF-1 promoter sequence comprises the nucleotide sequence set forth in SEQ ID NO:3.

"Decreasing the methylation" in the context of a polynucleotide sequence, such as a WIF-1 promoter, refers to a decrease in the number of methylated bases as compared to a control (e.g., a cancer cell vs. a non-cancer cell). The term also refers to the number or frequency of cytosine residues comprising an added methyl group as compared to a control.

"Biological sample" as used herein is a sample of biological tissue or fluid that contains nucleic acids or polypeptides. Such samples are typically from humans, but include tissues isolated from non-human primates, or rodents, e.g., mice, and rats. Biological samples may also include sections of tissues such as biopsy and autopsy samples, frozen sections taken for histological purposes, blood, plasma, serum, sputum, stool, tears, mucus, hair, skin, etc. Biological samples also include explants and primary and/or transformed cell cultures derived from patient tissues. A "biological sample" also refers to a cell or population of cells or a quantity of tissue or fluid from an animal. Most often, the biological sample has been removed from an animal, but the term "biological sample" can also refer to cells or tissue analyzed in vivo, i.e., without removal from the animal. Typically, a "biological sample" will contain cells from the animal, but the term can also refer to noncellular biological material, such as noncellular fractions of blood, saliva, or urine, that can be used to measure the cancer-associated polynucleotide or polypeptide levels. Numerous types of biological samples can be used in the present invention, including, but not limited to, a tissue biopsy, a blood sample, a buccal scrape, a saliva sample, or a nipple discharge. As used herein, a "tissue biopsy" refers to an amount of tissue removed from an animal, preferably a human, for diagnostic analysis. In a patient with cancer, tissue may be removed from a tumor, allowing the analysis of cells within the tumor. "Tissue biopsy" can refer to any type of biopsy, such as needle biopsy, fine needle biopsy, surgical biopsy, etc.

"Providing a biological sample" means to obtain a biological sample for use in methods described in this invention. Most often, this will be done by removing a sample of cells from a patient, but can also be accomplished by using previously isolated cells (e.g., isolated by another person, at another time, and/or for another purpose), or by performing the methods of the invention in vivo. Archival tissues, having treatment or outcome history, will be particularly useful.

The "level of WIF-1 mRNA" in a biological sample refers to the amount of mRNA transcribed from a WIF-1 gene that is present in a cell or a biological sample. The mRNA generally encodes a functional WIF-1 protein, although mutations may be present that alter or eliminate the function of the encoded protein. A "level of WIF-1 mRNA" need not be quantified, but can simply be detected, e.g., a subjective, visual detection by a human, with or without comparison to a level from a control sample or a level expected of a control sample.

The "level of WIF-1 protein or polypeptide" in a biological sample refers to the amount of polypeptide translated from WIF-1 mRNA that is present in a cell or biological sample. The polypeptide may or may not have WIF-1 protein activity. A "level of WIF-1 protein" need not be quantified, but can simply be detected, e.g., a subjective, visual detection by a human, with or without comparison to a level from a control sample or a level expected of a control sample.

As used herein, the terms "treat", "treating", and "treatment" include: (1) preventing a disease, such as cancer, i.e. causing the clinical symptoms of the disease not to develop in a subject that may be predisposed to the disease but does not yet experience any symptoms of the disease; (2) inhibiting the disease, i.e. arresting or reducing the development of the disease or its clinical symptoms; or (3) relieving the disease, i.e. causing regression of the disease or its clinical symptoms. Preferably, the subject in need of such treatment is a mammal, more preferable a human.

The terms "identical" or percent "identity," in the context of two or more nucleic acids or polypeptide sequences, refer to two or more sequences or subsequences that arc the same or have a specified percentage of amino acid residues or nucleotides that are the same (i.e., about 60% identity, preferably 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see, e.g., NCBI web site or the like). Such sequences are then said to be "substantially identical." This definition also refers to, or may be applied to, the compliment of a test sequence. The definition also includes sequences that have deletions and/or additions, as well as those that have substitutions, as well as naturally occurring, e.g., polymorphic or allelic variants, and man-made variants. As described below, the preferred algorithms can account for gaps and the like. Preferably, identity exists over a region that is at least about 25 amino acids or nucleotides in length, or more preferably over a region that is 50-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of one of the number of contiguous positions selected from the group consisting typically of from about 20 to about 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1995 supplement)).

Preferred examples of algorithms that are suitable for determining percent sequence identity and sequence similarity include the BLAST and BLAST 2.0 algorithms, which are described in Altschul et al., *Nuci. Acids Res.* 25:3389-3402 (1977) and Altschul et al., *J. Mol. Biol.* 215:403-410 (1990). BLAST and BLAST 2.0 are used, with the parameters described herein, to determine percent sequence identity for the nucleic acids and proteins of the invention. Software for performing BLAST analyses is publicly available through the web site of the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, e.g., for nucleotide sequences, the parameters M (reward score for a pair of matching residues; always>0) and N (penalty score for mismatching residues; always<0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, $M=5$, $N=-4$ and a comparison of both strands. For amino acid sequences, the BLASTP program uses as defaults a wordlength of 3, and expectation (E) of 10, and the BLOSUM62 scoring matrix (see Henikoff & Henikoff, *Proc. Nati. Acad. Sci.* USA 89:10915 (1989)) alignments (B) of 50, expectation (E) of 10, $M=5$, $N=-4$, and a comparison of both strands.

The BLAST algorithm also performs a statistical analysis of the similarity between two sequences (see, e.g., Karlin & Altschul, *Proc. Natl. Acad. Sci. USA* 90:5873-5787 (1993)).

One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001. Log values may be large negative numbers, e.g., 5, 10, 20, 30, 40, 40, 70, 90, 110, 150, 170, etc.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, e.g., where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequences.

A "host cell" is a naturally occurring cell or a transformed cell that contains an expression vector and supports the replication or expression of the expression vector. Host cells may be cultured cells, explants, cells in vivo, and the like. Host cells may be prokaryotic cells such as E. coli, or eukaryotic cells such as yeast, insect cells, amphibian cells, or mammalian cells such as CHO, 293, 3T3, HeLa, and the like (see, e.g., American Type Culture Collection).

The terms "isolated," "purified," or "biologically pure" refer to material that is substantially or essentially free from components that normally accompany it as found in its native state. Purity and homogeneity are typically determined using analytical chemistry techniques such as polyacrylamide gel electrophoresis or high performance liquid chromatography. A protein or nucleic acid that is the predominant species present in a preparation is substantially purified. In particular, an isolated nucleic acid is separated from some open reading frames that naturally flank the gene and encode proteins other than protein encoded by the gene. The term "purified" in some embodiments denotes that a nucleic acid or protein gives rise to essentially one band in an electrophoretic gel. Preferably, it means that the nucleic acid or protein is at least 85% pure, more preferably at least 95% pure, and most preferably at least 99% pure. "Purify" or "purification" in other embodiments means removing at least one contaminant from the composition to be purified. In this sense, purification does not require that the purified compound be homogenous, e.g., 100% pure.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers, those containing modified residues, and non-naturally occurring amino acid polymer.

The term "amino acid" refers to naturally occurring and synthetic amino acids, as well as amino acid analogs and amino acid mimetics that function similarly to the naturally occurring amino acids. Naturally occurring amino acids are those encoded by the genetic code, as well as those amino acids that are later modified, e.g., hydroxyproline, γ-carboxyglutamate, and O-phosphoserine. "Amino acid analog" refers to a compound that has the same basic chemical structure as a naturally occurring amino acid, e.g., an a carbon that is bound to a hydrogen, a carboxyl group, an amino group, and an R group, e.g., homoserine, norleucine, methionine sulfoxide, methionine methyl sulfonium. Such analogs may have modified R groups (e.g., norleucine) or modified peptide backbones, but retain the same basic chemical structure as a naturally occurring amino acid. "Amino acid mimetic" refers to a chemical compound that has a structure that is different from the general chemical structure of an amino acid, but that functions similarly to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical or associated, e.g., naturally contiguous, sequences. Because of the degeneracy of the genetic code, a large number of functionally identical nucleic acids encode most proteins. For instance, the codons GCA, GCC, GCG and GCU all encode the amino acid alanine. Thus, at every position where an alanine is specified by a codon, the codon can be altered to another of the corresponding codons described without altering the encoded polypeptide. Such nucleic acid variations are "silent variations," which are one species of conservatively modified variations. Every nucleic acid sequence herein which encodes a polypeptide also describes silent variations of the nucleic acid. One of skill will recognize that in certain contexts each codon in a nucleic acid (except AUG, which is ordinarily the only codon for methionine, and TGG, which is ordinarily the only codon for tryptophan) can be modified to yield a functionally identical molecule. Accordingly, an often silent variations of a nucleic acid which encodes a polypeptide is implicit in a described sequence with respect to the expression product, but not with respect to actual probe sequences.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention typically conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, *Proteins* (1984)).

Macromolecular structures such as polypeptide structures can be described in terms of various levels of organization. For a general discussion of this organization, see, e.g., Alberts et al., *Molecular Biology of the Cell* (3$^{rd}$ ed., 1994) and Cantor & Schimmel, *Biophysical Chemistry Part I: The Conforma-* tion of Biological Macromolecules (1980). "Primary structure" refers to the amino acid sequence of a particular peptide. "Secondary structure" refers to locally ordered, three dimensional structures within a polypeptide. These structures are commonly known as domains. Domains are portions of a polypeptide that often form a compact unit of the polypeptide and are typically 25 to approximately 500 amino acids long. Typical domains are made up of sections of lesser organization such as stretches of β-sheet and α-helices. "Tertiary structure" refers to the complete three dimensional structure of a polypeptide monomer. "Quaternary structure" refers to the three dimensional structure formed by independent tertiary units, usually by noncovalent association.

"Nucleic acid" or "oligonucleotide" or "polynucleotide" or grammatical equivalents used herein means at least two nucleotides covalently linked together. Oligonucleotides are typically from about 5, 6, 7, 8, 9, 10, 12, 15, 25, 30, 40, 50 or more nucleotides in length, up to about 100 nucleotides in length. Nucleic acids and polynucleotides are a polymers of any length, including longer lengths, e.g., 200, 300, 500, 1000, 2000, 3000, 5000, 7000, 10,000, etc. A nucleic acid of the present invention will generally contain phosphodiester bonds, although in some cases, nucleic acid analogs are included that may have alternate backbones, comprising, e.g., phosphoramidate, phosphorothioate, phosphorodithioate, or O-methylphophoroamidite linkages (see, Eckstein, *Oligonucleotides and Analogues: A Practical Approach*, Oxford University Press); and peptide nucleic acid backbones and linkages. Other analog nucleic acids include those with positive backbones; non-ionic backbones, and non-ribose backbones, including those described in U.S. Pat. Nos. 5,235,033 and 5,034,506, and Chapters 6 and 7, ASC Symposium Series 580, *Carbohydrate Modifications in Antisense Research*, Sanghui & Cook, eds. Nucleic acids containing one or more carbocyclic sugars are also included within one definition of nucleic acids. Modifications of the ribose-phosphate backbone may be done for a variety of reasons, e.g. to increase the stability and half-life of such molecules in physiological environments or as probes on a biochip. Mixtures of naturally occurring nucleic acids and analogs can be made; alternatively, mixtures of different nucleic acid analogs, and mixtures of naturally occurring nucleic acids and analogs may be made.

A variety of references disclose such nucleic acid analogs, including, for example, phosphoramidate (Beaucage et al., *Tetrahedron* 49(10):1925 (1993) and references therein; Letsinger, *J. Org. Chem.* 35:3800 (1970); Sprinzl et al., *Eur. J. Biochem.* 81:579 (1977); Letsinger et al., *Nuc. Acids Res.* 14:3487 (1986); Sawai et al., *Chem. Lett.* 805 (1984), Letsinger et al., *J. Am. Chem. Soc.* 110:4470 (1988); and Pauwels et al., *Chemica Scripta* 26:141 91986)), phosphorothioate (Mag et al., *Nucleic Acids Res.* 19:1437 (1991); and U.S. Pat. No. 5,644,048), phosphorodithioate (Briu et al., *J. Am. Chem. Soc.* 111:2321 (1989), O methylphophoroamidite linkages (see, Eckstein, *Oligonucleotides and Analogues: A Practical Approach*, Oxford University Press), and peptide nucleic acid backbones and linkages (see, Egholm, *J. Am. Chem. Soc.* 114:1895 (1992); Meier et al., *Chem. Int. Ed. Engl.* 31:1008 (1992); Nielsen, *Nature* 365:566 (1993); Carlsson et al., *Nature* 380:207 (1996), all of which are incorporated by reference). Other analog nucleic acids include those with positive backbones (Denpcy et al., *Proc. Natl. Acad. Sci. USA* 92:6097 (1995); non ionic backbones (U.S. Pat. Nos. 5,386,023, 5,637,684, 5,602,240, 5,216,141 and 4,469,863; Kiedrowshi et al., *Angew. Chem. Intl. Ed. English* 30:423 (1991); Letsinger et al., *J. Am. Chem. Soc.* 110:4470 (1988); Letsinger et al., *Nucleoside & Nucleotide* 13:1597 (1994); Chapters 2 and 3, ASC Symposium Series 580, "*Carbohydrate Modifications in Antisense Research*", Ed. Y. S. Sanghui and P. Dan Cook; Mesmaeker et al., *Bioorganic & Medicinal Chem. Lett.* 4:395 (1994); Jeffs et al., *J. Biomolecular NMR* 34:17 (1994); *Tetrahedron Lett.* 37:743 (1996)) and non ribose backbones, including those described in U.S. Pat. Nos. 5,235,033 and 5,034,506, and Chapters 6 and 7, ASC Symposium Series 580, "*Carbohydrate Modifications in Antisense Research*", Ed. Y. S. Sanghui and P. Dan Cook. Nucleic acids containing one or more carbocyclic sugars are also included within one definition of nucleic acids (see, Jenkins et al., *Chem. Soc. Rev.* pp 169 176 (1995)). Several nucleic acid analogs are described in Rawls, C & E News Jun. 2, 1997 page 35. All of these references are hereby expressly incorporated by reference.

Other analogs include peptide nucleic acids (PNA) which are peptide nucleic acid analogs. These backbones are substantially non-ionic under neutral conditions, in contrast to the highly charged phosphodiester backbone of naturally occurring nucleic acids. This results in two advantages. First, the PNA backbone exhibits improved hybridization kinetics. PNAs have larger changes in the melting temperature ($T_m$) for mismatched versus perfectly matched base pairs. DNA and RNA typically exhibit a 2-4° C. drop in $T_m$ for an internal mismatch. With the non-ionic PNA backbone, the drop is closer to 7-9° C. Similarly, due to their non-ionic nature, hybridization of the bases attached to these backbones is relatively insensitive to salt concentration. In addition, PNAs are not degraded by cellular enzymes, and thus can be more stable.

The nucleic acids may be single stranded or double stranded, as specified, or contain portions of both double stranded or single stranded sequence. As will be appreciated by those in the art, the depiction of a single strand also defines the sequence of the complementary strand; thus the sequences described herein also provide the complement of the sequence. The nucleic acid may be DNA, both genomic and cDNA, RNA or a hybrid, where the nucleic acid may contain combinations of deoxyribo- and ribo-nucleotides, and combinations of bases, including uracil, adenine, thymine, cytosine, guanine, inosine, xanthine hypoxanthine, isocytosine, isoguanine, etc. "Transcript" typically refers to a naturally occurring RNA, e.g., a pre-mRNA, hnRNA, or mRNA. As used herein, the term "nucleoside" includes nucleotides and nucleoside and nucleotide analogs, and modified nucleosides such as amino modified nucleosides. In addition, "nucleoside" includes non-naturally occurring analog structures. Thus, e.g., the individual units of a peptide nucleic acid, each containing a base, are referred to herein as a nucleoside.

A "label" or a "detectable moiety" is a composition detectable by spectroscopic, photochemical, biochemical, immunochemical, chemical, or other physical means. For example, useful labels include $^{32}P$, fluorescent dyes, electron-dense reagents, enzymes (e.g., as commonly used in an ELISA), biotin, digoxigenin, or haptens and proteins or other entities which can be made detectable, e.g., by incorporating a radiolabel into the peptide or used to detect antibodies specifically reactive with the peptide. The labels may be incorporated into the breast cancer nucleic acids, proteins and antibodies at any position. Any method known in the art for conjugating the antibody to the label may be employed, including those methods described by Hunter et al., *Nature* 144:945 (1962); David et al., *Biochemistry* 13:1014 (1974); Pain et al., *J. Immunol. Meth.* 40:219 (1981); and Nygren, *J. Histochem. and Cytochem.* 30:407 (1982).

A "labeled nucleic acid probe or oligonucleotide" is one that is bound, either covalently, through a linker or a chemical bond, or noncovalently, through ionic, van der Waals, electrostatic, or hydrogen bonds to a label such that the presence of the probe may be detected by detecting the presence of the label bound to the probe. Alternatively, method using high affinity interactions may achieve the same results where one of a pair of binding partners binds to the other, e.g., biotin, streptavidin.

As used herein a "nucleic acid probe or oligonucleotide" is defined as a nucleic acid capable of binding to a target nucleic acid of complementary sequence through one or more types of chemical bonds, usually through complementary base pairing, usually through hydrogen bond formation. As used herein, a probe may include natural (i.e., A, G, C, or T) or modified bases (7-deazaguanosine, inosine, etc.). In addition, the bases in a probe may be joined by a linkage other than a phosphodiester bond, so long as it does not functionally interfere with hybridization. Thus, e.g., probes may be peptide nucleic acids in which the constituent bases are joined by peptide bonds rather than phosphodiester linkages. It will be understood by one of skill in the art that probes may bind target sequences lacking complete complementarity with the probe sequence depending upon the stringency of the hybridization conditions. The probes are preferably directly labeled as with isotopes, chromophores, lumiphores, chromogens, or indirectly labeled such as with biotin to which a streptavidin complex may later bind. By assaying for the presence or absence of the probe, one can detect the presence or absence of the select sequence or subsequence. Diagnosis or prognosis may be based at the genomic level, or at the level of RNA or protein expression.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, e.g., recombinant cells express genes that are not found within the native (non-recombinant) form of the cell or express native genes that are otherwise abnormally expressed, under expressed or not expressed at all. By the term "recombinant nucleic acid" herein is meant nucleic acid, originally formed in vitro, in general, by the manipulation of nucleic acid, e.g., using polymerases and endonucleases, in a form not normally found in nature. In this manner, operably linkage of different sequences is achieved. Thus an isolated nucleic acid, in a linear form, or an expression vector formed in vitro by ligating DNA molecules that are not normally joined, are both considered recombinant for the purposes of this invention. It is understood that once a recombinant nucleic acid is made and reintroduced into a host cell or organism, it will replicate non-recombinantly, i.e., using the in vivo cellular machinery of the host cell rather than in vitro manipulations; however, such nucleic acids, once produced recombinantly, although subsequently replicated non-recombinantly, are still considered recombinant for the purposes of the invention. Similarly, a "recombinant protein" is a protein made using recombinant techniques, i.e., through the expression of a recombinant nucleic acid as depicted above.

The term "heterologous" when used with reference to portions of a nucleic acid indicates that the nucleic acid comprises two or more subsequences that are not normally found in the same relationship to each other in nature. For instance, the nucleic acid is typically recombinantly produced, having two or more sequences, e.g., from unrelated genes arranged to make a new functional nucleic acid, e.g., a promoter from one source and a coding region from another source. Similarly, a heterologous protein will often refer to two or more subsequences that are not found in the same relationship to each other in nature (e.g., a fusion protein).

A "promoter" is defined as an array of nucleic acid control sequences that direct transcription of a nucleic acid. As used herein, a promoter includes necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription.

A "constitutive" promoter is a promoter that is active under most environmental and developmental conditions. An "inducible" promoter is a promoter that is active under environmental or developmental regulation. The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

An "expression vector" is a nucleic acid construct, generated recombinantly or synthetically, with a series of specified nucleic acid elements that permit transcription of a particular nucleic acid in a host cell. The expression vector can be part of a plasmid, virus, or nucleic acid fragment. Typically, the expression vector includes a nucleic acid to be transcribed operably linked to a promoter.

The phrase "selectively (or specifically) hybridizes to" refers to the binding, duplexing, or hybridizing of a molecule only to a particular nucleotide sequence under stringent hybridization conditions when that sequence is present in a complex mixture (e.g., total cellular or library DNA or RNA).

The phrase "stringent hybridization conditions" refers to conditions under which a probe will hybridize to its target subsequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For selective or specific hybridization, a positive signal is at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C. For PCR, a temperature of about 36° C. is typical for low stringency amplification, although annealing temperatures may vary between about 32° C. and 48° C. depending on primer length. For high stringency PCR amplification, a temperature of about 62° C. is typical, although high stringency annealing temperatures can range from about 50° C. to about 65° C., depending on the primer length and specificity. Typical cycle conditions for both high and low stringency amplifications include a denaturation phase of 90° C.-95° C. for 30 sec-2 min., an annealing phase lasting 30 sec.-2 min., and an extension phase of about 72° C. for 1-2 min. Protocols and guidelines for low and high stringency amplification reactions are provided, e.g., in Innis et al. (1990) *PCR Protocols, A Guide to Methods and Applications*, Academic Press, Inc. N.Y.).

Nucleic acids that do not hybridize to each other under stringent conditions are still substantially identical if the polypeptides which they encode are substantially identical. This occurs, e.g., when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency. Additional guidelines for determining hybridization parameters are provided in numerous reference, e.g., and *Current Protocols in Molecular Biology*, ed. Ausubel et al.

By "determining the functional effect" is meant assaying for a compound that increases or decreases a parameter that is indirectly or directly under the influence of WIF-1, e.g., functional, enzymatic, physical and chemical effects. Such functional effects can be measured by any means known to those skilled in the art, e.g., changes in spectroscopic characteristics (e.g., fluorescence, absorbance, refractive index), hydrodynamic (e.g., shape), chromatographic, or solubility properties for the protein, measuring inducible markers or transcriptional activation of the WIF-1 protein; measuring binding activity, e.g., binding to a Frizzled receptor, measuring cellular proliferation, measuring apoptosis, or the like. Determination of the functional effect of a compound on cancer can also be performed using assays known to those of skill in the art such as an in vitro assays, e.g., cell growth on soft agar; anchorage dependence; contact inhibition and density limitation of growth; cellular proliferation; cellular transformation; growth factor or serum dependence; tumor specific marker levels; invasiveness into Matrigel; tumor growth and metastasis in vivo; mRNA and protein expression in cells undergoing metastasis, and other characteristics of cancer cells. The functional effects can be evaluated by many means known to those skilled in the art, e.g., microscopy for quantitative or qualitative measures of alterations in morphological features, measurement of changes in WIF-1 RNA or protein levels, measurement of RNA stability, identification of downstream or reporter gene expression (CAT, luciferase, β-gal, GFP and the like), e.g., via chemiluminescence, fluorescence, colorimetric reactions, antibody binding, inducible markers, and ligand binding assays. "Functional effects" include in vitro, in vivo, and ex vivo activities.

"Activators" or "modulators" of WIF-1 polynucleotide and polypeptide sequences are used to refer to agents that activate WIF-1. Activators are agents that, e.g., induce or activate the expression of a polypeptide of the invention or bind to, stimulate, increase, open, activate, facilitate, or enhance activation, sensitize or up regulate the activity of a polypeptide of the invention. Activators include nucleic acids that encode WIF-1, demethylating compounds, as well as naturally occurring and synthetic compounds, small chemical molecules and the like. Assays for activators include, e.g., applying candidate compounds to cells expressing WIF-1 and then determining the functional effects. Samples or assays comprising WIF-1 that are treated with a potential activator are compared to control samples without the activator to examine the extent of effect. Control samples (untreated with candidate agents) are assigned a relative activity value of 100%. Activation of the polypeptide is achieved when the polypeptide activity value relative to the control is 110%, optionally 150%, optionally 200%, 300%, 400%, 500%, or 1000-3000% or more higher.

The phrase "changes in cell growth" refers to any change in cell growth and proliferation characteristics in vitro or in vivo, such as formation of foci, anchorage independence, semi-solid or soft agar growth, changes in contact inhibition and density limitation of growth, loss of growth factor or serum requirements, changes in cell morphology, gaining or losing immortalization, gaining or losing tumor specific markers, ability to form or suppress tumors when injected into suitable animal hosts, and/or immortalization of the cell. See, e.g., Freshney, *Culture of Animal Cells a Manual of Basic Technique* pp. 231-241 ($3^{rd}$ ed. 1994).

"Tumor cell" refers to precancerous, cancerous, and normal cells in a tumor.

"Cancer cells," "transformed" cells or "transformation" in tissue culture, refers to spontaneous or induced phenotypic changes that do not necessarily involve the uptake of new genetic material. Although transformation can arise from infection with a transforming virus and incorporation of new genomic DNA, or uptake of exogenous DNA, it can also arise spontaneously or following exposure to a carcinogen, thereby mutating an endogenous gene. Transformation is associated with phenotypic changes, such as immortalization of cells, aberrant growth control, nonmorphological changes, and/or malignancy (see, Freshney, *Culture of Animal Cells a Manual of Basic Technique* (3rd ed. 1994)).

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. Typically, the antigen-binding region of an antibody or its functional equivalent will be most critical in specificity and affinity of binding. See, Paul, *Fundamental Immunology*.

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain (VL) and variable heavy chain (VH) refer to these light and heavy chains respectively.

Antibodies exist, e.g., as intact immunoglobulins or as a number of well-characterized fragments produced by digestion with various peptidases. Thus, e.g., pepsin digests an antibody below the disulfide linkages in the hinge region to produce F(ab)'$_2$, a dimer of Fab which itself is a light chain joined to $V_H$-$C_H$1 by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially Fab with part of the hinge region (see, *Fundamental Immunology* (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., *Nature* 348:552-554 (1990)).

For preparation of antibodies, e.g., recombinant, monoclonal, or polyclonal antibodies, many techniques known in the art can be used (see, e.g., Kohler & Milstein, *Nature* 256:495-497 (1975); Kozbor et al., *Immunology Today* 4:72 (1983); Cole et al., pp. 77-96 in *Monoclonal Antibodies and Cancer Therapy* (1985); Coligan, *Current Protocols in Immunology* (1991); Harlow & Lane, *Antibodies, A Laboratory Manual* (1988); and Goding, *Monoclonal Antibodies: Principles and Practice* (2d ed. 1986)). Techniques for the production of single chain antibodies (U.S. Pat. No. 4,946, 778) can be adapted to produce antibodies to polypeptides of this invention. Also, transgenic mice, or other organisms such as other mammals, may be used to express humanized antibodies. Alternatively, phage display technology can be used to identify antibodies and heteromeric Fab fragments that specifically bind to selected antigens (see, e.g., McCafferty et al., *Nature* 348:552-554 (1990); Marks et al., *Biotechnology* 10:779-783 (1992)).

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity.

As used herein, the phrases "WIF-1 expression is down-regulated" or "WIF-1 is underexpressed" and grammatical equivalents thereof refer to a WIF-1 polypeptide or WIF-1 polynucleotide below a determined reference level. Thus, for example, in accordance with the present invention, a reference level of WIF-1 polypeptide or WIF-1 polynucleotide in a normal or healthy subject is identified as a cut-off value, below which there is a significant correlation between the level of WIF-1 polypeptide or WIF-1 polynucleotide and a cancer. Typically, WIF-1 levels in cancer cells are at least about 2 times, usually at least about 5 times and more usually at least about 10 times lower than a WIF-1 level in a normal cell from the same tissue. The terms "down-regulated" and "underexpressed" are used interchangeably herein. Methods for determining WIF-1 levels are described herein and include, but are not limited to RT-PCR and use of anti-WIF-1 antibodies.

"Correlating the amount" means comparing an amount of a substance, molecule or marker (such as WIF-1) that has been determined in one sample to an amount of the same substance, molecule or marker determined in another sample. The amount of the same substance, molecule or marker determined in another sample may be specific for a given cancer.

Synonyms of the term "determining the amount" are contemplated within the scope of the present invention and include, but are not limited to, detecting, measuring, testing or determining, the presence, absence, amount or concentration of a molecule, such as WIF-1.

II. WIF-1 Polypeptides

The present invention provides novel WIF-1 polypeptides. Full-length WIF-1 polypeptides including a signal peptide sequence (e.g., see SEQ ID NO:2 and GenBank accession numbers described herein), mature full-length WIF-1 polypeptides without a signal peptide (e.g., SEQ ID NO: 14 o3 SEQ ID NO:30) are useful for practicing the methods of this invention and find use as compositions in the pharmaceutical compositions and kits of this invention. In a preferred embodiment, a WIF-1 polypeptide comprises an amino acid sequence that corresponds to about amino acid residues 29-379 of SEQ ID NO:2. This amino acid sequence may have one or more amino acid differences (an addition, substitution or deletion of an amino acid) when compared to amino acid resiodues 29-379 of human Wnt2 (SEQ ID NO:2).

In other aspects of the present invention, a WIF-1 polypeptide comprises a fragment of the full-length WIF-1 polypeptide wherein the fragment comprises a WIF-1 subdomain and wherein the WIF-1 subdomain polypeptide of binds to a Wnt polypeptide and/or inhibits Wnt signaling. Thus, a preferred WIF-1 polypeptide is a WIF-1 subdomain polypeptide that binds to a Wnt polypeptide and/or inhibits Wnt signaling. In a preferred embodiment, this subdomain comprises amino acid residues 1-180 of SEQ ID NO:2. In other preferred embodiments, this domain comprises amino acid residues 1-152 of SEQ ID NO:14, the amino acid sequence of SEQ ID NO:15, the amino acid sequence of SEQ ID NO:16, the amino acid sequence of SEQ ID NO:26, the amino acid sequence of SEQ ID NO:27, the amino acid sequence of SEQ ID NO:28, the amino acid sequence of SEQ ID NO:29, or an amino acid sequence that is at least substantially identical to those sequences and binds to a Wnt polypeptide or inhibits Wnt signaling. In other embodiments, the Wnt-binding domain comprises amino acid residues 29-180 of SEQ ID NO:2, amino acid residues 29-176 of SEQ ID NO:2, or an amino acid sequence that is at least substantially identical to that sequence and binds to a Wnt polypeptide and/or inhibits Wnt signaling. Thus, WIF-1 subdomain polypeptides of the invention may comprise from about 120 to about 180 amino acid residues, and in some embodiments from about 130 to about 150 amino acid residues.

In other preferred embodiments of the present invention, a WIF-1 polypeptide is a fragment of WIF-1 that consists of the Wnt-binding domain of WIF-1. In a preferred embodiment, this subdomain consists of amino acid residues 1-180 of SEQ ID NO:2. In other preferred embodiments, this domain consists of amino acid residues 1-152 of SEQ ID NO:14, the amino acid sequence of SEQ ID NO:15, the amino acid sequence of SEQ ID NO:16, the amino acid sequence of SEQ ID NO:26, the amino acid sequence of SEQ ID NO:27, the amino acid sequence of SEQ ID NO:28, the amino acid sequence of SEQ ID NO:29, or an amino acid sequence that is at least substantially identical to those sequences and binds to a Wnt polypeptide and/or inhibits Wnt signaling. In other embodiments, the Wnt-binding domain consists of amino acid residues 29-180 of SEQ ID NO:2, amino acid residues 29-176 of SEQ ID NO:2, or an amino acid sequence that is at least substantially identical to that sequence and binds to a Wnt polypeptide and/or inhibits Wnt signaling. Thus, WIF-1 subdomain polypeptides of the invention may consist of from about 120 to about 180 amino acid residues, and in some embodiments from about 130 to about 150 amino acid residues.

Preferred fragments of WIF-1 comprise amino acid residues 1 to 152 of SEQ ID NO:14, the amino acid sequence of SEQ ID NO:15, SEQ ID NO:16, SEQ ID NO:26, SEQ ID NO:27, SEQ ID NO:28, SEQ ID NO:29 or an amino acid sequence at least substantially identical to those sequences. This invention also provides functional fragments of these subdomain polypeptides. Thus, also preferred are shorter fragments of amino acid residues 1 to 152 of SEQ ID NO:14, SEQ ID NO:15, SEQ ID NO:16, SEQ ID NO:26, SEQ ID NO:27, SEQ ID NO:28, or SEQ ID NO:29 comprising, for example, about 70 amino acid residues of amino acid residues 1 to 152 of SEQ ID NO:14, SEQ ID NO:15, SEQ ID NO:16, SEQ ID NO:26, SEQ ID NO:27, SEQ ID NO:28, SEQ ID NO:29, about 80 amino acid residues of amino acid residues 1 to 152 of SEQ ID NO:14, SEQ ID NO:15, SEQ ID NO:16, SEQ ID NO:26, SEQ ID NO:27, SEQ ID NO:28, SEQ ID NO:29, about 90 amino acid residues of amino acid residues 1 to 152 of SEQ ID NO:14, SEQ ID NO:15, SEQ ID NO:16, SEQ ID NO:26, SEQ ID NO:27, SEQ ID NO:28, SEQ ID NO:29, about 100 amino acid residues of amino acid residues 1 to 152 of SEQ ID NO:14, SEQ ID NO:15, SEQ ID NO:16, SEQ ID NO:26, SEQ ID NO:27, SEQ ID NO:28, SEQ ID NO:29, about 110 amino acid residues of amino acid residues 1 to 152 of SEQ ID NO:14, SEQ ID NO:15, SEQ ID NO:16, SEQ ID NO:26, SEQ ID NO:27, SEQ ID NO:28, SEQ ID NO:29, about 120 amino acid residues of amino acid residues 1 to 152 of SEQ ID NO:14, SEQ ID NO:15, SEQ ID NO:16, SEQ ID NO:26, SEQ ID NO:27, SEQ ID NO:28, SEQ ID NO:29, about 130 amino acid residues of amino acid residues 1 to 152 of SEQ ID NO:14, SEQ ID NO:15, SEQ ID NO:16, SEQ ID NO:26, SEQ ID NO:27, SEQ ID NO:28, SEQ ID NO:29, or an amino acid sequence at least substantially identical to those sequences and binds a Wnt polypeptide and/or inhibits Wnt signaling.

In another embodiment of the present invention a WIF-1 subdomain polypeptide binding to a Wnt polypeptide and or inhibiting Wnt signaling is a fragment comprising less or equal to 99%, 95%, 90%, 85%, 80%, 75%. 70%, 65%, 60%, 55%, 50%, 45%, 40%, 35%, or 30% of the sequence of the WIF-1 precursor protein shown in SEQ ID NO:2. In another preferred embodiment, a WIF-1 subdomain polypeptide binding to a Wnt polypeptide and or inhibiting Wnt signaling is a fragment comprising less or equal to 99%, 95%, 90%, 85%, 80%, 75%. 70%, 65%, 60%, 55%, 50%, 45%, 40%, 35%, or 30% of the sequence of the WIF-1 precursor protein shown in SEQ ID NO:2 without the signal peptide sequence MARRSAFPAAALWLWSILLCLLALRAEA (SEQ ID NO:20).

In another preferred embodiment, a WIF-1 subdomain polypeptide comprises an amino acid sequence that corresponds to about amino acid residues 1-180 of SEQ ID NO:2, to about amino acid residues 29-180 of SEQ ID NO:2 or to amino acid residues 29-176 of SEQ ID NO:2. These amino acid sequences may have one or more amino acid differences (an addition, substitution or deletion of an amino acid) when compared to amino acid residues 1-180 of SEQ ID NO:2, amino acid residues 29-180 of SEQ ID NO:2 or amino acid residues 29-176 of SEQ ID NO:2.

Preferably, the WIF-1 subdomain polypeptide fragments comprise a contiguous sequence of the sequences listed above. However, as described herein, one or more insertions, substitutions and/or additions of amino acid residues can be performed. Such polypeptides are embraced by the present invention as long as they either bind to a Wnt polypeptide and/inhibit Wnt signaling.

The amino acid residue at position 178 of SEQ ID NO:2 can be either leucine (see, e.g., SEQ ID NO:2 and GenBank Accession Nos. AAD25402 and NP_009122) or glutamine (see, e.g., SEQ ID NOS:14 and 16 and GenBank Accession Nos. Q9Y5W5, AAH18037, AAQ88710).

Figure 20:
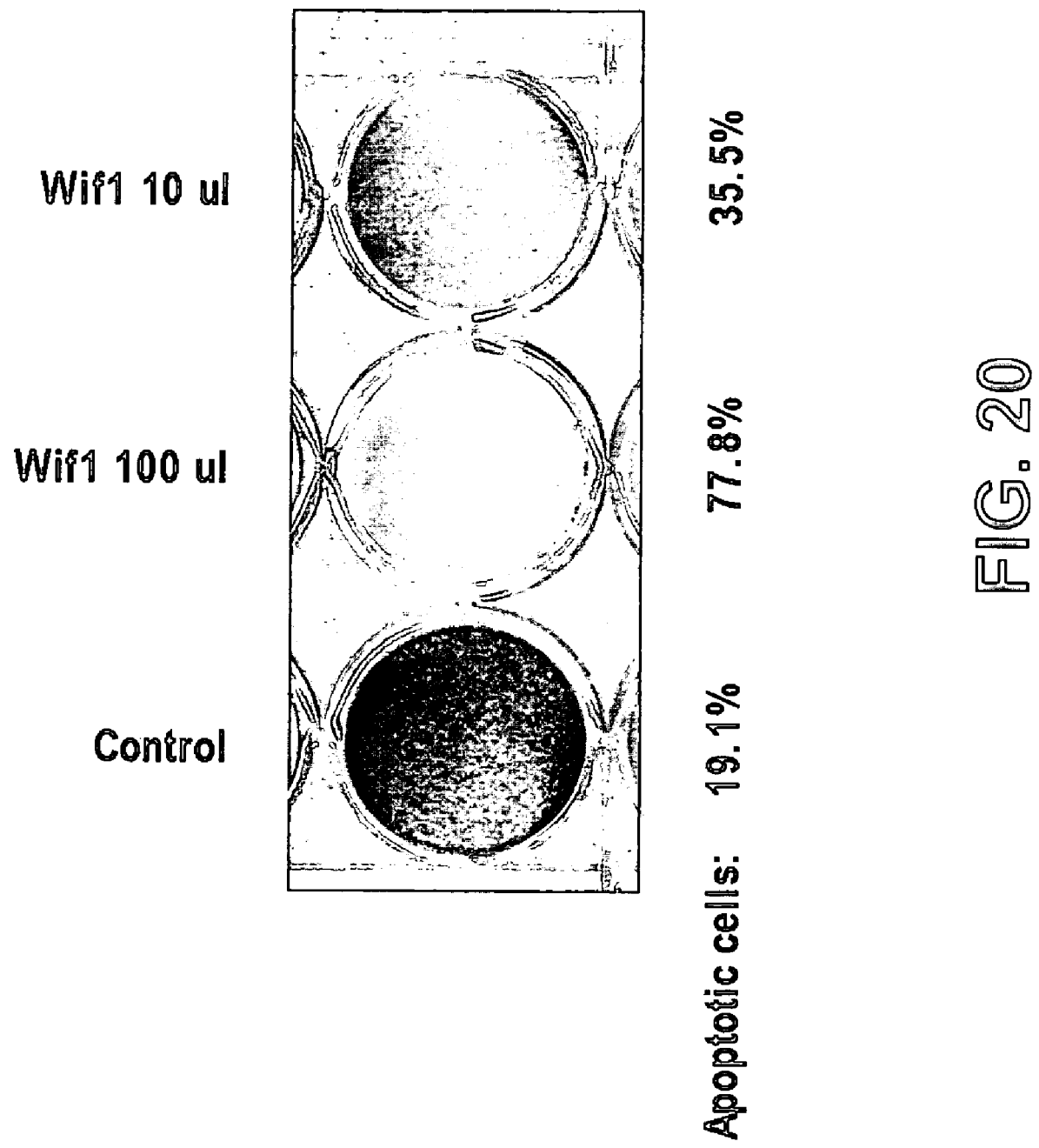
FIG. 20 shows the percentage of apoptotic cells and cytotoxicity effect induced by recombinant full-length human WIF-1 polypeptide (SEQ ID NO:2) in the hepatocellular cancer cell line SNU 398. 10 µl and 100 µl of CM comprising recombinant full-length human WIF-1 polypeptide (SEQ ID NO:2) were added to the cells. Annexin V assay was used to quantitate the apoptotic cells at 5 days after treatment.

Other amino acid substitutions that will still generate a functional WIF-1 subdomain polypeptide will be apparent by the teaching herein, for example by FIG. 20. While amino acid sequences corresponding to WIF-1 subdomain polypeptides are well conserved among such diverse species as human, rat, mouse, *Xenopus* and zebrafish, certain amino acid substitutions, including conservative and non-conservative substitutions are found (FIG. 25). These amino acid substitution seemingly do not interfere with WIF-1 activity. Thus, a human WIF-1 subdomain polypeptide may comprise one or more of the following amino acid substitutions: H43N, V47I, S59A, S86A, S86H, M87V, A94S, A94T, G95D, L104Q, S105T, G112D, A115D, V121M, L123R, T126S, S132T, V134I, L141R, K143N, K143D, D153N, D153T, V154I, I155L, N158D, S159A, E160G, T163P, T163V, T163I, Q166R, or Q169H.

In another preferred embodiment of the present invention, a WIF-1 polypeptide, preferably a WIF-1 subdomain polypeptide is glycosylated. The N-linked amino acid consensus sequence is Asn-X-Ser or Thr, wherein X can be any amino acid residue but not praline. Most O-linked carbohydrate covalent attachments to proteins involve a linkage between the monosaccharide N-acetylgalactosamine and the amino acids serine or threonine. N-linked glycosylation sites, NFT, NCS are found at position 88 of SEQ ID NO:2 and at position 245 of SEQ ID NO:2, respectively. Thus, a full-length WIF-1 polypeptide comprises both N-linked glycosylation sites, whereas a WIF-1 subdomain polypeptide comprises only the NFT glycosylation site. These glycosylation sites are conserved among all WIF-1 species analyzed (see FIG. 25) and point to an important functional feature of WIF-1. A recombinant full-length WIF-1 polypeptide and a recombinant WIF-1 subdomain polypeptide purified from eukaryotic a cell is glycosylated, whereas no glycosylation is found on WIF-1 polypeptides made in bacteria (data not shown). Thus, in a preferred embodiment of the present invention, a WIF-1 polypeptide, and preferably a WIF-1 subdomain polypeptide are produced in a eukaryotic cell. Methods for production of recombinant proteins in eukaryotic cells are described herein.

Thus, in a preferred embodiment of the present invention, a WIF-1 polypeptide is provided that comprises at least two N-linked glycosylation sites. The invention further provides a WIF-1 subdomain polypeptide comprising at least one N-linked glycosylation site. As described herein, glycosylated WIF-1 polypeptides and glycosylated subdomain polypeptides are more potent in inducing apoptosis than their unglycosylated counterparts. Thus, the invention also provides for WIF-1 polypeptides and WIF-1 subdomain polypeptide that comprise at least one additional N-linked glycosylation site. Additional glycosylation sites can be added using in vitro mutagenesis methods as known in the art.

III. Identification of WIF-1 Sequences

In one aspect of the invention, the levels of WIF-1 mRNA or protein are determined in patient samples for which diagnostic or prognostic information is desired. That is, normal tissue (e.g., normal lung, breast or other tissue) may be distinguished from cancerous or metastatic cancerous tissue from the same source; or cancer tissue or metastatic cancerous tissue can be compared with similar tissue samples from other patients, e.g., surviving cancer patients.

A. General Recombinant DNA Methods

This aspect of the invention relies on routine techniques in the field of recombinant genetics. Basic texts disclosing the general methods of use in this invention include Sambrook & Russell, *Molecular Cloning, A Laboratory Manual* (3rd Ed, 2001); Kriegler, *Gene Transfer and Expression: A Laboratory Manual* (1990); and *Current Protocols in Molecular Biology* (Ausubel et al., eds., 1994-1999). Methods that are used to produce WIF-1 for use in the invention may also be employed to produce protein ligands or polypeptides that modulate ligand binding to the receptor, for use in the invention.

For nucleic acids, sizes are given in either kilobases (kb) or base pairs (bp). These are estimates derived from agarose or acrylamide gel electrophoresis, from sequenced nucleic acids, or from published DNA sequences. For proteins, sizes are given in kilodaltons (kDa) or amino acid residue numbers. Proteins sizes are estimated from gel electrophoresis, from sequenced proteins, from derived amino acid sequences, or from published protein sequences.

Oligonucleotides that are not commercially available can be chemically synthesized according to the solid phase phosphoramidite triester method first described by Beaucage & Caruthers, *Tetrahedron Letts.* 22:1859-1862 (1981), using an automated synthesizer, as described in Van Devanter et. al., *Nucleic Acids Res.* 12:6159-6168 (1984). Purification of oligonucleotides is by either native acrylamide gel electrophoresis or by anion-exchange HPLC as described in Pearson & Reanier, *J. Chrom.* 255:137-149 (1983).

The sequence of the cloned genes and synthetic oligonucleotides can be verified after cloning using, e.g., the chain termination method for sequencing double-stranded templates of Wallace et al., *Gene* 16:21-26 (1981).

1. Cloning Methods for the Isolation of Nucleotide Sequences

In general, nucleic acid sequences encoding WIF-1 and related nucleic acid sequence homologs are cloned from cDNA and genomic DNA libraries by hybridization with a probe, or isolated using amplification techniques with oligonucleotide primers. For example, sequences are typically isolated from mammalian nucleic acid (genomic or cDNA) libraries by hybridizing with a nucleic acid probe, the sequence of which can be derived from SEQ ID NO:1.

Amplification techniques using primers can also be used to amplify and isolate nucleic acids from DNA or RNA (see, e.g., section "detection of polynucleotides", below). Suitable primers for amplification of specific sequences can be designed using principles well known in the art (see, e.g., Dieffenbach & Dveksler, *PCR Primer: A Laboratory Manual* (1995)). These primers can be used, e.g., to amplify either the full length sequence or a probe, typically varying in size from ten to several hundred nucleotides, which is then used to identify WIF-1 polynucleotides.

Nucleic acids encoding WIF-1 can also be isolated from expression libraries using antibodies as probes. Such polyclonal or monoclonal antibodies can be raised using the sequence of SEQ ID NO:2.

Synthetic oligonucleotides can also be used to construct WIF-1 genes for use as probes or for expression of protein. This method is performed using a series of overlapping oligonucleotides usually 40-120 bp in length, representing both the sense and nonsense strands of the gene. These DNA fragments are then annealed, ligated and cloned. Alternatively, amplification techniques can be used with precise primers to amplify a specific subsequence of the nucleic acid. The specific subsequence is then ligated into an expression vector.

The nucleic acid encoding WIF-1 is typically cloned into intermediate vectors before transformation into prokaryotic or eukaryotic cells for replication and/or expression. These intermediate vectors are typically prokaryote vectors, e.g., plasmids, or shuttle vectors.

Optionally, nucleic acids encoding chimeric proteins comprising WIF-1 or domains thereof can be made according to standard techniques. For example, a domain such as ligand binding domain can be covalently linked to a heterologous protein., e.g., green fluorescent protein, luciferase, or β-galactosidase.

2. Expression in Prokaryotes and Eukaryotes

To obtain high level expression of a WIF-1 nucleic acid, one typically subclones a WIF-1 nucleic acid into an expression vector that contains a strong promoter to direct transcription, a transcription/translation terminator, and if for a nucleic acid encoding a protein, a ribosome binding site for translational initiation. Suitable bacterial promoters are well known in the art and described, e.g., in Sambrook & Russell, supra, Ausubel et al., supra. Bacterial expression systems for expressing the WIF-1 protein are available in, e.g., *E. coli, Bacillus* sp., and *Salmonella* (Palva et al., *Gene* 22:229-235 (1983); Mosbach et al., *Nature* 302:543-545 (1983). Kits for such expression systems are commercially available. Eukaryotic expression systems for mammalian cells, yeast, and insect cells are well known in the art and are also commercially available. In one embodiment, the eukaryotic expression vector is an adenoviral vector, an adeno-associated vector, or a retroviral vector.

The promoter used to direct expression of a heterologous nucleic acid depends on the particular application. The promoter is optionally positioned about the same distance from the heterologous transcription start site as it is from the transcription start site in its natural setting. As is known in the art, however, some variation in this distance can be accommodated without loss of promoter function.

In addition to the promoter, the expression vector typically contains a transcription unit or expression cassette that contains all the additional elements required for the expression of the WIF-1-encoding nucleic acid in host cells. A typical expression cassette thus contains a promoter operably linked to the nucleic acid sequence encoding WIF-1 and signals required for efficient polyadenylation of the transcript, ribosome binding sites, and translation termination. The nucleic acid sequence encoding WIF-1 may typically be linked to a cleavable signal peptide sequence to promote secretion of the encoded protein by the transformed cell. Such signal peptides would include, among others, the signal peptides from tissue plasminogen activator, insulin, and neuron growth factor, and juvenile hormone esterase of *Heliothis virescens*. Additional elements of the cassette may include enhancers and, if genomic DNA is used as the structural gene, introns with functional splice donor and acceptor sites.

In addition to a promoter sequence, the expression cassette should also contain a transcription termination region downstream of the structural gene to provide for efficient termination. The termination region may be obtained from the same gene as the promoter sequence or may be obtained from different genes.

The particular expression vector used to transport the genetic information into the cell is not particularly critical. Any of the conventional vectors used for expression in eukaryotic or prokaryotic cells may be used. Standard bacterial expression vectors include plasmids such as pBR322 based plasmids, pSKF, pET23D, and fusion expression systems such as GST and LacZ. Epitope tags can also be added to recombinant proteins to provide convenient methods of isolation, e.g., c-myc.

Expression vectors containing regulatory elements from eukaryotic viruses are typically used in eukaryotic expression vectors, e.g., SV40 vectors, papilloma virus vectors, and vectors derived from Epstein-Barr virus. Other exemplary eukaryotic vectors include pMSG, pAV009/A+, pMTO10/A+, pMAMneo-5, baculovirus pDSVE, and any other vector allowing expression of proteins under the direction of the SV40 early promoter, SV40 later promoter, metallothionein promoter, murine mammary tumor virus promoter, Rous sarcoma virus promoter, polyhedrin promoter, or other promoters shown effective for expression in eukaryotic cells.

Some expression systems have markers that provide gene amplification such as thymidine kinase, hygromycin B phosphotransferase, and dihydrofolate reductase. Alternatively, high yield expression systems not involving gene amplification are also suitable, such as using a baculovirus vector in insect cells, with a WIF-1-encoding sequence under the direction of the polyhedrin promoter or other strong baculovirus promoters.

The elements that are typically included in expression vectors also include a replicon that functions in *E. coli*, a gene encoding antibiotic resistance to permit selection of bacteria that harbor recombinant plasmids, and unique restriction sites in nonessential regions of the plasmid to allow insertion of eukaryotic sequences. The particular antibiotic resistance gene chosen is not critical, any of the many resistance genes known in the art are suitable. The prokaryotic sequences are optionally chosen such that they do not interfere with the replication of the DNA in eukaryotic cells, if necessary.

Standard transfection methods are used to produce bacterial, mammalian, yeast or insect cell lines that express large quantities of WIF-1 protein, which are then purified using standard techniques (see, e.g., Colley et al., *J. Biol. Chem.* 264:17619-17622 (1989); *Guide to Protein Purification, in Methods in Enzymology*, vol. 182 (Deutscher, ed., 1990)). Transformation of eukaryotic and prokaryotic cells are performed according to standard techniques (see, e.g., Morrison, *J. Bact.* 132:349-351 (1977); Clark-Curtiss & Curtiss, *Methods in Enzymology* 101:347-362 (Wu et al., eds, 1983).

Any of the well known procedures for introducing foreign nucleotide sequences into host cells may be used. These include the use of calcium phosphate transfection, polybrene, protoplast fusion, electroporation, liposomes, microinjection, plasma vectors, viral vectors and any of the other well known methods for introducing cloned genomic DNA, cDNA, synthetic DNA or other foreign genetic material into a host cell (see, e.g., Sambrook and Russell., supra). It is only necessary that the particular genetic engineering procedure used be capable of successfully introducing at least one gene into the host cell capable of expressing WIF-1.

After the expression vector is introduced into the cells, the transfected cells are cultured under conditions favoring expression of WIF-1, which is recovered from the culture using standard techniques (see, e.g., Scopes, *Protein Purification: Principles and Practice* (1982); U.S. Pat. No. 4,673,641; Ausubel et al., supra; and Sambrook et al., supra).

IV. Detection of WIF-1 Polynucleotides and Polypeptides

A. Detecting Cancer Cells in a Subject

WIF-1 polypeptides of the present invention find use in a variety of ways. In a preferred embodiment of this invention a method of detecting a cancer cell in a subject is provided. This method comprises the steps of providing a biological sample from the subject, wherein the biological sample comprises a cell suspected of being a cancer cell and detecting the level of WIF-1 expression in the cell. Optionally, this method comprises comparing the level of WIF-1 expression in the cell with the level of WIF-1 expression in a cell from one or more healthy subjects or with a previously determined reference range for a level of WIF-1 expression. In one embodiment of the invention, detecting the level of WIF-1 expression is carried out by detecting the level of WIF-1 mRNA. In another embodiment of the invention, detecting the level of WIF-1 expression is carried out by detecting the level of a WIF-1 polypeptide. Agents for use in this method, such as anti-WIF-1 antibodies are disclosed herein.

Detection of the level of WIF-1 expression may be determined for a variety of reasons. Detecting the level of WIF-1 expression may be (i) part of screening, diagnosis or prognosis of cancer in the subject; (ii) part of determining susceptibility of the subject to cancer; (iii) part of determining the stage or severity of a cancer in the subject; (iv) part of identifying a risk for the subject of developing a cancer; or (v) part of monitoring the effect of an anti-cancer drug or therapy administered to the subject diagnosed with cancer. The anti-cancer drug or therapy administered to the subject may comprise a WIF-1 polypeptide, preferably a WIF-1 subdomain polypeptide of this invention.

B. Identification of Subjects at Risk of Developing Cancer and Identifying in a Subject the Stage or Severity of a Cancer In a preferred embodiment of this invention a method for identifying a subject at risk of developing cancer or for identifying in a subject the stage or severity of a cancer, is provided. As shown herein, WIF-1 expression is down-regulated in various cancer cells (FIG. 2). As further shown herein, a WIF-1 polypeptide, in particular a recombinant WIF-1 polypeptide induces in a cancer cells in a dose-dependent manner (FIGS. 10-15). Thus, amounts of WIF-1 are characteristic of various cancer risk states, e.g., high, medium or low. The risk of developing cancer may be determined by measuring WIF-1 and then either submitting the measurements to a classification algorithm or comparing them with a reference amount and/or pattern of WIF-1 that is associated with a particular risk level or with a particular stage or severity of a cancer.

Using the methods of the invention, WIF-1 levels are determined in a biological sample from a subject for whom a risk of developing cancer is to be determined. A WIF-1 level detected in a biological sample from the subject for whom a risk of developing prostate cancer is to be determined that is lower than the WIF-1 level detected in a comparable biological sample from normal or healthy subjects or lower than a predetermined base level, indicates that the subject for whom a risk of developing cancer is to be determined has a risk of developing cancer.

C. Screening, Diagnosis or Prognosis of Cancer in a Subject

In another preferred embodiment of the present invention, a cancer in a subject is determined as part of screening, diagnosis or prognosis of the cancer in the subject. Using the methods of the invention, WIF-1 levels are determined in a biological sample from a subject to be screened for cancer. A WIF-1 level detected in a biological sample from the subject to be screened for cancer that is lower than the WIF-1 level detected in a comparable biological sample from normal or healthy subjects or lower than a predetermined base level, indicates that the subject screened for cancer has or is likely to have cancer.

D. Detection of Hypermethylated Sequences

In one aspect, the invention provides methods of detecting a cancer cell. Preferably detection of cancer is in a subject, more preferably in a mammal and most preferably in a human. Using the compositions and methods described herein, detection of cancer can be done in a variety of ways. In one embodiment, a cancer is detected using a method for detecting a hypermethylated WIF-1 promoter.

In one embodiment, a cancer cell, e.g., a lung cancer or breast cancer cell, is detected by detecting the presence of hypermethylation of a WIF-1 regulatory element, such as the WIF-1 promoter. In some aspects of the present invention, hypermethylation of a polynucleotide sequence contained within a WIF-1 regulatory element is detected. Preferred polynucleotide sequences contained within a WIF-1 regulatory element comprise a CpG island.

In a preferred embodiment of the present invention, a method for detecting a hypermethylated WIF-1 promoter is provided. A hypermethylated WIF-1 promoter can be detected using any technique known in the art, e.g., bisulfite sequences, methylation-specific PCR, or using methylation-sensitive restriction enzymes. In a preferred embodiment of this invention, the method comprises the step of contacting the hypermethylated WIF-1 promoter with an oligonucleotide comprising a sequence that specifically hybridizes to the hypermethylated WIF-1 promoter in an amount effective to detect the hypermethylated WIF-1 promoter. Oligonucleotides useful to practice this invention are described herein. This method optionally comprises the step of determining the amount of methylation of a WIF-1 promoter and compare it to a normal sample.

Detection of a hypermethylated WIF-1 promoter may be performed in a biological sample from a subject, such as a patient. Detecting an increase in the amount of methylation in the sample relative to normal, indicates the presence of cancer in the patient.

As discussed above, hypermethylation of cysteine residues in the promoter region is an indicator of underexpression of WIF-1. The degree of methylation can be detected using a variety of methods. For example, methylation analysis can be performed using Southern hybridization, which assesses methylation-sensitive restriction sites within CpG islands of the WIF-1 promoter. Any restriction endonuclease that includes CG as part of its recognition site and that is inhibited when the C is methylated, can be utilized for this analysis. Methylation sensitive restriction endonucleases include AciI, BsiEI, BssHII, BstUI, Eag I, FauI, HaeII, HpaI, HpaII, MspI, NarI, NotI, SacII, or SmaI. These enzymes may be used alone or in combination.

More sensitive assays for mapping DNA methylation patterns are also available. These include bisulfite DNA sequencing and methylation-specific PCR. These techniques allow analysis of multiple CpG dinucleotides across a single CpG island of interest. Bisulfite DNA sequencing is based on bisulfite-induced modification of genomic DNA under conditions whereby unmethylated cytosine is converted to uracil. The bisulfite-modified sequence is then amplified by PCR with two sets of strand-specific primers to yield a pair of fragments, one from each strand, in which all uracil and thymine residues are amplified as thymine and only 5-methylcytosine residues are amplified as cytosine. The PCR products can be sequenced directly or can be cloned and sequenced to provide methylation maps of single DNA molecules (see, e.g., Frommer, et al., *Proc. Natl. Acad. Sci.* 89:1827-1831 (1992)).

Methylation-specific PCR can also be used to assess the methylation status of CpG dinucleotide sites within a CpG island, independent of the use of methylation-sensitive restriction enzymes. This assay involves the initial modification of DNA by sodium bisulfite, or another comparable agents, to convert unmethylated, but not methylated, cytosines to uracils. Subsequent amplification with primers specific for methylated DNA, or unmethylated DNA, results in the amplification of DNA consisting of methylated CpG dinucleotides. The primers specifically distinguish between u methylated and non-methylated DNA. To accomplish this, primer sequences are typically chosen for regions containing frequent cytosines (to distinguish unmodified from modified DNA), and CpG pairs near the 3' end of the primers (to provide maximal discrimination in the PCR reaction between methylated and unmethylated DNA). Since the two strands of DNA are no longer complementary after bisulfite treatment, primers can be designed for either modified strand. For example, primers specific for the methylated DNA typically have a T in the 3'CG pair to distinguish it from the C retained in methylated DNA, and the complement is designed for the antisense primer. See, U.S. Pat. No. 5,786,146; Herman et al., *Proc. Natl. Acad. Sci. USA* 93:9821-9826 (1996).

Exemplary set of primers for amplifying methylated and un-methylated DNA sequences within the WIF-1 promoter region include, for example, the methylation-specific primers: 5'-GGGCGTTTTATTGGGCGTAT-3' (forward) (SEQ ID NO: 4) and 5'-AAACCAACAATCAACGAAC-3' (reverse) (SEQ ID NO: 5) and the unmethylation-specific primers: 5'-GGGTGTTTTATTGGGTGTAT-3' (forward) (SEQ ID NO: 6) and 5'-AAACCAACAATCAACAAAAC-3' (reverse) (SEQ ID NO: 7) corresponding to the WIF-1 promoter region sequences −488 to −468 and −310 to −290, respectively (see Examples).

In one aspect, methylated WIF-1 promoter sequences are detected by mass spectrometry as further described herein. Particularly useful is the method described by Bane et al. (*Nucleic Acids Res.* 30(14):e69 (2002); incorporated herewith by reference in its entirety). Bane et al. describe the use of SELDI-TOF mass spectrometry to analyze methylated and unmethylated promoter-containing DNA fragments.

Another preferred mass spectrometric technique for use in the present invention is MALDI-TOF MS (Matrix-Assisted Laser Desorption/Ionization Time-of-Flight Mass Spectrometry). MALDI-TOF MS is a recent improvement of mass spectrometry. The molecule to be analyzed is mixed with a matrix that does not ionize, but aids in the ionization of large molecules, such as a DNA molecule. For example, the matrix can be an ultraviolet radiation-absorbing material that is mixed with the DNA molecules. MALDI-TOF MS can be applied to analyzing DNA molecules of various sizes. Time-of-flight allows for high throughput of ions. Samples can be analyzed in a couple of seconds using this procedure. Exemplary MALDI-TOF technologies are described in, for example, U.S. Pat. Appls. Nos. 2001/0033809, 2003/0010908, 2003/0164449, and 2004/0050787, Humeny et al., *Anal. Biochem.* 313(1):160-166 (2003), Schatz et al., *Nucleic Acids Res.* 32(21):e167 (2004) and Rakyan et al., *PLos Biol.* 2(12):e405 (2004); all of which are incorporated herewith by reference in their entirety. MALDI-TOF can also be applied to DNA sequencing of the DNA molecules (See, for example, Taranenko et al., *Nucleic Acids Res.* 26(10):2488-2490 (1998); Edwards et al., *Nucleic Acids Res.* 29(21):e104 (2001)). Thus, also contemplated herein are methods and reagents for sequencing by mass spectrometry of a PCR product generated as described herein.

E. Detection of WIF-1 mRNA

In one embodiment, the method of detecting cancer comprises determining the level of a transcript encoding WIF-1 (see e.g., Genbank accession NM 007191 and SEQ ID NO: 1) in a biological sample from a subject, such as a patient. Detecting a decrease in the level of the WIF-1 mRNA relative to normal indicates the presence of cancer in the subject. In one embodiment, the step of determining the level of the WIF-1 mRNA comprises an amplification reaction. In another embodiment, the presence of cancer is evaluated by determining in a cell the level of expression of mRNA encoding WIF-1. A WIF-1 mRNA level lower than in a corresponding non-cancerous tissue indicates the presence of cancer. Methods of evaluating RNA expression of a particular gene are well known to those of skill in the art, and include, inter alia, hybridization and amplification based assays.

1. Direct Hybridization-based Assays

Methods of detecting and/or quantifying the level of WIF-1 gene transcripts (mRNA or cDNA made therefrom) using nucleic acid hybridization techniques are known to those of skill in the art. For example, one method for evaluating the presence, absence, or quantity of WIF-1 polynucleotides involves a Northern blot. Gene expression levels can also be analyzed by techniques known in the art, e.g., dot blotting, in situ hybridization, RNase protection, probing DNA microchip arrays, and the like.

2. Amplification-based Assays

In another embodiment, amplification-based assays are used to measure the expression level of WIF-1. In such an assay, the WIF-1 nucleic acid sequences act as a template in an amplification reaction (e.g., Polymerase Chain Reaction, or PCR). In a quantitative amplification, the amount of amplification product will be proportional to the amount of template in the original sample. Comparison to appropriate controls provides a measure of the level of WIF-1 in the sample. Methods of quantitative amplification are well known to those of skill in the art. Detailed protocols for quantitative PCR are provided, e.g., in Innis et al. (1990) *PCR Protocols, A Guide to Methods and Applications*, Academic Press, Inc. N.Y.). The known nucleic acid sequences for WIF-1 (see, e.g., SEQ ID NO:1) is sufficient to enable one of skill to routinely select primers to amplify any portion of the gene.

In one embodiment, a TaqMan based assay is used to quantify the cancer-associated polynucleotides. TaqMan based assays use a fluorogenic oligonucleotide probe that contains a 5' fluorescent dye and a 3' quenching agent. The probe hybridizes to a PCR product, but cannot itself be extended due to a blocking agent at the 3' end. When the PCR product is amplified in subsequent cycles, the 5' nuclease activity of the polymerase, e.g., AmpliTaq, results in the cleavage of the TaqMan probe. This cleavage separates the 5' fluorescent dye and the 3' quenching agent, thereby resulting in an increase in fluorescence as a function of amplification (see, for example, literature provided by Perkin-Elmer on its web site).

Other suitable amplification methods include, but are not limited to, ligase chain reaction (LCR) (see, Wu and Wallace, *Genomics* 4:560(1989); Landegren et al., *Science* 241:1077 (1988); and Barringer et al., *Gene* 89:117 (1990)), transcription amplification (Kwoh et al., *Proc. Natl. Acad. Sci. USA* 86:1173(1989)), self-sustained sequence replication (Guatelli et al., *Proc. Nat. Acad. Sci. USA* 87: 1874(1990)), dot PCR, and linker adapter PCR, etc.

F. Detection of WIF-1 Polypeptide

In another embodiment, the method of detecting a cancer comprises determining the level of a WIF-1 polypeptide in a biological sample from a subject, such as a patient. Detecting a decrease in the level of the WIF-1 polypeptide relative to normal indicates the presence of cancer in the subject.

Downregulation of WIF-1 expression is indicative of and can be correlated with various cancers. Thus, a WIF-1 polypeptide or a WIF-1 polynucleotide can be used as a biomarker in the diagnosis of cancer. In one preferred embodiment of the present invention, the amount of WIF-1 in a biological sample is determined. Typically, the amount of WIF-1 in a biological sample provided from a normal, healthy or non-cancer subject is correlated with the amount of WIF-1 in a biological sample provided from a cancer subject or from a subject suspected of having cancer. The amount of WIF-1 detected in the biological sample from the cancer subject or from the subject suspected of having cancer may be specific for a given cancer.

Detection of a WIF-1 polypeptide can be accomplished by any specific detection method including, but not limited to, affinity capture, mass spectrometry, traditional immunoassay directed to WIF-1, PAGE, or HPLC as further described herein or as known by one skilled in the art.

Detection paradigms that can be employed to this end include optical methods, electrochemical methods (voltametry and amperometry techniques), atomic force microscopy, and radio frequency methods, e.g., multipolar resonance spectroscopy. Illustrative of optical methods, in addition to microscopy, both confocal and non-confocal, are detection of fluorescence, luminescence, chemiluminescence, absorbance, reflectance, transmittance, and birefringence or refractive index (e.g., surface plasmon resonance, ellipsometry, a resonant mirror method, a grating coupler waveguide method or interferometry).

1. Detection by Mass Spectrometry

In a preferred embodiment of the present invention, a WIF-1 polypeptide is detected by mass spectrometry, a method that employs a mass spectrometer to detect gas phase ions. In general, mass spectrometry involves the ionization or vaporization of a molecule, accelerating the ions in an electric field, and passing the ions through a magnetic field. The ions are separated according to their mass as they pass through a magnetic field and are then directed into a detector for identification and analysis. Mass spectrometry data can be collected in less than one minute per sample.

A preferred mass spectrometric technique for use in the present invention is surface-enhanced laser desorption/ionization (SELDI). "SELDI" is a method of gas phase ion spectrometry in which the surface of substrate which presents an analyte, such as a WIF-1 polypeptide, to the energy source plays an active role in the desorption and ionization process. The SELDI technology is described in, e.g., U.S. Pat. No. 5,719,060, which is incorporated herewith by reference in its entirety. Other mass spectrometry methods suitable for detecting a WIF-1 polypeptide and WIF-1 polynucleotide are described in U.S. Pat. Nos. 5,894,063, 6,020,208, 6,027,942, 6,528,320, U.S. Pat. Appls. Nos. 2003/0091976 and 2002/0060290, all of which are incorporated herewith by reference in their entirety.

Another preferred mass spectrometric technique for the detection of WIF-1 polypeptide is MALDI-TOF MS as described above. Other preferred mass spectrometric techniques for use in the present invention are LC-ESI MS (Liquid Chromatography-Electrospray Ionization Tandem Mass Spectrometry) as, for example, described by Song et al. (*Anal. Chem.* 77(2):504-510 (2005)).

Typically, an analyte, such as a WIF-1 polypeptide or a WIF-1 polynucleotide (e.g., a PCR product), to be analyzed by mass spectrometry, is attached to a probe on which it is presented to an ionization source. A probe (e.g., a biochip) is optionally formed in any suitable shape (e.g., a square, a rectangle, a circle, or the like) as long as it is adapted for use with a gas phase ion spectrometer (e.g., removably insertable into a gas phase ion spectrometer). For example, the probe can be in the form of a strip, a plate, or a dish with a series of wells at predetermined addressable locations or have other surfaces features. The probe is also optionally shaped for use with inlet systems and detectors of a gas phase ion spectrometer. For example, the probe can be adapted for mounting in a horizontally, vertically and/or rotationally translatable carriage that horizontally, vertically and/or rotationally moves the probe to a successive position without requiring repositioning of the probe by hand.

In certain embodiments, the probe substrate surface can be conditioned to bind analytes. For example, the surface of the probe substrate can be conditioned (e.g., chemically or mechanically such as roughening) to place adsorbents on the surface. The adsorbent comprises functional groups for binding with an analyte, such as a WIF-1 polypeptide. In some embodiments, the substrate material itself can also contribute to adsorbent properties and may be considered part of an adsorbent (See, e.g., U.S. Pat. Appl. No. 2003/0091976).

Adsorbents can be placed on the probe substrate in continuous or discontinuous patterns. If continuous, one or more adsorbents can be placed on the substrate surface. If multiple types of adsorbents are used, the substrate surface can be coated such that one or more binding characteristics vary in a one- or two-dimensional gradient. If discontinuous, plural adsorbents can be placed in predetermined addressable locations or surface features (e.g., addressable by a laser beam of a mass spectrometer) on the substrate surface. The surface features of probes or biochips include various embodiments. For example, a biochip optionally includes a plurality of surface features arranged in, e.g., a line, an orthogonal array, a circle, or an n-sided polygon, wherein n is three or greater. The plurality of surface features typically includes a logical or spatial array. Optionally, each of the plurality of surface features comprises identical or different adsorbents, or one or more combinations thereof. For example, at least two of the plurality of surface features optionally includes identical or different adsorbents, or one or more combinations thereof. Suitable adsorbents are described in, for example, U.S. Pat. Appl. No. 2003/0091976.

The probe substrate can be made of any suitable material. Probe substrates are preferably made of materials that are capable of supporting adsorbents. For example, the probe substrate material can include, but is not limited to, insulating materials (e.g., plastic, ceramic, glass, or the like), a magnetic material, semi-conducting materials (e.g., silicon wafers), or electrically conducting materials (e.g., metals, such as nickel, brass, steel, aluminum, gold, metalloids, alloys or electrically conductive polymers), polymers, organic polymers, conductive polymers, biopolymers, native biopolymers, metal coated with organic polymers, synthetic polymers, composite materials or any combinations thereof. The probe substrate material is also optionally solid or porous.

Probes are optionally produced using any suitable method depending on the selection of substrate materials and/or adsorbents. For example, the surface of a metal substrate can be coated with a material that allows derivatization of the metal surface. More specifically, a metal surface can be coated with silicon oxide, titanium oxide, or gold. Then, the surface can be derivatized with a bifunctional linker, one end of which can covalently bind with a functional group on the surface and the other end of which can be further derivatized with groups that function as an adsorbent. In another example, a porous silicon surface generated from crystalline silicon can be chemically modified to include adsorbents for binding analytes. In yet another example, adsorbents with a hydrogel backbone can be formed directly on the substrate surface by in situ polymerizing a monomer solution that includes, e.g., substituted acrylamide monomers, substituted acrylate monomers, or derivatives thereof comprising a selected functional group as an adsorbent. Probes suitable for use in the present invention are described in, e.g., U.S. Pat. Nos. 5,617,060, 5,894,063, 6,020,208, 6,027,942, 6,528,320, WO 98/59360 and U.S. Pat. Appls. Nos. 2003/0091976 and 2002/0060290, all of which are incorporated herewith by reference in their entirety.

2. Production of Antibodies and Immunological Detection of WIF-1

Antibodies can also be used to detect WIF-1. Antibodies to WIF-1 are commercially available (e.g., Santa Cruz Biotechnology) or can be produced using well known techniques (see, e.g., Harlow & Lane, *Antibodies: A Laboratory Manual* (1988) and Harlow & Lane, *Using Antibodies* (1999); Coligan, *Current Protocols in Immunology* (1991); Goding, *Monoclonal Antibodies: Principles and Practice* (2d ed. 1986); and Kohler & Milstein, *Nature* 256:495-497 (1975)). Such techniques include antibody preparation by selection of antibodies from libraries of recombinant antibodies in phage or similar vectors, as well as preparation of polyclonal and monoclonal antibodies by immunizing rabbits or mice (see, e.g., Huse et al., *Science* 246:1275-1281 (1989); Ward et al., *Nature* 341:544-546 (1989)). Such antibodies are typically used for diagnostic or prognostic applications, e.g., in the detection of lung or breast cancer.

WIF-1 or a fragment thereof may be used to produce antibodies specifically reactive with WIF-1. For example, a recombinant WIF-1 or an antigenic fragment thereof, is isolated as described herein. Recombinant protein is the preferred immunogen for the production of monoclonal or polyclonal antibodies. Alternatively, a synthetic peptide derived from the sequences disclosed herein and conjugated to a carrier protein can be used as an immunogen. Naturally occurring protein may also be used either in pure or impure form. The product is then injected into an animal capable of producing antibodies. Either monoclonal or polyclonal antibodies may be generated, for subsequent use in immunoassays to measure the protein.

Typically, polyclonal antisera with a titer of $10^4$ or greater are selected and tested for their cross reactivity against non-WIF-1 proteins or even other related proteins from other organisms, using a competitive binding immunoassay. Specific polyclonal antisera and monoclonal antibodies will usually bind with a $K_d$ of at least about 0.1 mM, more usually at least about 1 µM, optionally at least about 0.1 µM or better, and optionally 0.01 µM or better. For cross-reactivity determination, typically immunoabsorbed antisera are used in a competitive binding immunoassay to compare a second protein to the WIF-1 protein. In order to make this comparison, the two proteins are each assayed at a wide range of concentrations and the amount of each protein required to inhibit 50% of the binding of the antisera to the immobilized protein is determined. If the amount of the second protein required to inhibit 50% of binding is less than 10 times the amount of the antigenic WIF-1 protein that is required to inhibit 50% of binding, then the second protein is said to specifically bind to the polyclonal antibodies generated to the WIF-1 immunogen.

Once WIF-1-specific antibodies are available, binding interactions with WIF-1 can be detected by a variety of immunoassay methods. For a review of immunological and immunoassay procedures, see, *Basic and Clinical Immunology* (Stites & Terr eds., 7th ed. 1991). Moreover, the immunoassays of the present invention can be performed in any of several configurations, which are reviewed extensively in *Enzyme Immunoassay* (Maggio, ed., 1980); and Harlow & Lane, supra).

Immunoassays also often use a labeling agent to specifically bind to and label the complex formed by the antibody and antigen. The labeling agent may itself be one of the moieties comprising the antibody/antigen complex. Thus, the labeling agent may be a labeled WIF-1 polypeptide or a labeled anti-WIF-1 antibody. Alternatively, the labeling agent may be a third moiety, such as a secondary antibody, that specifically binds to the antibody/antigen complex (a secondary antibody is typically specific to antibodies of the species from which the first antibody is derived). Other proteins capable of specifically binding immunoglobulin constant regions, such as protein A or protein G may also be used as the labeling agent. These proteins exhibit a strong non-immunogenic reactivity with immunoglobulin constant regions from a variety of species (see, e.g., Kronval et al., *J. Immunol.* 111:1401-1406 (1973); Akerstrom et al., *J. Immunol.* 135: 2589-2542 (1985)). The labeling agent can be modified with a detectable moiety, such as biotin, to which another molecule can specifically bind, such as streptavidin. A variety of detectable moieties are well known to those skilled in the art.

Commonly used assays include noncompetitive assays, e.g., sandwich assays, and competitive assays. In competitive assays, the amount of WIF-1 present in the sample is measured indirectly by measuring the amount of a known, added (exogenous) WIF-1 displaced (competed away) from an anti-WIF-1 antibody by the unknown WIF-1 present in a sample. Commonly used assay formats include immunoblots, which are used to detect and quantify the presence of protein in a sample. Other assay formats include liposome immunoassays (LIA), which use liposomes designed to bind specific molecules (e.g., antibodies) and release encapsulated reagents or markers. The released chemicals are then detected according to standard techniques (see, Monroe et al., *Amer. Clin. Prod. Rev.* 5:34-41 (1986)).

The particular label or detectable group used in the assay is not a critical aspect of the invention, as long as it does not significantly interfere with the specific binding of the antibody used in the assay. The detectable group can be any material having a detectable physical or chemical property. Such detectable labels have been well-developed in the field of immunoassays and, in general, most any label useful in such methods can be applied to the present invention. Thus, a label is any composition detectable by spectroscopic, photochemical, biochemical, immunochemical, electrical, optical or chemical means. Useful labels in the present invention include magnetic beads (e.g., DYNABEADS™), fluorescent dyes (e.g., fluorescein isothiocyanate, Texas red, rhodamine, and the like), radiolabels, enzymes (e.g., horse radish peroxidase, alkaline phosphatase and others commonly used in an ELISA), and colorimetric labels such as colloidal gold or colored glass or plastic beads (e.g., polystyrene, polypropylene, latex, etc.).

The label may be coupled directly or indirectly to the desired component of the assay according to methods well known in the art. As indicated above, a wide variety of labels may be used, with the choice of label depending on sensitivity required, ease of conjugation with the compound, stability requirements, available instrumentation, and disposal provisions.

Non-radioactive labels are often attached by indirect means. Generally, a ligand molecule (e.g., biotin) is covalently bound to the molecule. The ligand then binds to another molecule (e.g., streptavidin), which is either inherently detectable or covalently bound to a signal system, such as a detectable enzyme, a fluorescent compound, or a chemiluminescent compound. The ligands and their targets can be used in any suitable combination with antibodies that recognize WIF-1, or secondary antibodies that recognize anti-WIF-1.

The molecules can also be conjugated directly to signal generating compounds, e.g., by conjugation with an enzyme or fluorophore. Enzymes of interest as labels will primarily be hydrolases, particularly phosphatases, esterases and glycosidases, or oxidotases, particularly peroxidases. Fluorescent compounds include fluorescein and its derivatives, rhodamine and its derivatives, dansyl, umbelliferone, etc. Chemiluminescent compounds include luciferin, and 2,3-dihydrophthalazinediones, e.g., luminol. For a review of various labeling or signal producing systems that may be used, see, U.S. Pat. No. 4,391,904.

Means of detecting labels are well known to those of skill in the art. Thus, for example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence. The fluorescence may be detected visually, by means of photographic film, by the use of electronic detectors such as charge coupled devices (CCDs) or photomultipliers and the like. Similarly, enzymatic labels may be detected by providing the appropriate substrates for the enzyme and detecting the resulting reaction product. Finally simple colorimetric labels may be detected simply by observing the color associated with the label. Thus, in various dipstick assays, conjugated gold often appears pink, while various conjugated beads appear the color of the bead.

Some assay formats do not require the use of labeled components. For instance, agglutination assays can be used to detect the presence of the target antibodies. In this case, antigen-coated particles are agglutinated by samples comprising the target antibodies. In this format, none of the components need be labeled and the presence of the target antibody is detected by simple visual inspection.

V. Identification of Activators of WIF-1

Activators of WIF-1, i.e., activators of WIF-1 polypeptide or polynucleotide expression, are useful for treating cancer, e.g., lung cancer or breast cancer. Agents that activate WIF-1 can be tested using a variety of methods. Agents that activate WIF-1 include compounds that activate enhance WIF-1 activity as well as agents that increase WIF-1 expression, including demethylating agents that decrease methylation of the WIF-1 promoter.

The agents tested as activators of WIF-1 can be any small chemical compound, or a biological entity, such as a protein, sugar, nucleic acid or lipid. Typically, test compounds will be small chemical molecules and peptides. Essentially any chemical compound can be used as a potential activator in the assays of the invention, although most often compounds that can be dissolved in aqueous or organic (especially DMSO-based) solutions are used.

A. Large Scale and High Throughput Screening

The assays are designed to screen large chemical libraries by automating the assay steps and providing compounds from any convenient source to assays, which are typically run in parallel (e.g., in microtiter formats on microtiter plates in robotic assays).

In some embodiments, high throughput screening methods involve providing a combinatorial chemical or peptide library containing a large number of potential therapeutic compounds (potential modulator compounds). Such "combinatorial chemical libraries" or "ligand libraries" are then screened in one or more assays, as described herein, to identify those library members (particular chemical species or subclasses) that display a desired characteristic activity. The compounds thus identified can serve as conventional "lead compounds" or can themselves be used as potential or actual therapeutics.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art. Such combinatorial chemical libraries include, but are not limited to, peptide libraries (see, e.g., U.S. Pat. No. 5,010,175, Furka, *Int. J. Pept. Prot. Res.* 37:487-493 (1991) and Houghton et al., *Nature* 354:84-88 (1991)). Other chemistries for generating chemical diversity libraries can also be used. Such chemistries include, but are not limited to: peptoids (e.g., PCT Publication No. WO 91/19735), encoded peptides (e.g., PCT Publication WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., *Proc. Nat. Acad. Sci. USA* 90:6909-6913 (1993)), vinylogous polypeptides (Hagihara et al., *J. Amer. Chem. Soc.* 114:6568 (1992)), nonpeptidal peptidomimetics with glucose scaffolding (Hirschmann et al., *J. Amer. Chem. Soc.* 114:9217-9218 (1992)), analogous organic syntheses of small compound libraries (Chen et al., *J. Amer. Chem. Soc.* 116:2661 (1994)), oligocarbamates (Cho et al., *Science* 261:1303 (1993)), and/or peptidyl phosphonates (Campbell et al., *J. Org. Chem.* 59:658 (1994)), nucleic acid libraries (see, Ausubel et al. (1993); Berger and Sambrook, all supra), peptide nucleic acid libraries (see, e.g., U.S. Pat. No. 5,539,083), antibody libraries (see, e.g., Vaughn et al., *Nature Biotechnology* 14(3):309-314 (1996) and PCT/US96/10287), carbohydrate libraries (see, e.g., Liang et al., *Science* 274: 1520-1522 (1996) and U.S. Pat. No. 5,593,853), small organic molecule libraries (see, e.g., benzodiazepines, Baum C&EN, January 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506, 337; benzodiazepines, U.S. Pat. No. 5,288,514, and the like).

Devices for the preparation of combinatorial libraries are commercially available (see, e.g., 357 MPS, 390 MPS, Advanced Chem Tech, Louisville Ky.; Symphony, Rainin, Woburn, Mass.; 433A Applied Biosystems, Foster City, Calif.; 9050 Plus, Millipore, Bedford, Mass.). In addition, numerous combinatorial libraries are themselves commercially available (see, e.g., ComGenex, Princeton, N.J.; Tripos, Inc., St. Louis, Mo.; 3D Pharmaceuticals, Exton, Pa.; Martek Biosciences, Columbia, Md., etc.).

1. Solid Phase and Soluble High Throughput Assays

In the high throughput assays, it is possible to screen up to several thousand different modulators or ligands in a single day. In particular, each well of a microtiter plate can be used to run a separate assay against a selected potential modulator, or, if concentration or incubation time effects are to be observed, every 5-10 wells can test a single modulator. Thus, a single standard microtiter plate can assay about 100 (e.g., 96) modulators. If 1536 well plates are used, then a single plate can easily assay from about 100 to about 1500 different compounds. It is possible to assay several different plates per day; assay screens for up to about 6,000-20,000 or more different compounds are possible using the integrated systems of the invention. In addition, microfluidic approaches to reagent manipulation can be used.

B. Methods of Screening for Activators of WIF-1

1. WIF-1 Activity

WIF-1 and its alleles and polymorphic variants play a role in inhibiting Wnt signaling. Thus, any of a variety of endpoints can be used to determine WIF-1 activity. These include, but are not limited to, measuring WIF-1 binding to the Frizzled receptor. Further, cell growth and/or apoptosis can also be used to assess WIF-1 activity. Methodology for conducting these assays is well known in the art (see, e.g., Masuhara et al., *Biochem. Biophys. Res. Commun.* 239:439-446 (1997); Minarnoto et al., *Biochem. Biophys. Res. Commun.* 237:79-83, (1997)).

In one embodiment, WIF-1 activity can be determined by measuring cell viability. Cell viability may be assessed by measuring many different endpoints including levels of cytoplasmic enzymes, permeability of cells to dyes, DNA fragmentation, release of a radioisotopic label such as $^{51}Cr$ or other formats. Typically, cell viability is measured using an assay suitable for a high throughput screening format, such as a calorimetric or fluorescent viability assay. For example, an Alamar blue (AB) assay, incorporates a redox indicator that changes the color or fluorescence in response to metabolic activity. The Alamar blue fluoresces in the presence of living, but not dead, cells. Such an assay can be conveniently read in a microplate or by flow cytometry. Colorimetric assays such as the MTT assay, which measures the reduction of MTT (3-(4,5-dimethyl) thiazol-2-yl-2,5-diphenyl tetrazolium bromide) to formazan, may also be used conveniently in a high throughput format to measure cell viability and proliferation.

Other assays that measure cell number may also be used. These include assays that measure intercalation of dyes into the DNA of a cell. The amount of intercalated dye is directly proportional to cell number. For example, cells can be stained with a dye such as Hoechst 33342, which intercalates in the DNA of vital cell, an cell number determined by measuring the amount of fluorescence. Cells may also be directly counted.

Samples or assays that are treated with a potential WIF-1 activator are compared to control samples without the test compound, to examine the extent of modulation. Control samples (untreated with activators) are assigned a relative WIF-1 activity value of 100. Activation of WIF-1 is achieved when the WIF-1 activity value relative to the control is 110%, optionally 150%, 200%, 300%, 400%, 500%, or 1000-2000%.

2. Expression Assays

Screening assays for a compound that increases the expression of WIF-1 are also provided. Screening methods generally involve conducting cell-based assays in which test compounds are contacted with one or more cells capable of expressing WIF-1, and then detecting an increase in WIF-1 expression (either transcript or translation product). Assays can be performed with any cells that express WIF-1.

WIF-1 expression can be detected in a number of different ways. As described infra, the expression level of WIF-1 in a cell can be determined by probing the mRNA expressed in a cell with a probe that specifically hybridizes with a transcript (or complementary nucleic acid derived therefrom) of WIF-1. Probing can be conducted by lysing the cells and conducting Northern blots or without lysing the cells using in situ-hybridization techniques. Alternatively, WIF-1 e protein can be detected using immunological methods in which a cell lysate is probed with antibodies that specifically bind to WIF-1.

Other cell-based assays involve reporter assays conducted with cells using standard reporter gene assays. These assays can be performed in either cells that do, or do not, express WIF-1. Some of these assays are conducted with a heterologous nucleic acid construct that includes a WIF-1 promoter that is operably linked to a reporter gene that encodes a detectable product. A number of different reporter genes can be utilized. Some reporters are inherently detectable. An example of such a reporter is green fluorescent protein that emits fluorescence that can be detected with a fluorescence detector. Other reporters generate a detectable product. Often such reporters are enzymes. Exemplary enzyme reporters include, but are not limited to, CAT (chloramphenicol acetyl transferase; Alton and Vapnek, *Nature* 282:864-869 (1979)), luciferase, ÿ-galactosidase and alkaline phosphatase (Toh et al., *Eur. J. Biochem.* 182:231-238(1980); and Hall et al., *J. Mol. Appl. Gen.* 2:101(1983)).

In these assays, cells harboring the reporter construct are contacted with a test compound. Modulated promoter expression is monitored by detecting the level of a detectable reporter. A number of different kinds of WIF-1 activators can be identified in this assay. For example, a test compound that inhibits the promoter by binding to it, inhibits the promoter by binding to transcription factors or other regulatory factors, binds to their promoter or triggers a cascade that produces a molecule that inhibits the promoter can be identified. Similarly a test compound that, e.g., activates the promoter by binding to it, activates the promoter by binding to transcription factors or other regulatory factors, binds to their promoter or triggers a cascade that produces a molecule that activates the promoter can also be identified.

The level of expression or activity can be compared to a baseline value. The baseline value can be a value for a control sample or a statistical value that is representative of WIF-1 expression levels for a control population (e.g., lean individuals as described herein) or cells (e.g., tissue culture cells not exposed to a WIF-1 modulator). Expression levels can also be determined for cells that do not express WIF-1 as a negative control. Such cells generally are otherwise substantially genetically the same as the test cells.

Various controls can be conducted to ensure that an observed activity is authentic including running parallel reactions with cells that lack the reporter construct or by not contacting a cell harboring the reporter construct with test compound. Compounds can also be further validated as described below.

Compounds can increase expression of WIF-1 by a variety of mechanisms. For example, in one embodiment, compounds may increase expression by decreasing methylation of the WIF-1 promoter. Such compounds include methylation suppressive reagents such as 5-azacytadine and the like, which can be introduced into a cell.

3. Nucleic Acids that Increase WIF-1 Activity

In one aspect of the present invention, WIF-1 activators can also comprise nucleic acid molecules that express WIF-1 or WIF-1 polypeptides such as those comprising the Wnt-binding domain identified here. Conventional viral and non-viral based gene transfer methods can be used to introduce nucleic acids encoding WIF-1 polypeptides in mammalian cells or target tissues. Non-viral vector delivery systems include DNA plasmids, naked nucleic acid, and nucleic acid complexed with a delivery vehicle such as a liposome. Viral vector delivery systems include DNA and RNA viruses, which have either episomal or integrated genomes after delivery to the cell. For a review of gene therapy procedures, see, Anderson, *Science* 256:808-813 (1992); Nabel & Felgner, *TIBTECH* 11:211-217 (1993); Mitani & Caskey, *TIBTECH* 11:162-166 (1993); Dillon, *TIBTECH* 11:167-175 (1993); Miller, *Nature* 357:455-460 (1992); Van Brunt, *Biotechnology* 6(10):1149-1154 (1988); Vigne, *Restorative Neurology and Neuroscience* 8:35-36 (1995); Kremer & Perricaudet, *British Medical Bulletin* 51(1):31-44 (1995); Haddada et al., in *Current Topics in Microbiology and Immunology Doerfler and Boöhm (eds) (*1995); and Yu et al., *Gene Therapy* 1:13-26 (1994).

a) Non-viral Delivery Methods

Methods of non-viral delivery of nucleic acids encoding engineered polypeptides of the invention include lipofection, microinjection, biolistics, virosomes, liposomes, immunoliposomes, polycation or lipid:nucleic acid conjugates, naked DNA, artificial virions, and agent-enhanced uptake of DNA. Lipofection is described in e.g., U.S. Pat. Nos. 5,049,386, 4,946,787; and 4,897,355) and lipofection reagents are sold commercially (e.g., Transfectam™ and Lipofectin™). Cationic and neutral lipids that are suitable for efficient receptor-recognition lipofection of polynucleotides include those of Felgner, WO 91/17424, WO 91/16024. Delivery can be to cells (ex vivo administration) or target tissues (in vivo administration).

The preparation of lipid:nucleic acid complexes, including targeted liposomes such as immunolipid complexes, is well known to one of skill in the art (see, e.g., Crystal, *Science* 270:404-410 (1995); Blaese et al., *Cancer Gene Ther.* 2:291-297 (1995); Behr et al., *Bioconjugate Chem.* 5:382-389 (1994); Remy et al., *Bioconjugate Chem.* 5:647-654 (1994); Gao et al., *Gene Therapy* 2:710-722 (1995); Ahmad et al., *Cancer Res.* 52:4817-4820 (1992); U.S. Pat. Nos. 4,186,183, 4,217,344, 4,235,871, 4,261,975, 4,485,054, 4,501,728, 4,774,085, 4,837,028, and 4,946,787).

b) Viral Delivery Methods

The use of RNA or DNA viral based systems for the delivery of WIF-1 nucleic acids is known in the art. Conventional viral based systems for include retroviral, lentivirus, adenoviral, adeno-associated and herpes simplex virus vectors for gene transfer.

In many gene therapy applications, it is desirable that the gene therapy vector be delivered with a high degree of specificity to a particular tissue type, e.g., lung tissue or breast tissue. A viral vector can be modified to have specificity for a given cell type by expressing a ligand as a fusion protein with a viral coat protein on the viruses outer surface. The ligand is chosen to have affinity for a receptor known to be present on the cell type of interest. For example, Han et al., *Proc Natl. Acad. Sci. U.S.A.* 92:9747-9751 (1995), reported that Moloney murine leukemia virus can be modified to express human heregulin fused to gp70, and the recombinant virus infects certain human breast cancer cells expressing human epidermal growth factor receptor. This principle can be extended to other pairs of virus expressing a ligand fusion protein and target cell expressing a receptor. For example, filamentous phage can be engineered to display antibody fragments (e.g., Fab or Fv) having specific binding affinity for virtually any chosen cellular receptor. Although the above description applies primarily to viral vectors, the same principles can be applied to nonviral vectors. Such vectors can be engineered to contain specific uptake sequences thought to favor uptake by specific target cells.

Gene therapy vectors can be delivered in vivo by administration to an individual patient, typically by systemic administration (e.g., intravenous, intraperitoneal, intramuscular, subdermal, or intracranial infusion) or topical application, as described below. Alternatively, vectors can be delivered to cells ex vivo, such as cells explanted from an individual patient.

Ex vivo cell transfection for diagnostics, research, or for gene therapy (e.g., via re-infusion of the transfected cells into the host organism) is well known to those of skill in the art. In some embodiments, cells are isolated from the subject organism, transfected with WIF-1 nucleic acids and re-infused back into the subject organism (e.g., patient). Various cell types suitable for ex vivo transfection are well known to those of skill in the art (see, e.g., Freshney et al., *Culture of Animal Cells, A Manual of Basic Technique* (3rd ed. 1994)) and the references cited therein for a discussion of how to isolate and culture cells from patients).

Vectors (e.g., retroviruses, adenoviruses, liposomes, etc.) containing therapeutic nucleic acids can also be administered directly to the organism for transduction of cells in vivo. Alternatively, naked DNA can be administered. Administration is by any of the routes normally used for introducing a molecule into ultimate contact with blood or tissue cells. Suitable methods of administering such nucleic acids are available and well known to those of skill in the art, and, although more than one route can be used to administer a particular composition, a particular route can often provide a more immediate and more effective reaction than another route.

Pharmaceutically acceptable carriers are determined in part by the particular composition being administered, as well as by the particular method used to administer the composition. Accordingly, there is a wide variety of suitable formulations of pharmaceutical compositions of the present invention, as described below (see, e.g., *Remington's Pharmaceutical Sciences*, 17th ed., 1989).

VI. Pharmaceutical Compositions

The present invention provides pharmaceutical compositions for treating cancer wherein WIF-1 expression is down-regulated. Such pharmaceutical compositions comprise, for example, a WIF-1 polypeptide, a WIF-1 analog, a WIF-1 mimetic, a WIF-1 related polypeptide; antibodies to the foregoing; a polynucleotide encoding a WIF-1 polypeptide, a WIF-1 analog, a WIF-1 mimetic, a WIF-1 related polypeptide; an activator of WIF-1 expression; or a modulator of WIF-1 activity.

In a preferred embodiment of the present invention, the pharmaceutical composition for treating cancer wherein WIF-1 expression is down-regulated comprises (i) a polynucleotide encoding a WIF-1 polypeptide and (ii) a pharmaceutically acceptable carrier. In a preferred embodiment of the present invention, the polynucleotide encodes the WIF-1 polypeptide of SEQ ID NO:2. In another preferred embodiment of the present invention, the polynucleotide encodes the WIF-1 polypeptide of SEQ ID NO:14. In yet another preferred embodiment of the present invention, the polynucleotide encodes the WIF-1 polypeptide of SEQ ID NO:15. In another preferred embodiment of the present invention, the polynucleotide encodes the WIF-1 polypeptide of SEQ ID NO:16. In a preferred embodiment, the polynucleotide encodes a WIF-1 subdomain polypeptide comprising amino acid residues 1-180 of SEQ ID NO:2, amino acid residues 29-180 of SEQ ID NO:2, amino acid residues 29-176 of SEQ ID NO:2 or amino acid residues 39-176 of SEQ ID NO:2.

In another preferred embodiment of the present invention, the pharmaceutical compositions for treating cancer wherein WIF-1 expression is down-regulated comprises (i) a WIF-1 polypeptide and (ii) a pharmaceutically acceptable carrier. In a preferred embodiment of the invention, the WIF-1 polypeptide comprises the amino acid sequence of SEQ ID NO: 14. In another preferred embodiment of the present invention, the WIF-1 polypeptide comprises the amino acid sequence of SEQ ID NO:15. In yet other embodiments of the present invention, a WIF-1 polypeptide comprises the amino acid sequence of SEQ ID NO:2 or SEQ ID NO:16. In a preferred embodiment, the WIF-1 polypeptide is a WIF-1 subdomain polypeptide comprising amino acid residues 1-180 of SEQ ID NO:2, amino acid residues 29-180 of SEQ ID NO:2, amino acid residues 29-176 of SEQ ID NO:2 or amino acid residues 39-176 of SEQ ID NO:2.

A. Administration Of Pharmaceutical Compositions

Pharmaceutical compositions comprising an activator of WIF-1, a WIF-1 polypeptide, or a WIF-1 polynucleotide can be administered to a patient for the treatment of cancer, e.g., lung cancer or breast cancer. As described in detail below, the activators are administered in any suitable manner, optionally with pharmaceutically acceptable carriers.

The identified activators can be administered to a patient at therapeutically effective doses to prevent, treat, or control cancer. The compounds are administered to a patient in an amount sufficient to elicit an effective therapeutic response in the patient. An effective therapeutic response is a response that at least partially arrests or slows the symptoms or complications of the disease. An amount adequate to accomplish this is defined as "therapeutically effective dose." The dose will be determined by the efficacy of the particular WIF-1 activator employed and the condition of the subject, as well as the body weight or surface area of the area to be treated. The size of the dose also will be determined by the existence, nature, and extent of any adverse effects that accompany the administration of a particular compound or vector in a particular subject.

Toxicity and therapeutic efficacy of such compounds can be determined by standard pharmaceutical procedures in cell cultures or experimental animals, for example, by determining the LD50 (the dose lethal to 50% of the population) and the ED50 (the dose therapeutically effective in 50% of the population). The dose ratio between toxic and therapeutic effects is the therapeutic index and can be expressed as the ratio, $LD_{50}/ED_{50}$. Compounds that exhibit large therapeutic indices are preferred. While compounds that exhibit toxic side effects can be used, care should be taken to design a delivery system that targets such compounds to the site of affected tissue to minimize potential damage to normal cells and, thereby, reduce side effects.

The data obtained from cell culture assays and animal studies can be used to formulate a dosage range for use in humans. The dosage of such compounds lies preferably within a range of circulating concentrations that include the $ED_{50}$ with little or no toxicity. The dosage can vary within this range depending upon the dosage form employed and the route of administration. For any compound used in the methods of the invention, the therapeutically effective dose can be estimated initially from cell culture assays. A dose can be formulated in animal models to achieve a circulating plasma concentration range that includes the $IC_{50}$ (the concentration of the test compound that achieves a half-maximal inhibition of symptoms) as determined in cell culture. Such information can be used to more accurately determine useful doses in humans. Levels in plasma can be measured, for example, by high performance liquid chromatography (HPLC). In general, the dose equivalent of a modulator is from about 1 ng/kg to 10 mg/kg for a typical subject.

Pharmaceutical compositions for use in the present invention can be formulated by standard techniques using one or more physiologically acceptable carriers or excipients. The compounds and their physiologically acceptable salts and solvates can be formulated for administration by any suitable route, including via inhalation, topically, nasally, orally, parenterally (e.g., intravenously, intraperitoneally, intravesically or intrathecally) or rectally.

For oral administration, the pharmaceutical compositions can take the form of, for example, tablets or capsules prepared by conventional means with pharmaceutically acceptable excipients, including binding agents, for example, pregelatinised maize starch, polyvinylpyrrolidone, or hydroxypropyl methylcellulose; fillers, for example, lactose, microcrystalline cellulose, or calcium hydrogen phosphate; lubricants, for example, magnesium stearate, talc, or silica; disintegrants, for example, potato starch or sodium starch glycolate; or wetting agents, for example, sodium lauryl sulphate. Tablets can be coated by methods well known in the art. Liquid preparations for oral administration can take the form of, for example, solutions, syrups, or suspensions, or they can be presented as a dry product for constitution with water or other suitable vehicle before use. Such liquid preparations can be prepared by conventional means with pharmaceutically acceptable additives, for example, suspending agents, for example, sorbitol syrup, cellulose derivatives, or hydrogenated edible fats; emulsifying agents, for example, lecithin or acacia; non-aqueous vehicles, for example, almond oil, oily esters, ethyl alcohol, or fractionated vegetable oils; and preservatives, for example, methyl or propyl-p-hydroxybenzoates or sorbic acid. The preparations can also contain buffer salts, flavoring, coloring, and/or sweetening agents as appropriate. If desired, preparations for oral administration can be suitably formulated to give controlled release of the active compound.

For administration by inhalation, the compounds may be conveniently delivered in the form of an aerosol spray presentation from pressurized packs or a nebulizer, with the use of a suitable propellant, for example, dichlorodifluoromethane, trichlorofluoromethane, dichlorotetrafluoroethane, carbon dioxide, or other suitable gas. In the case of a pressurized aerosol, the dosage unit can be determined by providing a valve to deliver a metered amount. Capsules and cartridges of, for example, gelatin for use in an inhaler or insufflator can be formulated containing a powder mix of the compound and a suitable powder base, for example, lactose or starch.

The compounds can be formulated for parenteral administration by injection, for example, by bolus injection or continuous infusion. Formulations for injection can be presented in unit dosage form, for example, in ampoules or in multi-dose containers, with an added preservative. The compositions can take such forms as suspensions, solutions, or emulsions in oily or aqueous vehicles, and can contain formulatory agents, for example, suspending, stabilizing, and/or dispersing agents. Alternatively, the active ingredient can be in powder form for constitution with a suitable vehicle, for example, sterile pyrogen-free water, before use.

The compounds can also be formulated in rectal compositions, for example, suppositories or retention enemas, for example, containing conventional suppository bases, for example, cocoa butter or other glycerides.

Furthermore, the compounds can be formulated as a depot preparation. Such long-acting formulations can be administered by implantation (for example, subcutaneously or intramuscularly) or by intramuscular injection. Thus, for example, the compounds can be formulated with suitable polymeric or hydrophobic materials (for example as an emulsion in an acceptable oil) or ion exchange resins, or as sparingly soluble derivatives, for example, as a sparingly soluble salt.

The compositions can, if desired, be presented in a pack or dispenser device that can contain one or more unit dosage forms containing the active ingredient. The pack can, for example, comprise metal or plastic foil, for example, a blister pack. The pack or dispenser device can be accompanied by instructions for administration.

VII. Methods for Treating Cancer

The methods of the present invention for treating a cancer wherein WIF-1 is down-regulated and for inducing apoptosis in cells wherein WIF-1 is down-regulated is based, in part, on the discovery that WIF-1, while being expressed in normal cells, is underexpressed in human cancer cells. Cancers wherein WIF-1 is under-expressed and that can be treated using the methods of the invention include lung cancer, breast cancer, colorectal cancer, melanoma, colon cancer, mesothelioma, ovarian cancer, gastric cancer, kidney cancer, bladder cancer, prostate cancer, uterus cancer, thyroid cancer, pancreatic cancer, cervical cancer, esophageal cancer, head and neck cancer, hepatocellular carcinoma, brain tumor, vulval or testical cancer, sarcoma, leukemia, lymphoma, glioma and glioblastoma. A preferred cancer is lung cancer, hepatocellular cancer, colorectal cancer, or melanoma.

The present invention provides a method for treatment or prevention of a cancer wherein WIF-1 expression is down-regulated. This method comprises the step of administering to a patient a pharmaceutical composition. Such pharmaceutical compositions comprise, for example, a WIF-1 polypeptide, a WIF-1 analog, a WIF-1 mimetic, a WIF-1 related polypeptide; antibodies to the foregoing; a polynucleotide encoding a WIF-1 polypeptide, a WIF-1 analog, a WIF-1 mimetic, a WIF-1 related polypeptide; an activator of WIF-1 expression; or a modulator of WIF-1 activity. Pharmaceutical compositions of the present invention are administered alone or in combination with one or more additional therapeutic compounds or treatments. Examples of such therapeutic compounds or treatments include, but are not limited to, taxol, cyclophosphamide, tamoxifen, fluoruracil and doxorubicin.

Methods for treating cancer may optionally comprise one or more of the following steps: obtaining a biological sample of tissue or fluid from an individual; screening the biological sample for the expression of a WIF-1 polypeptide, for example by contacting the biological sample with an antibody directed to WIF-1; or screening the biological sample for expression of a WIF-1 polynucleotide, for example by detecting WIF-1 mRNA.

A. Inhibition of Cell Proliferation

WIF-1 polypeptides of the present invention find use in a variety of ways. In a preferred embodiment of this invention, a method of inhibiting proliferation of a cell that underexpresses WIF-1 is provided. "Proliferation" refers to the growth of a cell, the reproduction or multiplication of a cell or morbid cysts. The WIF-1 that is underexpressed can be either a WIF-1 polypeptide or a WIF-1 mRNA. This method comprises the step of contacting the cell with an amount of a WIF-1 polypeptide effective to inhibit proliferation of the cell. WIF-1 polypeptides, preferably WIF-1 subdomain polypeptides of the present invention are useful for inhibiting proliferation of a cell, preferably a cancer cell.

In a preferred embodiment of the present invention, this method is practiced in vitro. As further described herein, methods of the present invention can also be practiced in vivo.

In a preferred embodiment of the present invention, the cell being contacted with a WIF-1 polypeptide is a cancer cell selected from the group consisting of lung cancer, breast cancer, colorectal cancer, melanoma, colon cancer, mesothelioma, ovarian cancer, gastric cancer, kidney cancer, bladder cancer, prostate cancer, uterus cancer, thyroid cancer, pancreatic cancer, cervical cancer, esophageal cancer, head and neck cancer, hepatocellular cancer, brain cancer, vulval cancer, testical cancer, sarcoma, leukemia, lymphoma, glioma, and glioblastoma cell. A preferred cancer cell is a lung cancer cell, a hepatocellular cancer cell, a colorectal cancer cell, or a melanoma cell.

In a preferred embodiment of the present invention, the cancer cell that is contacted with a WIF-1 polypeptide comprises a hypermethylated WIF-1 promoter as described herein. Typically, upon decreasing the methylation of the WIF-1 promoter, e.g., by using the methods described herein, expression of WIF-1 in the cell increases.

B. Inhibiting Wnt Signaling

WIF-1 polypeptides of the present invention find use in a variety of ways. In another preferred embodiment of this invention a method of inhibiting Wnt signaling in a cell, preferably a cancer cell as described herein, is provided. This method comprises the step of contacting the cell that underexpresses WIF-1 with an amount of a WIF-1 polypeptide effective to inhibit Wnt signaling. The WIF-1 polypeptides, preferably the WIF-1 subdomain polypeptides of this invention can be used to inhibit Wnt signaling in a cell, preferably a cancer cell.

C. Treating a Disease

WIF-1 polypeptides of the present invention find use in a variety of ways. In another preferred embodiment of this invention a method of treating a disease associated with underexpression of WIF-1 is provided. This method comprises the step of administering to a subject, preferably to a subject in need of such treatment, an amount of a polypeptide having WIF-1 activity effective for treating the disease. Preferably, the subject is a human. The WIF-1 polypeptides, preferably the WIF-1 subdomain polypeptides of this invention can be used to treat a disease associated with underexpression of WIF-1.

In a preferred embodiment of the present invention, the disease associated with underexpression of WIF-1 is a cancer. WIF-1 polypeptides, preferably WIF-1 subdomain polypeptides of the present invention are useful for treating a cancer selected from the group consisting of lung cancer, breast cancer, colorectal cancer, melanoma, colon cancer, mesothelioma, ovarian cancer, gastric cancer, kidney cancer, bladder cancer, prostate cancer, uterus cancer, thyroid cancer, pancreatic cancer, cervical cancer, esophageal cancer, head and neck cancer, hepatocellular cancer, brain cancer, vulval cancer, testical cancer, sarcoma, leukemia, lymphoma, glioma, and glioblastoma cell. A preferred cancer is lung cancer, hepatocellular cancer, colorectal cancer, or melanoma.

D. Methods for Treating Cancer Using a WIF-1 Polynucleotide

The present invention provides a method for treatment or prevention of various cancers wherein WIF-1 expression is down-regulated. In some aspects of the present invention, a cell is contacted with a composition that incrases WIF-1 expression in the cell. In a preferred embodiment of the present invention, a composition comprises a nucleic acid encoding a WIF-1 polypeptide, preferably a WIF-1 subdomain polypeptide.

The present invention provides polynucleotides that encode the WIF-1 polypeptide of SEQ ID NO:2, the WIF-1 polypeptide of SEQ ID NO:14, the WIF-1 polypeptide of SEQ ID NO:15, the WIF-1 polypeptide of SEQ ID NO:16, a WIF-1 subdomain polypeptide comprising amino acid residues 1-180 of SEQ ID NO:2; a WIF-1 subdomain polypeptide comprising amino acid residues 29-180 of SEQ ID NO:2, a WIF-1 subdomain polypeptide comprising amino acid residues 29-176 of SEQ ID NO:2; or a WIF-1 subdomain polypeptide comprising amino acid residues 39-176 of SEQ ID NO:2.

In other preferred embodiments of the present invention, the polynucleotide comprises the nucleotide sequence of SEQ ID NO:1, the nucleotide sequence of SEQ ID NO: 17, the nucleotide sequence of SEQ ID NO:18, or the nucleotide sequence of SEQ ID NO:19. Nucleotide sequence encoding the WIF-1 subdomain polypeptide comprising amino acid residues 1-180 of SEQ ID NO:2; the WIF-1 subdomain polypeptide comprising amino acid residues 29-180 of SEQ ID NO:2, the WIF-1 subdomain polypeptide comprising amino acid residues 29-176 of SEQ ID NO:2; or the WIF-1 subdomain polypeptide comprising amino acid residues 39-176 of SEQ ID NO:2 can be deduced from SEQ ID NO:1.

In a preferred embodiment of the present invention, the method of treating a cancer comprises the step of administering to a patient diagnosed with cancer a therapeutically effective amount of a pharmaceutical composition comprising (i) a polynucleotide encoding a WIF-1 polypeptide and (ii) a pharmaceutically acceptable carrier.

In a preferred embodiment of this method, the polynucleotide encodes the WIF-1 polypeptide of SEQ ID NO:2. In another preferred embodiment of the present invention, the polynucleotide encodes the WIF-1 polypeptide of SEQ ID NO:14. In yet another preferred embodiment of the present invention, the polynucleotide encodes the WIF-1 polypeptide of SEQ ID NO:15. In another preferred embodiment of the present invention, the polynucleotide encodes the WIF-1 polypeptide of SEQ ID NO:16. Other preferred polynucleotides encode a WIF-1 subdomain polypeptide comprising amino acid residues 1-180 of SEQ ID NO:2; a WIF-1 subdomain polypeptide comprising amino acid residues 29-180 of SEQ ID NO:2; a WIF-1 subdomain polypeptide comprising amino acid residues 29-176 of SEQ ID NO:2; or a WIF-1 subdomain polypeptide comprising amino acid residues 39-176 of SEQ ID NO:2.

In another preferred embodiment of the present invention, the polynucleotide comprises SEQ ID NO:1. In other preferred embodiments, the polynucleotide comprises SEQ ID NO:17, SEQ ID NO:18, SEQ ID NO:19, a nucleotide sequence encoding the WIF-1 subdomain polypeptide comprising amino acid residues 1-180 of SEQ ID NO:2, a nucleotide sequence encoding the WIF-1 subdomain polypeptide comprising amino acid residues 29-180 of SEQ ID NO:2, a nucleotide sequence encoding the WIF-1 subdomain polypeptide comprising amino acid residues 29-176 of SEQ ID NO:2; or a nucleotide sequence encoding the WIF-1 subdomain polypeptide comprising amino acid residues 39-176 of SEQ ID NO:2.

The manner and timing of administration of the pharmaceutical composition comprising a polynucleotide encoding a WIF-1 polypeptide is not critical to the invention. The pharmaceutical composition can be administered to a patient in a variety of ways as described herein. In a preferred aspect of this method, the pharmaceutical composition comprising the polynucleotide encoding the WIF-1 polypeptide is injected adjacent to a tumor. In another aspect, the pharmaceutical composition is injected directly into a tumor. Upon monitoring the course of cancer (e.g., regression of cancer as determined by the size of the tumor) a treating physician skilled in the art will determine if the injection of the pharmaceutical composition is performed once or is repeated after an appropriate time. Injections may be done on a daily basis.

E. Methods for Treating Cancer Using a WIF-1 Polypeptide

The present invention provides a method for treatment or prevention of various cancers wherein WIF-1 expression is down-regulated. In a preferred embodiment of the present invention, this method comprises the step of administering to a patient diagnosed with cancer a therapeutically effective amount of a pharmaceutical composition comprising (i) a WIF-1 polypeptide and (ii) a pharmaceutically acceptable carrier.

In a preferred embodiment of this method, the WIF-1 polypeptide comprises the amino acid sequence of SEQ ID NO:14. In another preferred embodiment of the present invention, the WIF-1 polypeptide comprises the amino acid sequence of SEQ ID NO:15. In other embodiments of the present invention, a WIF-1 polypeptide comprises the amino acid sequence of SEQ ID NO:2 or SEQ ID NO:16. Other preferred WIF-1 polypeptides are WIF-1 subdomain polypeptides comprising amino acid residues 1-180 of SEQ ID NO:2, amino acid residues 29-180 of SEQ ID NO:2, amino acid residues 29-176 of SEQ ID NO:2, or amino acid residues 39-176 of SEQ ID NO:2.

The manner and timing of administration of a pharmaceutical composition comprising a WIF-1 polypeptide is not critical to the invention. The pharmaceutical composition can be administered to a patient in a variety of ways as described herein. In a preferred aspect, the pharmaceutical composition comprising the WIF-1 polypeptide is injected adjacent to a tumor. In another aspect, the pharmaceutical composition is injected directly into a tumor. Upon monitoring the course of cancer (e.g., regression of cancer as determined by the size of the tumor) a treating physician skilled in the art will determine if the injection of the pharmaceutical composition is performed once or is repeated after an appropriate time. Injections may be done on a daily basis.

1. WIF-1 Mimetics

It is also recognized by those skill in the art that peptide mimetics which possess the same structure as a WIF-1 polypeptide, a WIF-1 peptide, or a polypeptide comprising a Wnt binding domain of WIF-1 can be useful for practicing the methods of the present invention and for inclusion in the kits of the present invention. A peptide mimetic is a compound which has sufficient structural similarity to a polypeptide so that the desirable properties of the polypeptide are retained by the mimetic. Often the mimetic has a basic structure that mimics the basic structure of the polypeptide and/or has the salient biological properties of the polypeptide. For example, peptide mimetics used a protease inhibitors are described in WO 94/05639. A WIF-1 peptide mimetic refers to any peptide or non-peptide compound that is able to mimic the biological action of a naturally occurring or recombinant WIF-1 polypeptide. Mimetics can include, but are not limited to (i) peptides that have substantial modifications such that, for example, no or very little side chain similarity with a WIF-1 polypeptide and the mimetic exists (such modification, for example, may decrease the mimetic's susceptibility to degradation); (ii) non-proteinaceous portions of an isolated peptide; or (iii) synthetic or natural organic molecules, including nucleic acids and agents identified through combinatorial chemistry. For example, such mimetics can be designed, selected, and/or otherwise identified using a variety of methods known in the art, including, for example, construction and screening of large chemically diverse molecular libraries, libraries of synthetic or natural compound libraries, or by rational, directed or random design. The general goal of screening such libraries is to utilize sequential application of combinatorial selection to obtain high affinity agents for the binding site of interest. For directed or rational drug design the structure of the Wnt binding domain of WIF-1 can be used as a base for selection and design of a peptide mimetic. Peptide mimetics are also described, for example, in U.S. Pat. Nos. 6,514,729, 6,627,186, 6,682,923, and 6,746,853.

F. Determining the Course of Cancer (Progression, Regression)

The stage or severity of cancer refers to different clinical stages of a tumor. Clinical stages of tumors are defined by various parameters which are well-established in the field of medicine. Some of the parameters include morphology, size of tumor, the degree in which the tumor has metastasized through a patient's body and the like.

In one preferred embodiment of the present invention, the cancer is determined as part of determining the course of cancer. Thus, the invention provides methods for determining the course cancer, in a subject. Cancer course refers to changes in cancer status over time, including cancer progression (worsening) and cancer regression (improvement). Regression includes tumor remission, reduction or diminution in tumor size, decrease in number cancerous cells, and lessening of symptoms associated with prostate cancer.

G. Monitoring the Effect of Surgery or an Anti-Cancer Drug or Therapy Administered to a Subject with Cancer Wherein WIF-1 is Downregulated As described above, a composition comprising a WIF-1 is useful for treatment of cancer wherein WIF-1 expression is down-regulated. However, other drugs, for example, a composition comprising an activator of WIF-1, as described herein, will also be useful for treating a cancer in a patient wherein WIF-1 expression is down-regulated.

In a preferred embodiment of the present invention, a cancer status is determined as part of monitoring the effect of surgery (e.g., removal of tumor), the effect of an anti-cancer drug or a therapy administered to a subject diagnosed with a cancer wherein WIF-1 expression is down-regulated. The effect of surgery or an anti-cancer drug or a therapy administered to a subject with cancer may include reoccurrence of cancer, progression of cancer (worsening) and cancer regression (improvement).

Using the compositions, methods and kits of the present invention, a WIF-1 level is determined in a biological sample from a subject at various times after surgery or at various of having been given an anti-cancer drug or a therapy. A WIF-1 level detected in a biological sample from a subject at a first time (t1; e.g., before giving an anti-cancer drug or a therapy) that is lower than the WIF-1 level detected in a comparable biological sample from the same subject taken at a second time (t2; e.g., after giving the anti-cancer drug or the therapy), indicates that the cancer in the subject is regressing. Likewise, a lower WIF-1 level at a second time compared to a WIF-1 level at a first time, indicates that the cancer in the subject is progressing. Similarly, a WIF-1 level detected in a biological sample from a subject at a first time (t1; e.g., shortly after surgery) that is lower than the WIF-1 level detected in a comparable biological sample from the same subject taken at a second time (t2; e.g., weeks or months after surgery), may indicate that the cancer in the subject is not reoccurring. Likewise, a lower WIF-1 level at a second time compared to a WIF-1 level at a first time, may indicate that the cancer in the subject is reoccurring.

VIII. Methods for Inducing Apoptosis

Apoptosis plays a central role in both the development and homeostasis of multicellular organisms. Apoptosis can be induced by multiple independent signaling pathways that converge upon a final effector mechanism consisting of multiple interactions between several death receptors and their ligands, which belong to the tumor necrosis factor (TNF) receptor/ligand superfamily. The best-characterized death receptors are CD95 ("Fas"), TNFR1 (p55), death receptor 3 (DR3 or Apo3/TRAMO), DR4 and DR5 (apo2-TRAIL-R2).

The final effector mechanism of apoptosis is the activation of a series of proteinases designated as caspases. The activation of these caspases results in the cleavage of a series of vital cellular proteins and cell death.

The present invention provides methods for inducing apoptosis in a cell wherein WIF-1 expression is down-regulated. In one aspect, the method for inducing apoptosis in a cell comprises the step of exposing the cell to a composition or contacting the cell with a composition comprising either (i) a polynucleotide encoding a WIF-1 polypeptide, a WIF-1 analog, a WIF-1 mimetic, a WIF-1 related polypeptide, an activator of WIF-1 expression or a modulator of WIF-1 activity or (ii) a WIF-1 polypeptide, a WIF-1 analog, a WIF-1 mimetic, a WIF-1 related polypeptide, an activator of WIF-1 expression or a modulator of WIF-1 activity. Typically, the cells are exposed to or contacted with an effective amount of the composition.

In a preferred embodiment, the cells are exposed ex vivo to or contacted ex vivo with the composition. In another preferred embodiment, the cell is exposed in vivo to or contacted in vivo with the composition.

A. Methods for Inducing Apoptosis Using a WIF-1 Polynucleotide

In a preferred embodiment, the method for inducing apoptosis in a cell wherein WIF-1 expression is down-regulated comprises the step of exposing the cell to a composition or contacting the cell with a composition comprising a WIF-1 polynucleotide. In a preferred embodiment, the polynucleotide encodes the WIF-1 polypeptide of SEQ ID NO:2. In another preferred embodiment of the present invention, the polynucleotide encodes the WIF-1 polypeptide of SEQ ID NO:14. In yet another preferred embodiment of the present invention, the polynucleotide encodes the WIF-1 polypeptide of SEQ ID NO:15. In another preferred embodiment of the present invention, the polynucleotide encodes the WIF-1 polypeptide of SEQ ID NO:16. Other preferred polynucleotides encode a WIF-1 subdomain polypeptide comprising amino acid residues 1-180 of SEQ ID NO:2; a WIF-1 subdomain polypeptide comprising amino acid residues 29-180 of SEQ ID NO:2, a WIF-1 subdomain polypeptide comprising amino acid residues 29-176 of SEQ ID NO:2; or a WIF-1 subdomain polypeptide comprising amino acid residues 39-176 of SEQ ID NO:2.

In another preferred embodiment of the present invention, the polynucleotide comprises SEQ ID NO:1. In other preferred embodiments, the polynucleotide comprises SEQ ID NO:17, SEQ ID NO:18, or SEQ ID NO: 19, a nucleotide sequence encoding the WIF-1 subdomain polypeptide comprising amino acid residues 1-180 of SEQ ID NO:2, a nucleotide sequence encoding the WIF-1 subdomain polypeptide comprising amino acid residues 29-180 of SEQ ID NO:2; a nucleotide sequence encoding the WIF-1 subdomain polypeptide comprising amino acid residues 29-176 of SEQ ID NO:2; or a nucleotide sequence encoding the WIF-1 subdomain polypeptide comprising amino acid residues 39-176 of SEQ ID NO:2.

In one aspect of the present invention, a WIF-1 polynucleotide is used to induce apoptosis in vitro, e.g., in a cultured cell line. In another preferred aspect, the WIF-1 polynucleotide is used to induce apoptosis in vivo, i.e., in an animal, preferably a mammal, including human, and preferably in cancer cells.

B. Methods for Inducing Apoptosis Using a WIF-1 Polypeptide

WIF-1 polypeptides of the present invention find use in a variety of ways. In another preferred embodiment of this invention a method of inducing apoptosis in a cell, preferably a cancer cell, that underexpresses a WIF-1, is provided. This method comprises the step of contacting the cell with a polypeptide having WIF-1 activity in an amount effective to induce apoptosis in the cell.

In a preferred embodiment of this method, the polypeptide having WIF-1 activity is a WIF-1 polypeptide comprising the amino acid sequence of SEQ ID NO:14. In another preferred embodiment of this method, the WIF-1 polypeptide comprises the amino acid sequence of SEQ ID NO:15. In yet other embodiments of this method, a WIF-1 polypeptide comprises the amino acid sequence of SEQ ID NO:2 or SEQ ID NO:16. In another preferred embodiment of the present invention, the polypeptide having WIF-1 activity is a WIF-1 subdomain polypeptides as fully described herein.

In one aspect of the present invention, a WIF-1 polypeptide is used to induce apoptosis in vitro, e.g., in a cultured cell line. In another preferred aspect, the WIF-1 polypeptide is used to induce apoptosis in vivo, i.e., in an animal, preferably a mammal, including human, and preferably in cancer cells.

IX. Gene Therapy

In on aspect, a polynucleotide encoding a WIF-1 polypeptide, a WIF-1 analog, a WIF-1 mimetic, a WIF-1 related polypeptide; an activator of WIF-1 expression; or a modulator of WIF-1 activity, is administered to promote WIF-1 function by way of gene therapy. Gene therapy refers to administration to a subject of an expressed or expressible nucleic acid. In this embodiment, the nucleic acid produces its encoded polypeptide that mediates a therapeutic effect by promoting WIF-1 function.

Any of the methods for gene therapy available in the art and described herein can be used according to the present invention. For general reviews of the methods of gene therapy, see, Goldspiel et al., *Clinical Pharmacy* 12:488-505 (1993); Wu and Wu, *Biotherapy* 3:87-95 (1991); Tolstoshev, *Ann. Rev. Pharmacol. Toxicol.* 32:573-596 (1993); Mulligan, *Science* 260:926-932 (1993); Morgan and Anderson, *Ann. Rev. Biochem.* 62:191-217 (1993); and TIBTECH 11 (5):155-215 (May, 1993). Methods commonly known in the art of recombinant DNA technology which can be used are described in Ausubel et al. (eds.), *Current Protocols in Molecular Biology*, John Wiley & Sons, NY (1993); and Kriegler, *Gene Transfer and Expression, A Laboratory Manual*, Stockton Press, NY (1990).

In a preferred aspect, a nucleic acid promoting WIF-1 function by way of gene therapy comprises a sequence encoding a WIF-1 polypeptide, a fragment or chimeric protein thereof, wherein the nucleotide sequence is part of an expression vector that expresses a WIF-1 polypeptide, a fragment or chimeric protein thereof in a suitable host. In particular, such a nucleic acid has a promoter operably linked to the WIF-1 coding region. The promoter may be inducible or constitutive (and, optionally, tissue-specific). In another particular embodiment, a nucleic acid molecule is used in which the WIF-1 coding sequences and any other desired sequences are flanked by regions that promote homologous recombination at a desired site in the genome, thus providing for intrachromosomal expression of the WIF-1 nucleic acid (Koller and Smithies, *Proc. Natl. Acad. Sci. USA* 86:8932-8935 (1989); Zijlstra et al., *Nature* 342:435-438 (1989)).

Delivery of the nucleic acid into a subject may be direct, in which case the subject is directly exposed to or contacted with the nucleic acid or nucleic acid-carrying vector; this approach is known as in vivo gene therapy. Alternatively, delivery of the nucleic acid into the subject may be indirect, in which case cells are first transformed with the nucleic acid in vitro and then transplanted into the subject; this approach is known as ex vivo gene therapy.

X. Kits for Use in Diagnostic and/or Prognostic Applications

For use in diagnostic, research, and therapeutic applications suggested above, kits are also provided by the invention. In the diagnostic and research applications such kits may include any or all of the following: assay reagents, buffers, WIF-1 polypeptides, WIF-1-specific nucleic acids or antibodies, hybridization probes and/or primers, WIF-1 expression constructs, small molecule activators of WIF-1 etc. A therapeutic product may include sterile saline or another pharmaceutically acceptable emulsion and suspension base.

In addition, the kits may include instructional materials containing directions (i.e., protocols) for the practice of the methods of this invention. The instructions may be present in the subject kits in a variety of forms, one or more of which may be present in the kit. While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

The present invention also provides for kits for screening for modulators of WIF-1 activity. Such kits can be prepared from readily available materials and reagents. For example, such kits can comprise one or more of the following materials: a WIF-1 polypeptide or polynucleotide, reaction tubes, and instructions for testing WIF-1activity. Optionally, the kit contains biologically active WIF-1 protein. A wide variety of kits and components can be prepared according to the present invention, depending upon the intended user of the kit and the particular needs of the user.

In a preferred embodiment of the present invention, the kit is a pharmaceutical kit and comprises a pharmaceutical composition comprising (i) a polynucleotide encoding a WIF-1 polypeptide and (ii) a pharmaceutical acceptable carrier. In another preferred embodiment of the present invention, the kit is a pharmaceutical kit and comprises a pharmaceutical composition comprising (i) a WIF-1 polypeptide, preferably a WIF-1 subdomain polypeptide and (ii) a pharmaceutical acceptable carrier. Pharmaceutical kits optionally comprise an instruction stating that the pharmaceutical composition can or should be used for treating a cancer wherein WIF-1 expression is down-regulated.

The kits according to the present invention may further comprise a reagent for performing mass spectrometry. Such reagents are well known to those skilled in the art and include, for example, a probe or a chip.

Additional kit embodiments of the present invention include optional functional components that would allow one of ordinary skill in the art to perform any of the method variations described herein.

Although the forgoing invention has been described in some detail by way of illustration and example for clarity and understanding, it will be readily apparent to one ordinary skill in the art in light of the teachings of this invention that certain variations, changes, modifications and substitution of equivalents may be made thereto without necessarily departing from the spirit and scope of this invention. As a result, the embodiments described herein are subject to various modifications, changes and the like, with the scope of this invention being determined solely by reference to the claims appended hereto.

Those of skill in the art will readily recognize a variety of non-critical parameters that could be changed, altered or modified to yield essentially similar results.

While each of the elements of the present invention is described herein as containing multiple embodiments, it should be understood that, unless indicated otherwise, each of the embodiments of a given element of the present invention is capable of being used with each of the embodiments of the other elements of the present invention and each such use is intended to form a distinct embodiment of the present invention.

All publications, patents and patent applications cited in this specification are herein incorporated in their entireties by reference as if each individual publication, patent or patent application were specifically and individually indicated to be incorporated by reference.

As can be appreciated from the disclosure above, the present invention has a wide variety of applications. The invention is further illustrated by the following examples, which are only illustrative and are not intended to limit the definition and scope of the invention in any way.

XI. Examples

Example 1

General Methods

A. Cell Lines and Tissue Samples

NSCLC cell lines (NCI-H1703, NCI-H460, NCI-H838 and NCI-A549), melanoma cell line LOX, hepatocellular cancer cell lines SNU398, and colorectal cancer cell line HCT116 were obtained from American Type Culture Collections (ATCC; Manassas, Va.) and cultured in RPMI 1640 supplemented with 10% fetal bovine serum, penicillin (100 IU/ml) and streptomycin (100 µg/ml). Normal human small airway epithelial cells (SAEC) and bronchial epithelial cells (NHBE, 16HBE) (primary cultures) were obtained from Cambrex Bio Science Walkersville, Inc. (Walkersville, Md.) or Clonetics (Walkersville, Md.) and cultured in Clonetics SAGM™ Bullet Kit. All cells were cultured at 37° C. in a humid incubator with 5% $CO_2$.

Fresh lung cancer tissues and adjacent normal lung tissues from patients undergoing resection for lung cancers were collected at the time of surgery, and immediately snap-frozen in liquid nitrogen (IRB approval H8714-15319-040). These tissue samples were kept at −170° C. in a liquid nitrogen freezer before use.

B. Cloning and Sequence Analysis

To clone the promoter region of the human WIF-1 gene, a PCR-based technique was used. Genomic DNA of the cell lines and fresh tissue samples was extracted using DNA STAT-60™ reagent (TEL-TEST, Inc., Friendswood, Tex.), according to the manufacturer's protocol. Bisulfite modification of genomic DNA was carried out by using a methylation kit (EZ DNA methylation kit, Zymo Research, Orange Calif.). Bisulfite-treated genomic DNA was amplified using two pairs of primers: 5'-GAGTGATGTTTTAGGGGTTT-3' (forward) (SEQ ID NO:8) and 5'-CCTAAATAC-CAAAAAACCTAC-3' (reverse) (SEQ ID NO:9) designed to amplify nt −555 to −140 of the WIF-1 promoter region and 5'-GTAGGTTTTTTGGTATTTAGG-3' (forward) (SEQ ID NO:10) and 5'-TCCATAAATACAAACTCTCCTC-3' (reverse) (SEQ ID NO:11) to amplify nt −161 to +118 (the start codon ATG of WIF-1 is defined as +1). The PCR products were extracted from the agarose gel using an extraction kit (QIAquick Gel Extraction Kit, Qiagen, Valencia, Calif.) and were subsequently sequenced at the DNA-sequencing Core Facility of the UCSF Cancer Center (San Francisco, Calif.).

Truncated forms of the 5' genomic region of WIF-1 were generated by PCR from human genomic DNA and subcloned into the pGL3Basic vector. The digested inserts and vector were gel-purified and ligated to give the deletion constructs. The cloned fragments were checked by restriction enzyme digestions and sequencing.

C. Transient Transfections and Promoter Activity Measurements

For transient transfections experiments cells ($2\times10^5$) were plated in six-well plates 24 hrs before transfections. Lipofectamine 2000 was used to mediate transfections using 1.0 µg of each promoter construct in pGL3Basic vector and 0.5 µg pSV-β-galactosidase for correcting transfections efficiency. Transfected cells were incubated for 24 hrs and then luciferase activity was measured. In some experiments transfected cells were treated with cytokines for 6 hrs before subsequent measurement of luciferase activity. All luciferase activities were normalized to β-galactosidase activity and were given relative to the basal activity of empty pGL3Basic vector, which was set to unity. In experiments where cells were treated with cytokines normalized luciferase activities were given relative to the basal activity of empty pGL3Basic vector after cytokine treatment. Measurements were performed in triplicates and repeated in at least three independent experiments. The data shown represent mean values (+S.D.).

D. Colony Formation Assay

For transient transfection experiments, cells ($2\times10^5$) were plated in six-well plates 24 hrs before transfection. Lipofectamine 2000 (Life Technologies) was used to mediate transfection using 5.0 µg of WIF-1 cDNA construct in pcDNA3 vector or 5.0 µg empty pcDNA3 vector as control, according to the manufacture's protocol. Transfected cells were stripped and plated on 10 cm cell culture dishes at 48 hours after transfection. The cells were then selected by G418 (400 µg/ml). Colonies were stained with 0.5% Methylene Blue and counted 4 weeks after the transfection.

E. Conditioned Medium (CM), Recombinant Protein and Protein Incubation

The pcDNA3.1 expression vectors comprising a human WIF-1 open reading frame were used to produce condition medium. In one set of experiments, the WIF-1 open reading frame comprised the full-length WIF-1 coding region, i.e., encoding the WIF-polypeptide of SEQ ID NO:2. Thus, after cleavage of the signal peptide, a recombinant mature WIF-1 polypeptide comprising amino acid residues 29-379 of SEQ ID NO:2 was purified. In another set of experiments, the WIF-1 open reading frame comprised the WIF-1 subdomain polypeptide coding region, e.g., encoding the WIF-polypeptide as shown in SEQ ID NO:26. Thus, after cleavage of the signal peptide, recombinant WIF-1 subdomain polypeptides comprising an amino acid sequence of SEQ ID NO:27 was purified. Another WIF-1 subdomain polypeptide sequence is shown in SEQ ID NO:28. After cleavage of the signal peptide, a recombinant WIF-1 subdomain polypeptides comprising the amino acid sequence of SEQ ID NO:29 was purified.

Briefly, 293T cell line was maintained in serum-free Freestyle 293 Expression medium before Lipofectamine 2000 (Life Technologies) was used to mediate transfection of WIF-1 cDNA construct in pcDNA3.1/myc-his according to the manufacture's protocol. Serum-free conditioned medium (control CM) was prepared from untransfected 293T cells. The conditioned medium was collected after 4 and 7 days. The collected CM was cleared of cellular debris by centrifugation, concentrated 10-fold by centrifugation, filtered, and frozen at −80° C. Purified recombinant human WIF-1 protein produced by wheat germ was purchased from Abnova Corp. (Taiwan, ROC). NSCLC cells were plated in 6-well plates one day before the experiments. Then normal media was replaced by media containing CM with or without recombinant human WIF-1 protein at various concentrations and the cells were incubated at 37° C. in a humid incubator with 5% $CO_2$. Typically 40 µl, 100 µl and 200 µl of CM comprising a WIF-1 polypeptide were added to the cells. Based on quantification by SDS-PAGE, the concentration of WIF-1 polypeptide added to the cells and leading to the detection of WIF-1 polypeptide activity was estimated to range from about 10 ng/ml to about 500 ng/ml. In order to detect a similar WIF-1 polypeptide activity for WIF-1 polypeptides produced in bacteria, a much higher concentration of the WIF-1 polypeptides was added to the cells. In some experiments, the amount of bacterially expressed WIF-1 was about 500 ug/ml. This corresponded to more than 1000-fold higher concentration than the concentration needed for the proteins produced by mammalian cells.

F. Apoptosis Analysis

Three days, 5 days or one week after transfection (as described above), the cells (e.g., NSCLC cells) were harvested by trypsinization and processed for determination of cell surface annexin-V and propidium iodide (PI) contents using an Annexin V FITC Apoptosis Detection Kit (Oncogene, Cambridge, Mass.; Apotarget, BioSource International), according to the manufacturer's protocol. With the use of an Annexin-V-PI double staining regime, three populations of cells are distinguishable in two color flow cytometry. (a) non-apoptotic cells are annexin-V and PI negative; (b) early apoptotic cells with exposed phosphatidylserine but intact cell membranes bound to Annexin V-FITC but excluded propidium iodide; (c) cells in necrotic or late apoptotic cells were labeled with both Annexin V-FITC and propidium iodide. The stained cells were immediately analyzed by flow cytometry (FACScan; Decton Dickinson, Franklin Lake, N.J.).

G. Semi-Quantitative RT-PCR

Total RNA from lung cancer cell lines, fresh lung cancer and paired adjacent normal tissue were isolated using an extraction kit (RNeasy Mini Kit, Qiagen, Valencia, Calif., USA). RT-PCR was performed in GeneAmp PCR system 9700 using One-step RT-PCR Kit from Life Technologies Inc., according to the manufacture's protocol. Primers for RT-PCR were obtained from Operon Technologies Inc. (Alameda, Calif.). Primer sequences for the human WIF-1 cDNA were: 5'-CCGAAATGGAGGCTTTTGTA-3' (forward) (SEQ ID NO: 12) and 5'-TGGTTGAG-CAGTTTGCTTTG-3' (reverse) (SEQ ID NO: 13). GAPDH was used as an internal control. 5-aza-2'-deoxycytidine (DAC) (Sigma, St. Louis, Mo.) treatment was performed as described previously (Altieri, *Nat. Rev. Cancer* 3(1):46-54 (2003); Blanc-Brude et al., *Clin. Cancer Res.* 9(7):2683-92 (2003); Bowen et al., *J. Invest. Dermatol.* 120(1):48-55 (2003); Cong et al., *Mol. Cell. Biol.* 23(23):8462-70 (2003); Deng et al., *Cell* 115(1):61-70 (2003); He et al., *Neoplasia In Press* (2003); Ishitani et al., *Mol. Cell. Biol.* 23(1):131-9 (2003); Kawano and Kypta, *J. Cell. Sci.* 116 (Pt 13):2627-34 (2003); Kim et al., *Lancet* 362(9379):205-9 (2003); Krilleke et al., *Int. J. Cancer* 107(4):520-7 (2003); Pham et al., *Mol. Pathol.* 56(5)280-5 (2003); Soengas and Lowe, *Oncogene* 22(20):3138-51 (2003); Topol et al., *J. Cell. Biol.* 162(5):899-908 (2003); Uematsu et al., *Oncogene* 22(46):7218-21 (2003); Uematsu et al., *Cancer Res.* 63(15):4547-51 (2003); Usami et al., *Oncogene* 22(39):5978-86 (2003); Veeman et al., *Dev. Cell.* 5(3):367-77 (2003); Westfall et al., *J. Cell Biol.* 162(5):889-98; and Wong et al., *Mol. Cell.* 12(5):1251-60 (2003)).

H. Western Blotting

Standard protocols for Western blotting were used. WIF-1 rabbit polyclonal antibody was obtained from Santa Cruz Biotechnology, Inc. (Santa Cruz, Calif.). Anti-WIF-1, Anti-Dvl3, and anti-Survivin antibodies were from Santa Cruz Biotechnology (Santa Cruz, Calif.). Anti-human WIF-1 monoclonal antibody was purchased from R&D Systems (Minneapolis, Minn.). Anti-cyclin D1 antibody was from Oncogene (Cambridge, Mass.). Anti-β-Actin monoclonal antibody was obtained from Cell Signaling Technology, Inc. (Beverly, Mass.). Anti-β-Catenin antibody was purchased from Transduction Laboratories (Lexington, Ky.). Anti-Cytochrome c antibody was from BD Biosciences (San Diego, Calif.). Cytosolic proteins were prepared.

I. Methylation-Specific PCR

Bisulfite-treated genomic DNA was amplified using either a methylation-specific or unmethylation-specific primer set. HotStarTaq DNA polymerase (Qiagen Inc.) was used in the experiments. Sequences of the methylation-specific primers were: 5'-GGGCGTTTTATTGGGCGTAT-3' (forward) (SEQ ID NO: 4) and 5'-AAACCAACAATCAACGAAC-3' (reverse) (SEQ ID NO: 5). Sequences of the unmethylation-specific primers were: 5'-GGGTGTTTTATTGGGTGTAT-3' (forward) (SEQ ID NO: 6) and 5'-AAACCAACAATCAA-CAAAAC-3' (reverse) (SEQ ID NO: 7) corresponding to the WIF-1 promoter region sequences −488 to −468 and −310 to −290, respectively.

J. WIF-1 Expression Vectors

Several expression vectors were constructed for expression of WIF-1 polypeptides and WIF-1 subdomain polypeptides in eukaryotic and prokaryotic cells. Standard recombinant DNA technology (e.g., Sambrook & Russell, *Molecular Cloning, A Laboratory Manual* (3rd Ed, 2001); Kriegler, *Gene Transfer and Expression: A Laboratory Manual* (1990); and *Current Protocols in Molecular Biology* (Ausubel et al., eds., 1994-1999) was used to construct the following expression vectors for expression of WIF-1 in eukaryotic cells: (1) pcDNA3.1-myc-his:1-379, comprising a nucleic acid encoding a WIF-1 polypeptide as shown in SEQ ID NO:2; (2) pcDNA3.1:1-379, comprising a nucleic acid encoding a WIF-1 polypeptide as shown in SEQ ID NO:2 and expressing a WIF-1 polypeptide as shown in SEQ ID NO:30 (after cleavage of signal peptide; (3) pcDNA3.1:1-180, comprising a nucleic acid encoding a WIF-1 polypeptide as shown in SEQ ID NO:26 and expressing a WIF-1 polypeptide as shown in SEQ ID NO:27 (after cleavage of the signal peptide); (4) pcDNA3.1:1-176, comprising a nucleic acid encoding a WIF-1 polypeptide as shown in SEQ ID NO:28 and expressing a WIF-1 polypeptide as shown in SEQ ID NO:29 (after cleavage of signal peptide; and (5) Adenoviral vector:1-379, comprising a nucleic acid encoding a WIF-1 polypeptide as shown in SEQ ID NO:2 and expressing a WIF-1 polypeptide as shown in SEQ ID NO:30 (after cleavage of signal peptide. For expression in prokaryotic cells, (1) pColdI:29-379, encoding and expressing a His-tagged WIF-1 polypeptide comprising the sequence of SEQ ID NO:30 and (2) pColdI:29-180, encoding and expressing a His-tagged WIF-1 polypeptide comprising the sequence of SEQ ID NO:27.

K. WIF-1 Polypeptide Expression in Bacteria

A WIF subdomain polypeptide as shown in SEQ ID NO:27 and a full-length WIF-1 polypeptide as shown in SEQ ID NO:30 were produced in *E. coli*. The respective coding regions were inserted in the pColdI vector and the WIF-1 polypeptides were expressed with a N-terminal His tag and expressed in *E. Coli* (Strain: BL21 DE3). Both proteins were extracted from bacterial lysates and purified using a Nickle NTA column. WIF-1 polypeptides were verified by Western blotting using both anti-WIF-1 and anti-His antibodies (R&D, Santa Cruz Biotechnology). Quantification of WIF-1 polypeptides was done by both SDS-PAGE gel (Coomassie assay) and BCA protein quantification assay.

L. WIF-1 Polypeptide Expression Using Adenoviral Vectors

A coding region for WIF-1 full-length polypeptide (amino acid residues 1-379 of SEQ ID NO:2) was cloned into an adenoviral vector. The recombinant adenoviral vector was used to infect HEK-293 cells. The supernatant were concentrated (10×) and then validated by Western blotting using an anti-human WIF-1 monoclonal antibody (R&D). Dose— (200 µl, 100 µl, 40 µl) and time-dependent apoptosis was noticed in both melanoma cell line LOX and lung cancer cell lines H460 and A427 (data not shown). The blockade of Wnt signaling pathway was confirmed by Western analysis of several key proteins in the pathway, e.g., DVL-3, β-catenine, cyclin D1, etc.

M. Protein Glycosylation Analysis of WIF-1

Protein glycosylation analysis of WIF-1 proteins was performed. Glycosylation assays were carried out using the GlycoProfile III Kit (Sigma Chemical) according to the manufacturer's instruction. Protein glycosylation was not detected on WIF-1 proteins (full-length WIF-1 polypeptide and WIF-1 subdomain polypeptide) produced and extracted from bacteria or from a commercial WIF-1 protein from Abnova Biotech, Inc. (data not shown). However, full-length recombinant WIF-1 polypeptide and recombinant WIF-1 subdomain polypeptide purified from transfected 293T cells showed glycosylation (data not shown).

N. Statistical Analysis

Unpaired t-test in Excel was used for comparing activities of different constructs and treatments.

Example 2

Identification of the WIF-1 Promoter Region

To identify the WIF-1 promoter, a BLAST search was conducted using the 1140-bp coding sequence of WIF-1 as a virtual probe against the human genomic database at the UCSCr. A promoter search program was used to confirm that the 5' region of the gene presents classical features of a promoter region. In addition, a CpG island search program was used to map the CpG islands within the WIF-1 promoter (FIG. 1). 105 CpGs in this promoter region (1.2 kb before the ATG of the WIF-1 open reading frame) were identified.

Example 3

Functional Analysis of the Human WIF-1 Promoter with Deletion Mutants

To study the promoter activity the complete 1 kb fragment (ahead of the ATG) as well as five truncated fragments were cloned into a promoterless luciferase (LUC) expression vector pGL3Basic. 293T cells were transfected with those constructs and examined LUC activities. The complete wild type construct (construct 1) displayed a very high basal activity (approximately 200-fold increase of LUC activity compared to that of the empty vector which was set to unity).

Example 4

WIF-1 is Downregulated by Promoter Hypermethylation in Cancer Cells

Figure 2A:
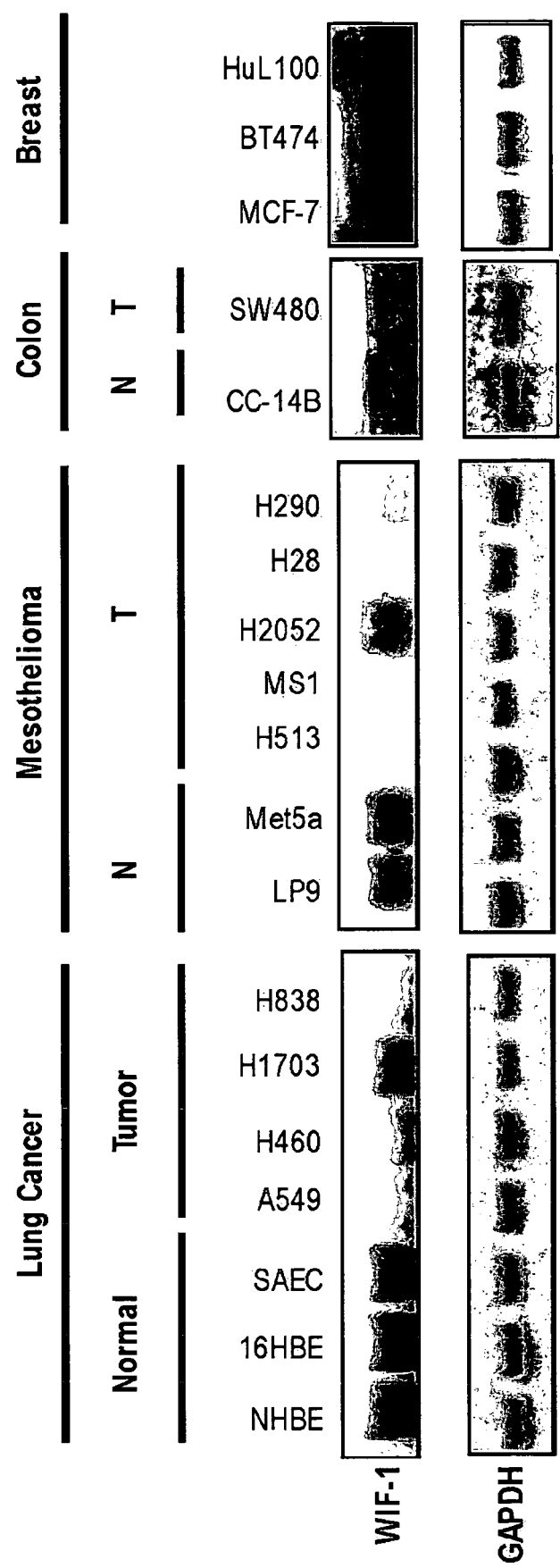
FIG. 2A shows WIF-1 expression in human cancer cell lines. N, normal cell line; T, Tumor cell line.
Figure 2B:
FIG. 2B shows methylation analysis of the human WIF-1 promoter in different cell lines (MSP). U, unmethylated; M, methylated.
Figure 3A:
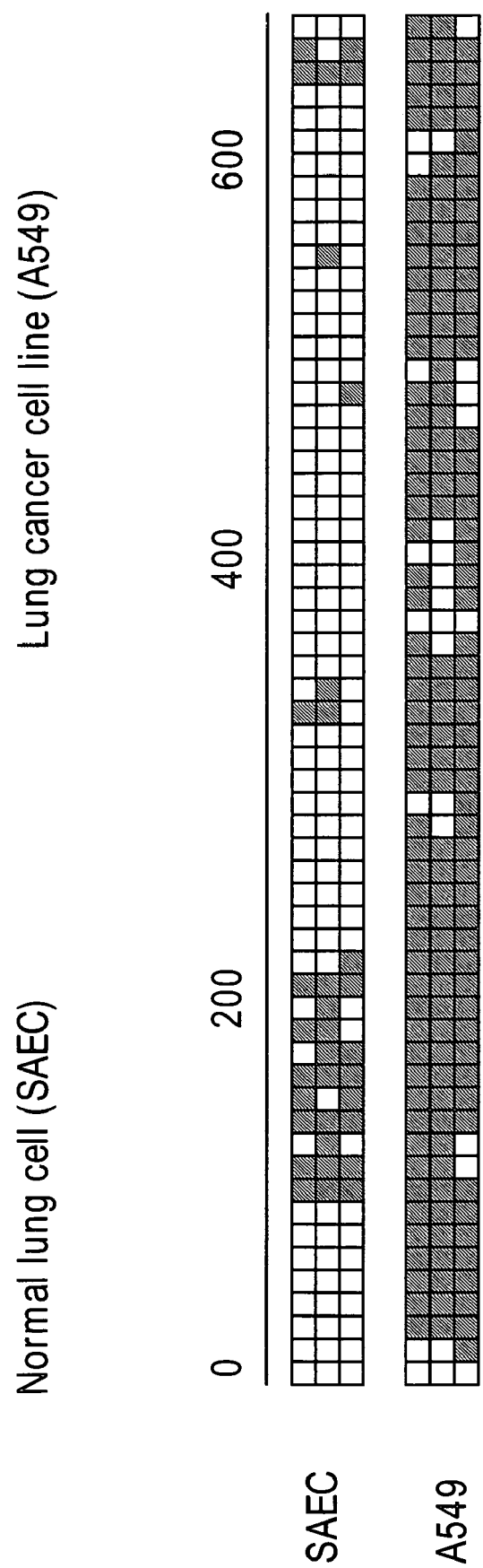
FIG. 3A shows a methylation analysis of the human WIF 1 promoter (Bisulfate sequencing).
Figure 3B:
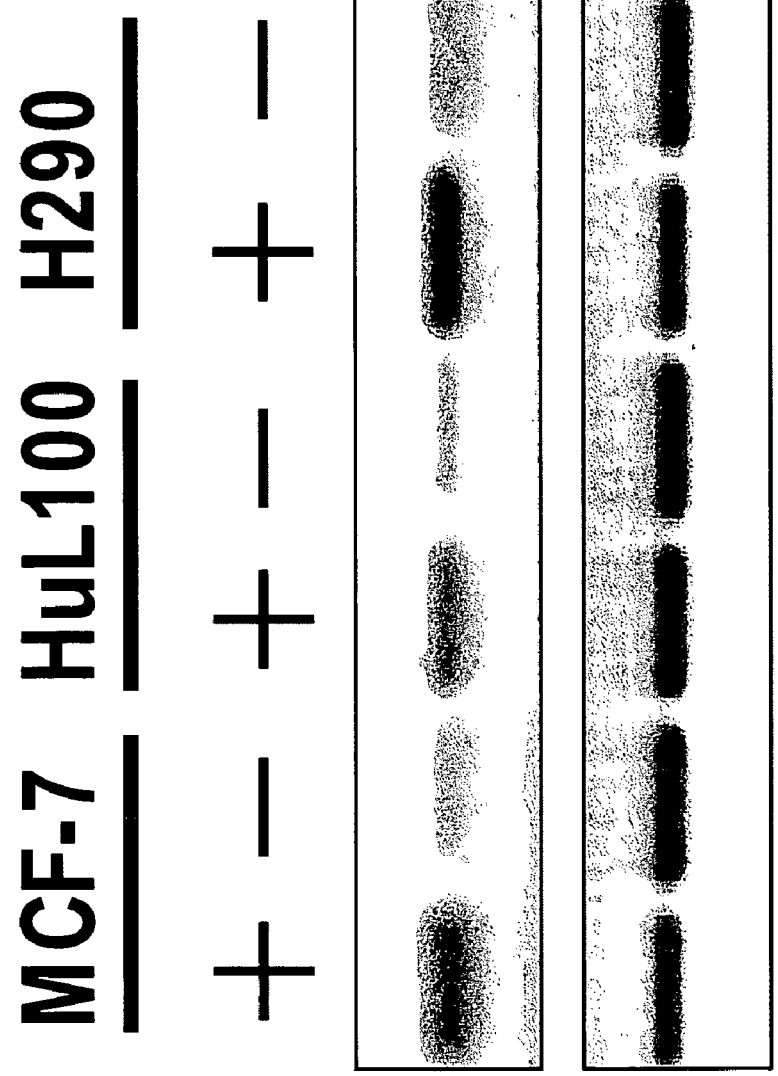
FIG. 3B shows reactivation of WIF-1 expression by de-methylating agent 5-aza-2'-deoxycytidine (DAC) treatment in different cell lines.
Figure 17:
FIG. 17 shows WIF-1 protein expression in normal and cancer cells. WIF-1 protein is expressed in normal primary culture cells, NHBE, SAEC and NHEK. WIF-1 protein is under-expressed in human cancer cells, including lung cancer (H460, A549), breast cancer (MCF-7), colon cancer (SW480), and mesothelioma (MS-1, H2052).

WIF-1 expression in several normal and tumor cell lines was examined using semi-quantitative RT-PCR (FIG. 2A). It was found that WIF-1 was expressed in all three normal primary cell cultures NHBE, 16 HBE and SAEC. In contrast, the WIF-1 transcript was missing or dramatically under-expressed in three of four NSCLC cell lines. Next the methylation status of the CpG islands in these cell lines was analyzed. All cancer cell lines tested lacking WIF-1 expression were found to be hyper-methylated using methylation-specific PCR (MSP) (FIG. 2B). In contrast, no hyper-methylation was seen in all normal controls that expressed WIF-1. WIF-1 was under-expressed to a lesser extent in the H 1703 cell line and MSP only shows partial methylation in this cell line. Further, bisulfite sequencing was used to analyze details of the methylation status of 60 CpG sites in the 672 bp fragment of WIF-1 including the promoter from −554 to ATG and a part of the first exon from ATG to +118 in several cell lines (FIG. 3A). Consistent with MSP results, it was found that these CpG islands were densely methylated in all the NSCLC cell lines tested. In addition, it was found that the WIF-1 expression was restored after the demethylating agent DAC treatment in those cell lines lacking WIF-1 expression (FIG. 3B). The down-regulated WIF-1 mRNA levels in normal and cancer cells correlated with WIF-1 protein level in these cells. It was found that WIF-1 protein is expressed in normal primary culture cells (NHBE, SAEC and NHEK) (FIG. 17). However, WIF-1 protein is under-expressed in human cancer cells, including lung cancer (H460, A549), breast cancer (MCF-7), colon cancer (SW480), and mesothelioma (MS-1, H2052) (FIG. 17). These results show that the status of WIF-1 expression in NSCLC cell lines correlates with dense CpG methylation of the WIF-1 promoter region.

Example 5

Figure 4B:
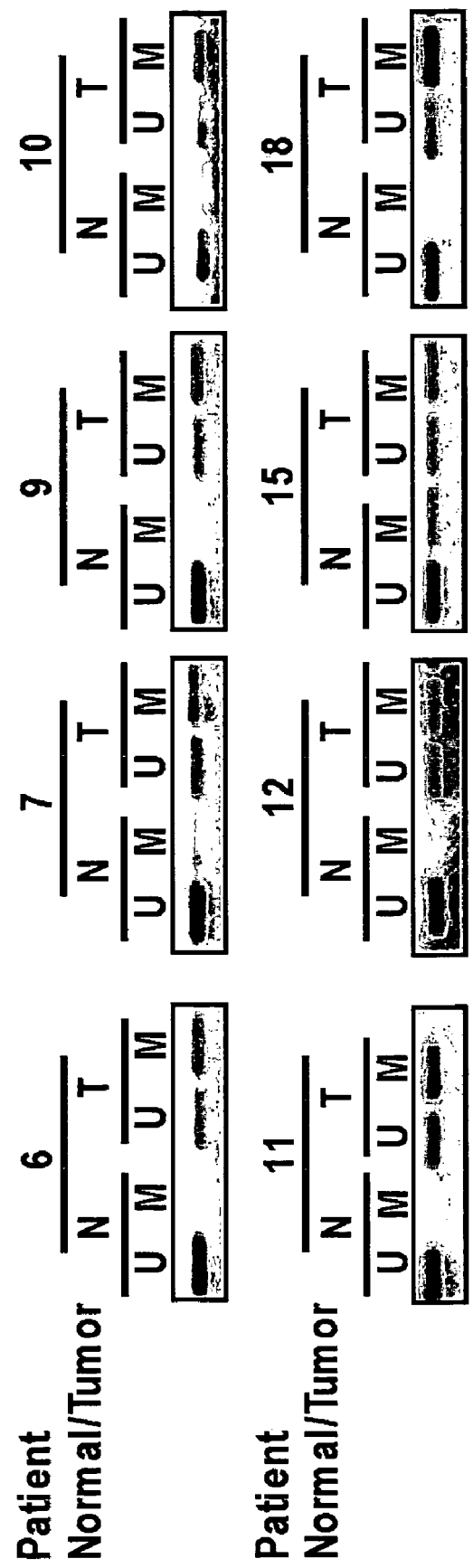
FIG. 4B shows a methylation analysis of the WIF-1 promoter in primary human lung cancer tissue samples (MSP).
Figure 4C:
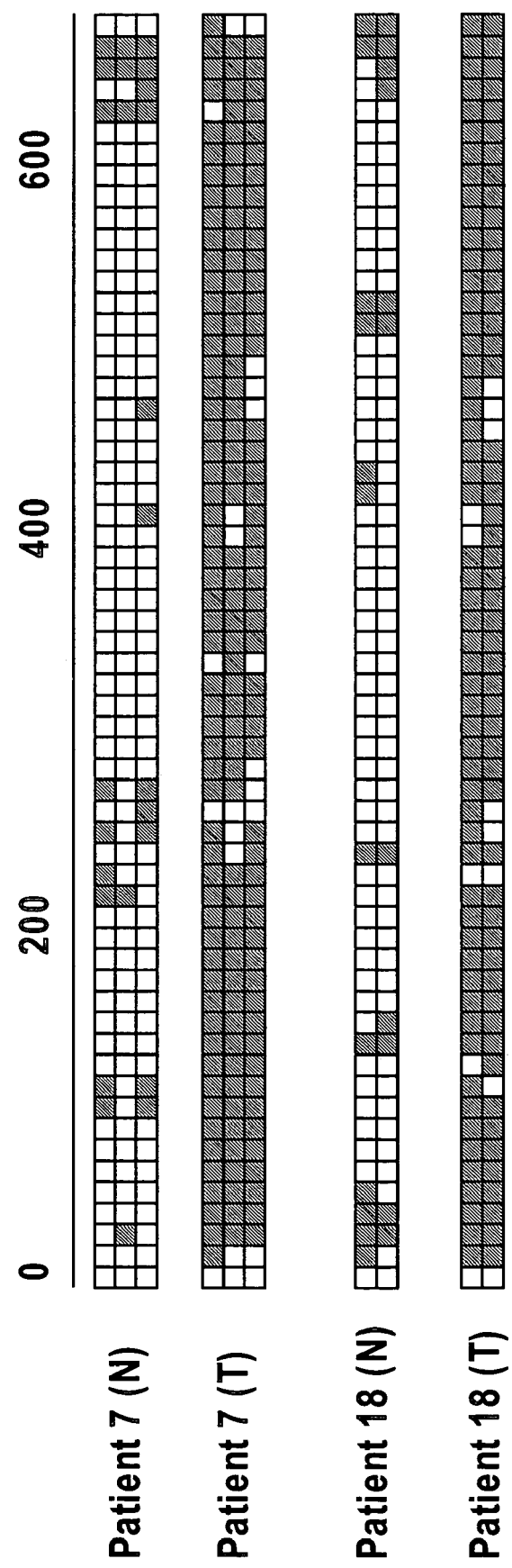
FIG. 4C shows a methylation analysis of the WIF-1 promoter in primary human lung cancer tissue samples (Bisulfite sequencing).

WIF-1 is Downregulated by Promoter Hypermethylation in Fresh Human NSCLC Tissue Samples WIF-1 expression and methylation status was analyzed in primary NSCLC tissue samples. Among eighteen matched pairs of surgically resected early stage lung cancers, fifteen cancer samples (83%) were found to have no or little WIF-1 mRNA as compared to their autologous normal samples (FIG. 4A). By using MSP, aberrant methylation was found in all tumor samples that lack WIF-1 expression, but not in their matched normal samples (FIG. 4B). This correlation was demonstrated in 8 cases for which both RNA and bisulfite-treated genomic DNA were available (patients 6, 7, 9, 10, 11, 12, 15, 18). In addition, MSP was performed in 8 additional matched samples (patients 19 to 26) and evidence of methylation in 7 of them was found. In several cases, slight methylated as well as unmethylated bands were observed respectively in normal and tumor tissues probably due to unavoidable contamination of cancer cells in the non-cancer specimen or pre-malignant changes of peri-tumoral normal tissue. These data show that silencing of WIF-1 is correlated with hyper-methylation of its promoter in primary NSCLC tissue samples. In addition, sequences of the WIF-1 promoter region after bisulfite treatment for numerous samples were analyzed. Dense methylation in those CpG sites (FIG. 4C) was detected. In summary, WIF-1 is frequently downregulated in NSCLC and this downregulation is correlated with the promoter hypermethylation.

Example 6

Restoration of WIF-1 Induces Apoptotic Cell Death

Figure 5:
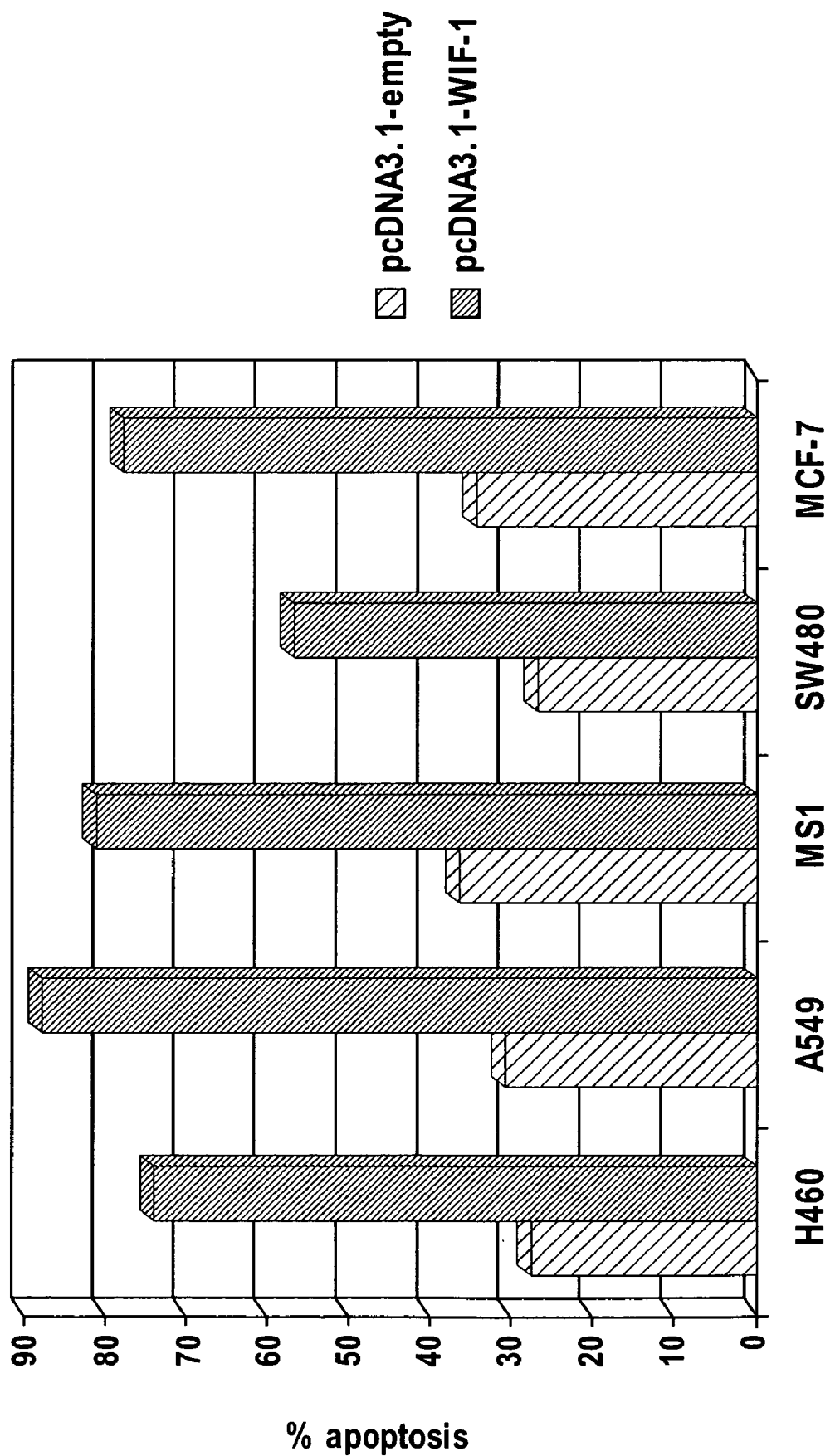
FIG. 5 shows WIF-1 transfection in various cancer cell lines.

Whether restoration of WIF-1 could cause growth suppression in the lung cancer cell lines where the WIF-1 gene was downregulated by promoter hyper-methylation was demonstrated. One week after transfection and subsequent drug selection, a dramatic decrease of live cell numbers in the WIF-1-transfected H460, A549 MS1, SW480, H28 and MCF7 cells compared to the empty vector-transfected control transfectants (P<0.005) was found (FIG. 5). Flow cytometry analysis showed a significantly higher level of apoptosis induction in WIF-1-transfected H460, A549 and H28 cells where WIF-1 was methylation-silenced (approximately 57-70% at one week after transfection) than empty vector-transfected H460, A549 and H28 cells (approximately 12-26% at one week after transfection) (P<0.005) (FIG. 5). This result shows that restoration of WIF-1 expression suppresses cell growth by inducing apoptosis in those H460, A549 and H28 cells. After selection of drug-resistant colonies for four weeks, it was found that the colony numbers of WIF-1 transfected cells decreased compared to that of empty vector-transfected cells (P<0.005).

WIF-1 is known to bind Wnt proteins and to inhibit their activities (Hsieh et al., *Proc. Natl. Acad. Sci USA* 96(7):3546-51 (1999)). Recently, Wissman et al. reported by using a microarray analysis the downregulation of WIF-1 in several human cancers and confirmed the latter by immunohistochemistry in 60% of breast cancers and 75% of lung cancers. In this application, the downregulation of WIF-1 in NSCLC cell lines at a transcriptional level is reported. Moreover, it has been found that WIF-1 was also downregulated in 83% of fresh NSCLC surgical specimen when compared to normal tissue. WIF-1 silencing correlates with its promoter hyper-methylation in both cancer cell lines and human NSCLC primary tissues.

We propose that WIF-1 downregulation occurs in NSCLC through an epigenetic regulation as previously reported for sFRP in colorectal carcinoma. It's noteworthy that WIF-1 lacks any sequence similarity with the CRD domain of Fz or sFRP (Bui et al., *Oncogene* 14(10):1249-53 (1997); Melkonyan et al., *Proc. Natl. Acad. Sci. USA* 94(25):13636-41 (1997); Shimizu et al., *Cell. Growth Differ.* 8(12):1349-58 (1997); Todd et al., *Cancer Res.* 57(7):1344-52 (1997)). WIF-1 contains a Wnt binding domain and five epidermal growth factor-like repeats. It can bind to XWnt-8 and *Drosophila* Wg in the extracellular space and inhibit XWnt-8-Dfz interactions (Hsieh et al., *Proc. Natl. Acad. Sci. USA* 96(7): 3546-51 (1999)). The mechanism by which WIF interact with Wnt remains partially understood. Tcf responsive elements in the WIF-1 promoter were identified (data not shown) suggesting that WIF-1 can act as a negative feedback regulator of Wnt signaling.

Aberrant methylation of promoter regions that downregulates transcription of the genes has been recognized as a mechanism for inactivating tumor suppressor genes in human cancer. In lung cancer, p16 was first reported to be methylated. Now, many other genes such as APC, H-Cadherin, Glutathion S-Transferase, Retinoic acid receptor β-2, E-Cadherin, RAS association domain family 1A have been shown to be methylated in various type of lung cancer and recently hypermethylation of the human SOCS-3 promoter in NSCLC cells was reported (Altieri, *Nat. Rev. Cancer* 3(1):46-54 (2003); Blanc-Brude et al., *Clin. Cancer Res.* 9(7):2683-92 (2003); Bowen et al., *J. Invest. Dermatol.* 120(1):48-55 (2003); Cong et al., *Mol. Cell. Biol.* 23(23):8462-70 (2003); Deng et al., *Cell* 115(1):61-70 (2003); He et al., *Neoplasia In Press* (2003); Ishitani et al., *Mol. Cell. Biol.* 23(1):131-9 (2003); Kawano and Kypta, *J. Cell. Sci.* 116 (Pt 13):2627-34 (2003); Kim et al., *Lancet* 362(9379):205-9 (2003); Krilleke et al., *Int. J. Cancer* 107(4):520-7 (2003); Pham et al., *Mol. Pathol.* 56(5)280-5 (2003); Soengas and Lowe, *Oncogene* 22(20):3138-51 (2003); Topol et al., *J. Cell. Biol.* 162(5):899-908 (2003); Uematsu et al., *Oncogene* 22(46):7218-21 (2003); Uematsu et al., *Cancer Res.* 63(15):4547-51 (2003); Usami et al., *Oncogene* 22(39):5978-86 (2003); Veeman et al., *Dev. Cell.* 5(3):367-77 (2003); Westfall et al., *J. Cell Biol.*

162(5):889-98; and Wong et al., *Mol. Cell.* 12(5):1251-60 (2003)). The findings of WIF-1 silencing by promoter methylation as described herein, reveal an important epigenetic event during the development of NSCLC suggesting that WIF-1 may be a key antagonist of Wnt signaling in lung cancer.

Figure 22:
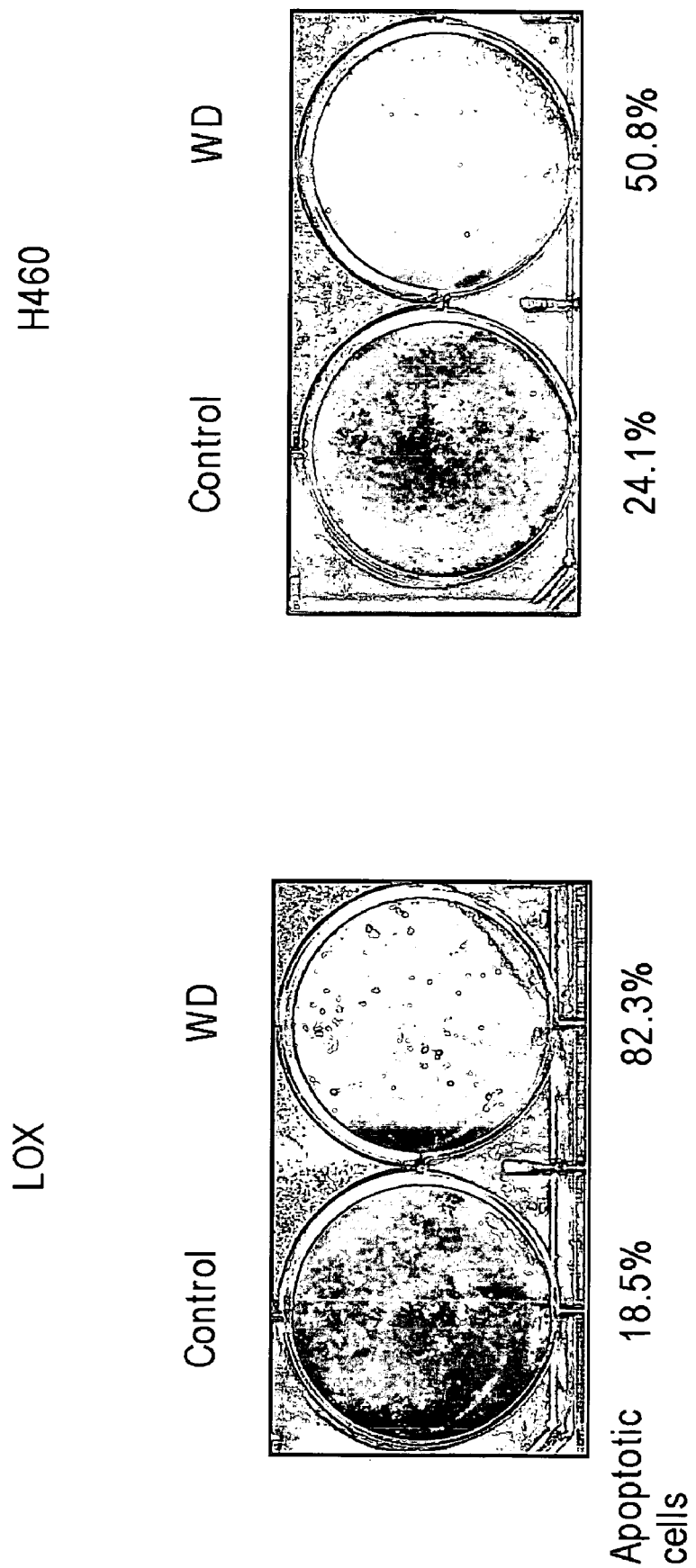
FIG. 22 shows the percentage of apoptotic cells and the cytotoxicity effect of recombinant human WIF-1 subdomain polypeptide (SEQ ID NO:26) on the melanoma cell line LOX and lung cancer cell line H460.
Figure 23:
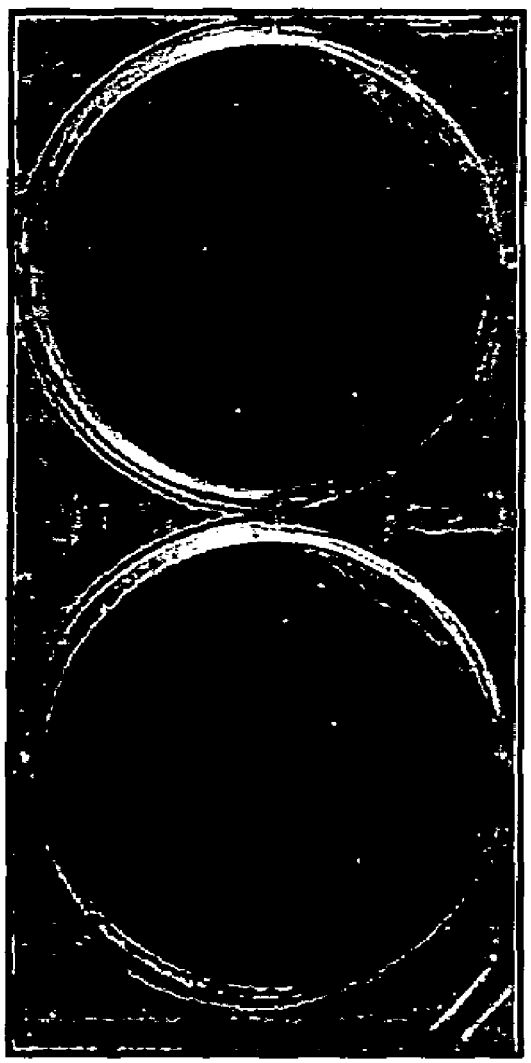
FIG. 23 shows the percentage of apoptotic cells and the cytotoxicity effect of recombinant human WIF-1 subdomain polypeptide (SEQ ID NO:27) on the melanoma cell line LOX.
Figure 24:
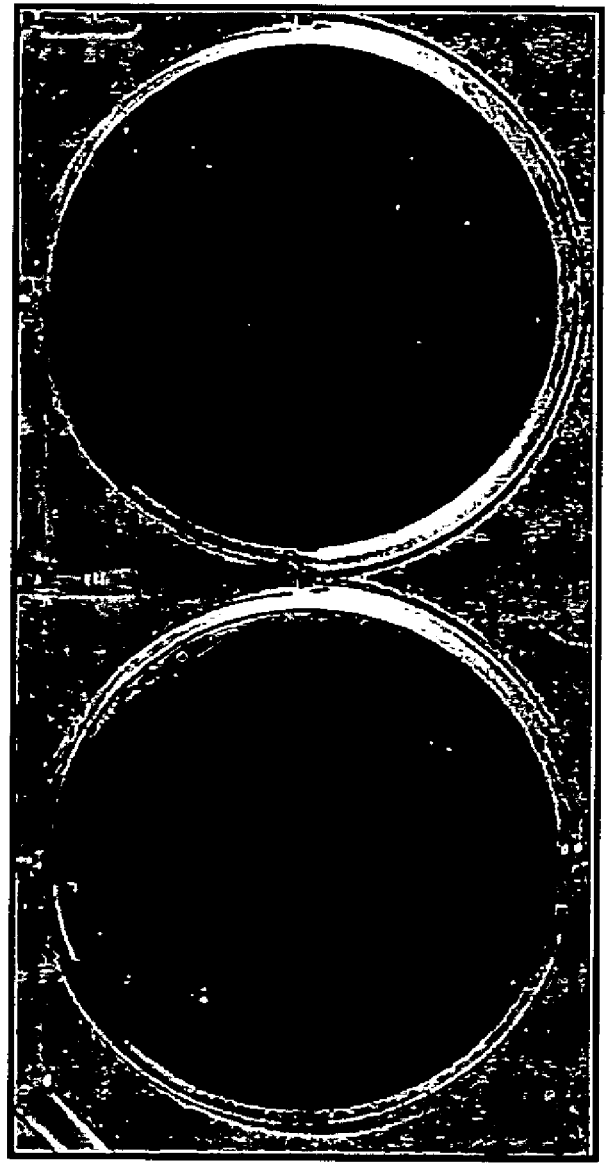
FIG. 24 shows the percentage of apoptotic cells and the cytotoxicity effect of recombinant mature human WIF-1 polypeptide (SEQ ID NO:30) on the melanoma cell line LOX.

It has also been found that expression of WIF-1 induces apoptosis in various human cancer cell lines, including the lung cancer cell lines A427, A549, and H460, the mammary carcinoma cell line MCF-7, the colon cancer cell line SW480, and the mesothelioma cell lines MS-1 and H28. Furthermore, WIF domain (WD) polypeptide, a functional Wnt-binding subdomain of WIF-1 comprising amino acids 39-176 of a WIF-1 polypeptide as shown in SEQ ID NO:2, induces dose-dependent apoptosis in lung cancer cell line A427. WIF-1 polypeptide induces dose-dependent apoptosis in the lung cancer cell line H460; purified recombinant human WIF-1 protein induces dose-dependent apoptosis in the lung cancer cell line H460; WIF-1 polypeptide induces dose-dependent apoptosis in the melanoma cell lines LOX (FIG. 24) nd FEMX; and WD polypeptide induces dose-dependent apoptosis in melanoma cell line LOX and H460 (FIGS. 22 and 23). Moreover, recombinant human WIF-1 protein inhibits the Wnt signaling pathway in lung cancer cell line H460.

Taken together, the findings described herein show that WIF-1 silencing occurs as a result of promoter hypermethylation and may be an important cause of constitutive activation of the Wnt pathway in cancer and especially in lung cancer. These findings reinforce the therapeutic potential of inhibiting the Wnt signaling pathway through strategy such as antibody blockade and raise the interest of reversing WIF-1 inactivation by demethylating agents. Such strategies are of particular interest in NSCLC for which Wnt pathway appears to be of paramount importance and current treatments remain disappointing.

Example 7

Figure 6A:
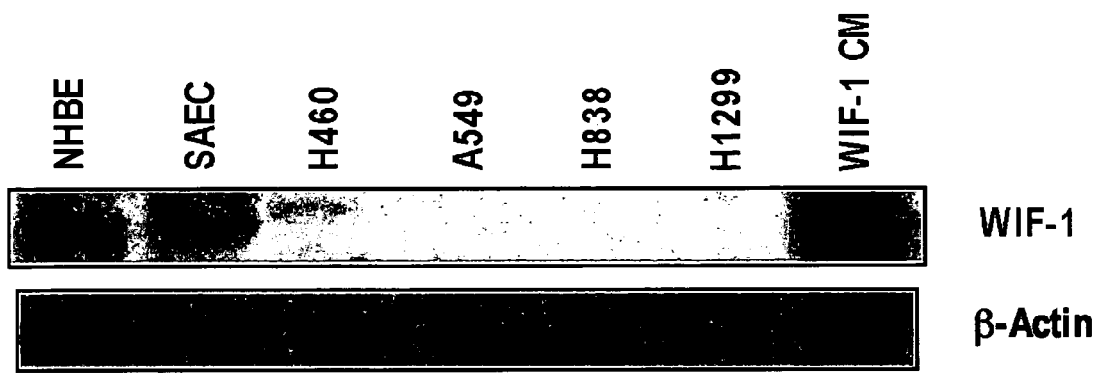
FIG. 6 shows that transfection of human WIF-1 cDNA increases apoptosis and inhibits Wnt signaling in NSCLC cell lines. Panel A shows a Western analysis of WIF-1 expression in NSCLC cell lines H460, A549, H838, and H1299. WIF-1 expression was observed both in normal human primary human bronchial epithelial cells (NHBE) and small airway epithelial cells (SAEC) and WIF-1 CM from 293T cells was used as a positive control. β-Actin was used as loading control. Panel B shows that transfection of WIF-1 cDNA plasmid (dark bar) into NSCLC cell lines A549 and H460 causes dramatically more apoptotic cell population (5 days after transfection). Empty vector was used as transfection control (light bar). Panel C shows a Western analysis after WIF-1 plasmid transfection ("+"; 72 hrs after transfection); empty vector served as control ("−"). β-catenin and Survivin were tested. β-Actin was used as a loading control.
Figure 6B:
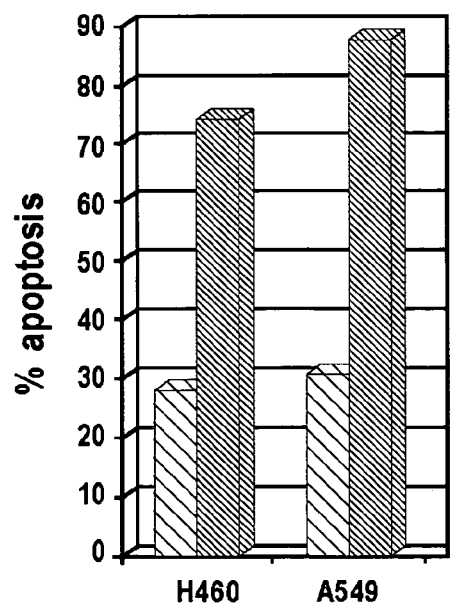
Figure 6C:
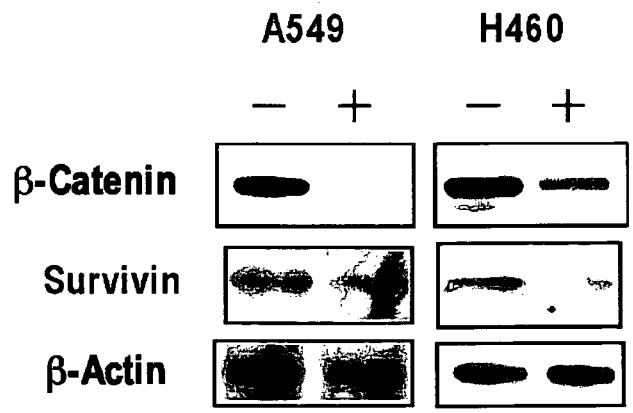
Figure 9:
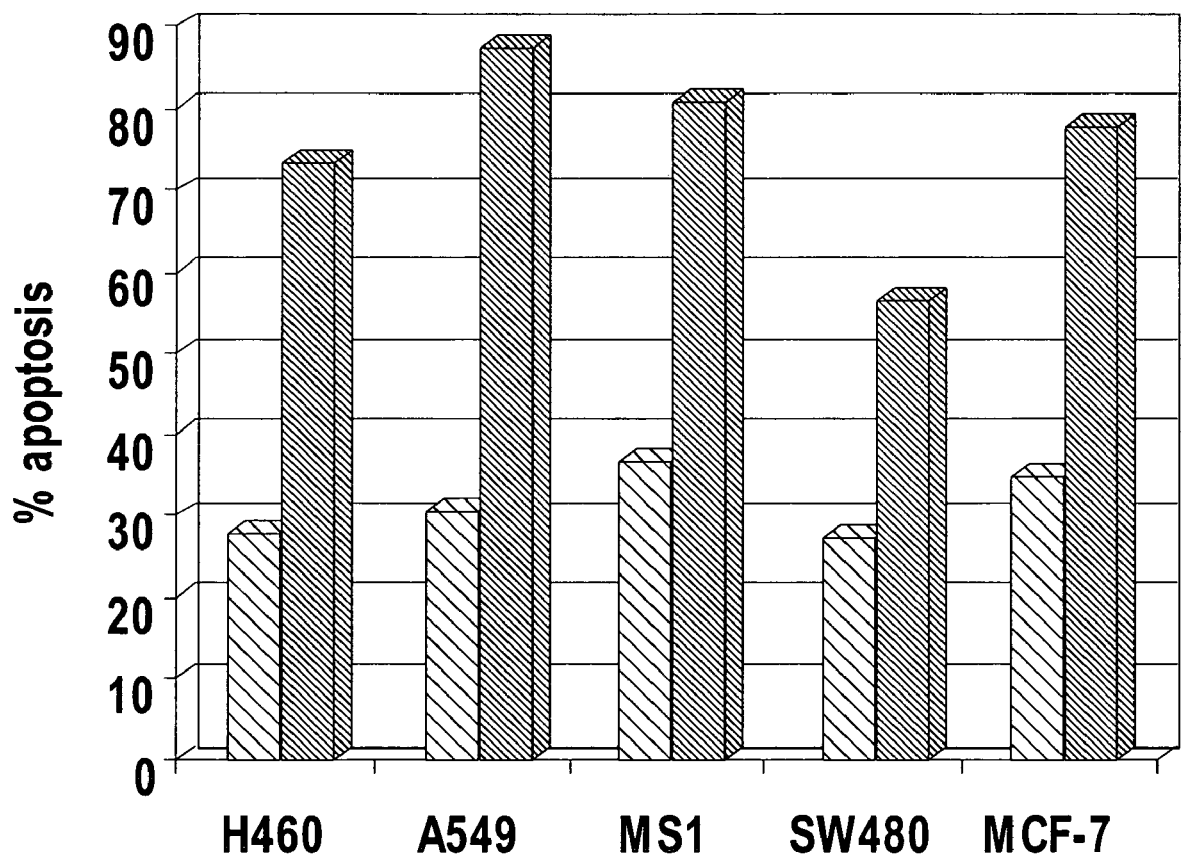
FIG. 9 shows that WIF-1 re-expression induces apoptosis in various human cancer cell lines. The indicated cell lines were transfected with pcDNA3.1-empty (light bars) or with pcDNA3.1-WIF-1 (dark bars) and % apoptosis was determined.

Transfection of WIF-1 cDNA Induces Apoptosis and Inhibits WNT Signaling in Cancer Cell Lines To demonstrate that WIF-1 can induce apoptosis and block Wnt signaling in NSCLC cell lines, WIF-1 polypeptide encoding plasmid were transfected into cell lines H460 and A549. Human WIF-1 open reading frame was cloned into the mammalian expression vector pcDNA3.1 for the re-expression of WIF-1 protein in NSCLC cells. Expression vectors used in this study either comprised a nucleic acid encoding the full-length WIF-1 polypeptide of SEQ ID NO:2 or a WIF-1 subdomain polypeptide as shown in SEQ ID NO:26. First, the under-expression of WIF-1 was confirmed at protein level when compared with SAEC cells, NHBC cells and WIF-1 serum free CM from 293T cells (control; FIG. 6A). Five days after transfection, a dramatically increased apoptotic cell death in both cell lines was observed (FIG. 6B). Further, the key mediator of Wnt canonical signal pathway, cytosolic β-catenin, was down-regulated (FIG. 6C). In addition, an inhibitor of apoptosis protein, Survivin, was also down-regulated in A549 and H460 cells after WIF-1 transfection. Survivin is an important down stream gene in the Wnt signaling pathway (He et al., *Neoplasia* 6:7-14 (2004); You et al., *Oncogene* 23:6170-6174 (2004)). These results show that re-expression of WIF-1 protein induces programmed cell death in the NSCLC cell lines H460 and A549 through inhibition of the Wnt signaling pathway. In addition, re-expression of WIF-1 induced apoptosis in the mesothelioma cell lines MS1 and H28, in the colon cancer cell line SW480, and in the mammary carcinoma cell line MCF-7 (FIG. 9).

Example 8

Figure 10:
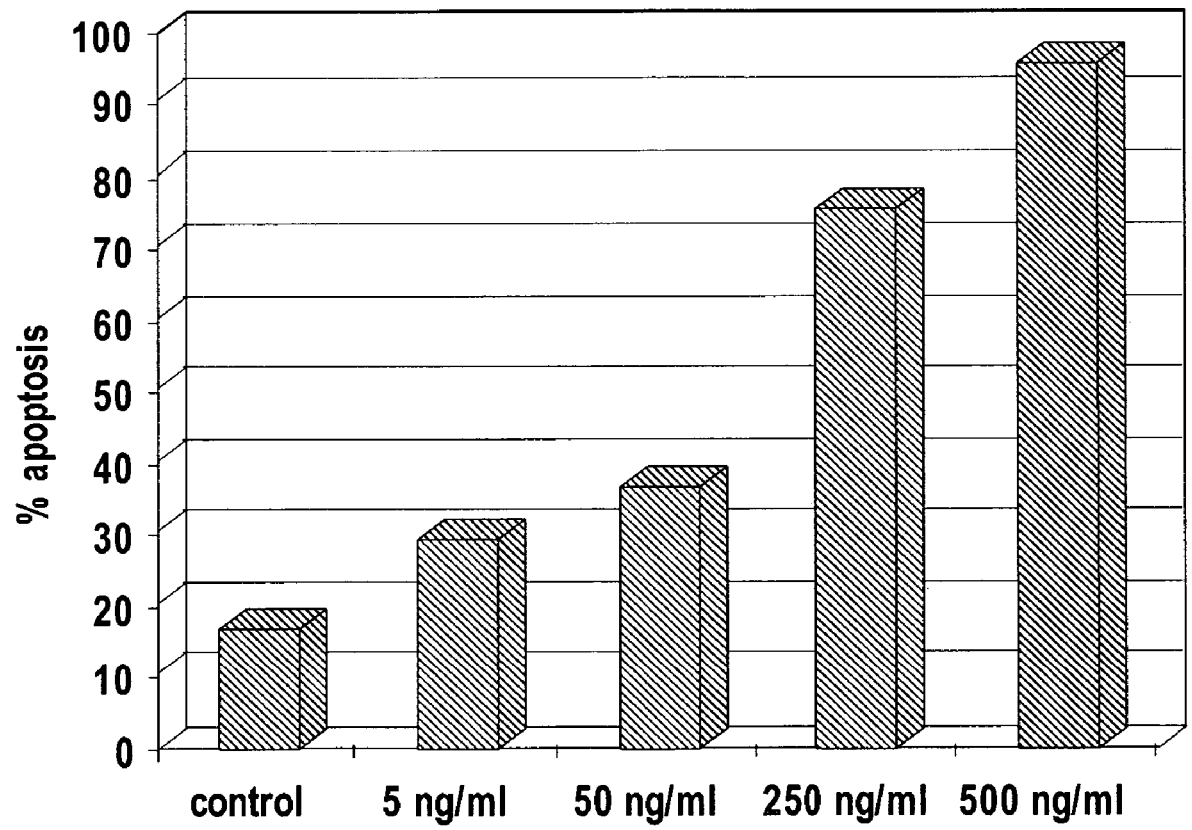
FIG. 10 shows that recombinant WIF-1 protein from serum-free conditional medium induces dose-dependent apoptosis in the lung cancer cell line H460.
Figure 21:
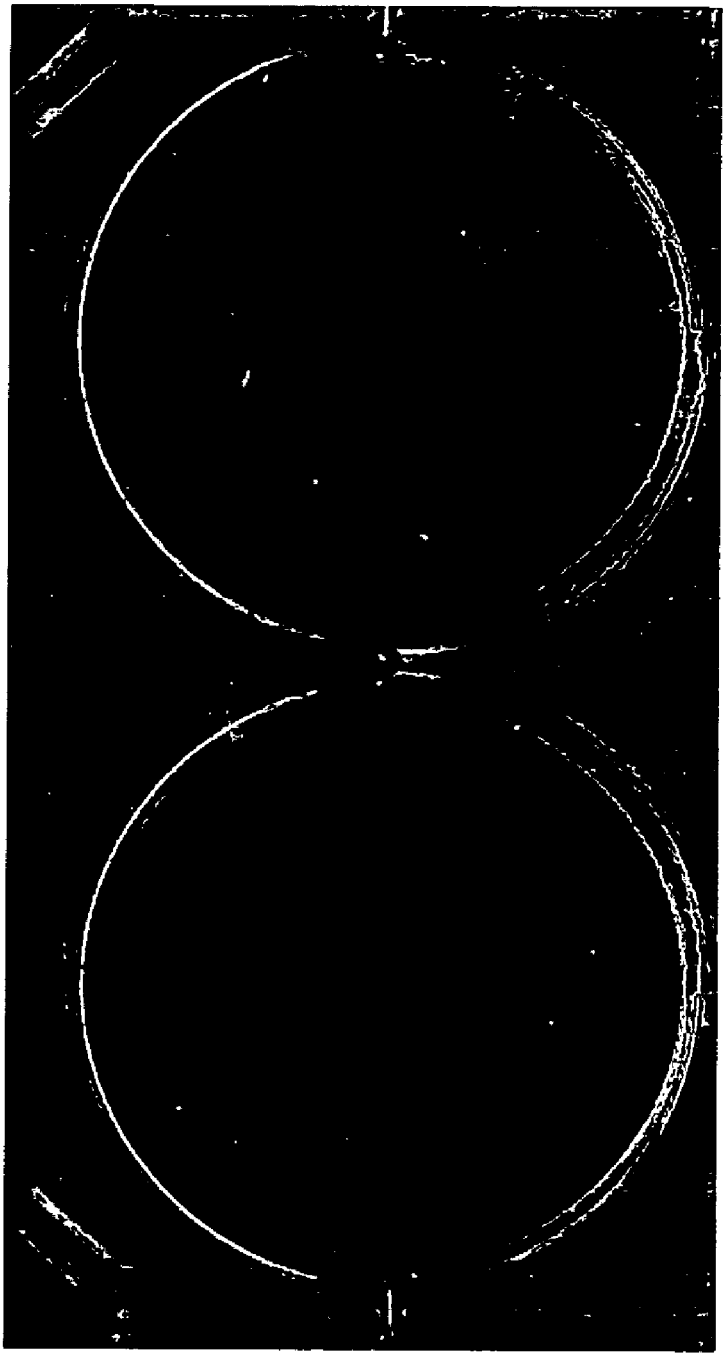
FIG. 21 shows the cytotoxicity effect of recombinant full-length human WIF-1 polypeptide (SEQ ID NO:2) in the colorectal cancer cell line HCT-116. 0.5% Crystal Violet staining of HCT-116 cells at 4 days after adding 200 µl CM comprising recombinant full-length human WIF-1 polypeptide (SEQ ID NO:2), almost 100% cell killing was observed. Viable cells are stained.

Serum-Free Conditioned Medium from Cells Transfected with a WIF-1 Expression Plasmid Induces Apoptosis in Cancer Cell Lines To further verify the apoptosis effect induced by WIF-1 in NSCLC cells, WIF-1 Serum-Free CM was used to treat cell lines H460, A549, and H838. Recombinant human full-length WIF-1 CM was produced via transient transfection. WIF-1 protein in serum-free CM was confirmed by Western blot analysis (FIG. 6A). Five days after incubation, a dramatically increased cell death in NSCLC cell lines H460, A549 and H838 was observed (FIG. 7A). Flow cytometry experiments indicate that the cell death was mainly due to apoptosis induction (>80% of apoptotic cells after 5-7 days of incubation) (FIG. 7B). Moreover, the apoptosis induction was dose-dependent in all three NSCLC cell lines tested, e.g., the dose-response relationship between WIF-1 and apoptosis induction in H460 cells is shown in FIG. 7C and FIG. 10. A dose-response inhibition of Wnt signaling correlated with the level of apoptosis induced by WIF-1 CM (FIG. 7D). Both the cytosolic β-catenin and Survivin were down-regulated (FIG. 7D). Furthermore, a key down-stream gene of Wnt signaling, cyclin D1, was down-regulated after WIF-1 CM treatment (FIG. 7D). Over-expression of cytochrome C served as additional evidence of apoptotic cells induced by WIF-1 CM. These data show that WIF-1 CM inhibits the Wnt signaling pathway and induces apoptosis in a dose-dependent fashion. Recombinant full-length human WIF-1 polypeptide also induced apoptosis in a dose-dependent manner in the hepatocellular cell line SNU398 and in the colorectal cancer cell line HCT-116 (FIGS. 20 and 21).

Example 9

Figure 12:
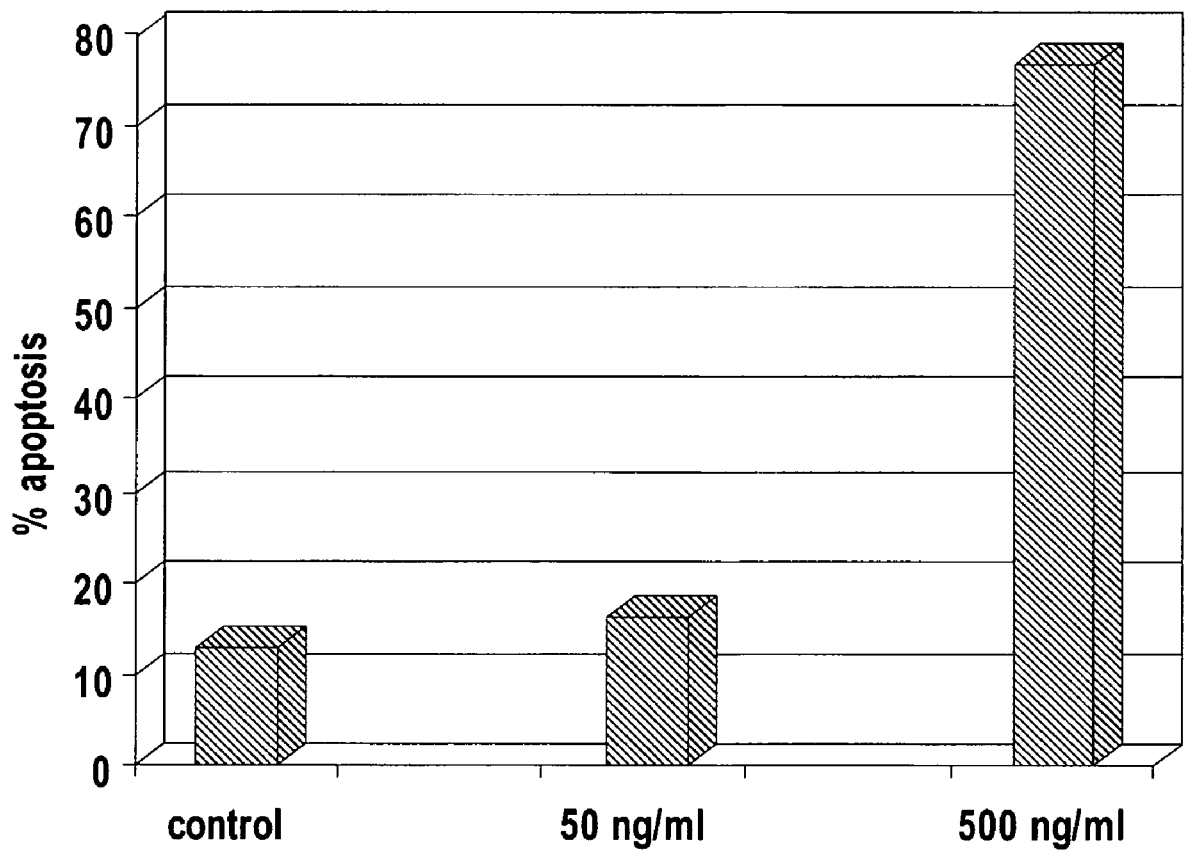
FIG. 12 shows that recombinant WIF-1 domain (WD) protein from serum-free conditional medium induces dose-dependent apoptosis in the lung cancer cell line A427.
Figure 13:
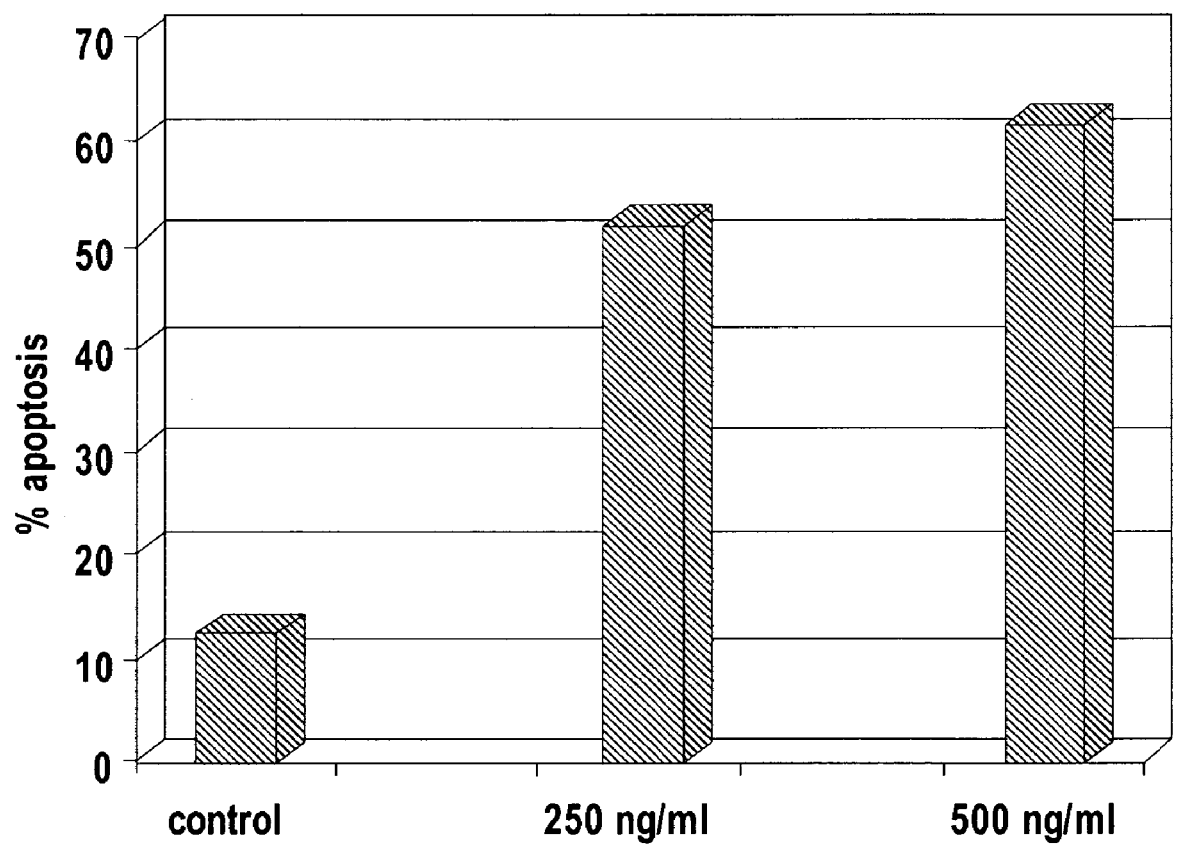
FIG. 13 shows that recombinant WIF-1 protein from serum-free conditional medium induces dose-dependent apoptosis in the melanoma cell line LOX.

Serum-Free Conditioned Medium from Cells Transfected with a WIF-1 (WD) Expression Plasmid Induces Apoptosis To demonstrate that the apoptotic effect of WIF-1 is not limited to the full-length WIF-1, the lung cancer cell line A427 was incubated with serum-free conditioned medium from cells transfected with a WIF-1 (WD) expression plasmid (prepared as described herein). This expression plasmid encodes a functional WIF-1 subdomain polypeptide comprising amino acid residues 1-180, which after cleavage of the signal peptide comprises the amino acid sequence shown in SEQ ID NO:27. It was found that this WIF-1 (WD) polypeptide also induced apoptosis in the lung cancer cell line A427 (FIG. 12).

The recombinant WIF-1 subdomain polypeptide of SEQ ID NO:27 did also show a significant cytotoxicity effect when added to the melanoma cancer cell line LOX and the lung cancer cell line H460 (FIGS. 22 and 23).

Example 10

Figure 14:
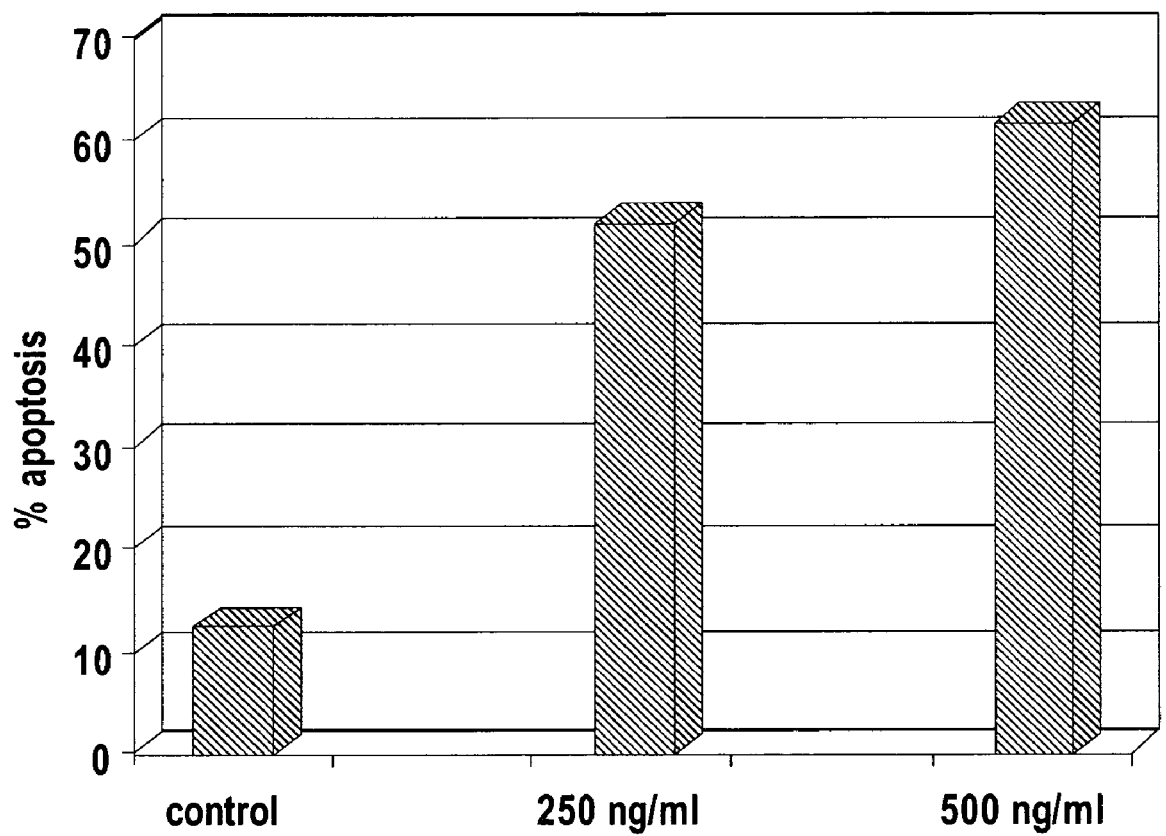
FIG. 14 shows that recombinant WIF-1 protein from serum-free conditional medium induces dose-dependent apoptosis in the melanoma cell line FEMX.
Figure 15:
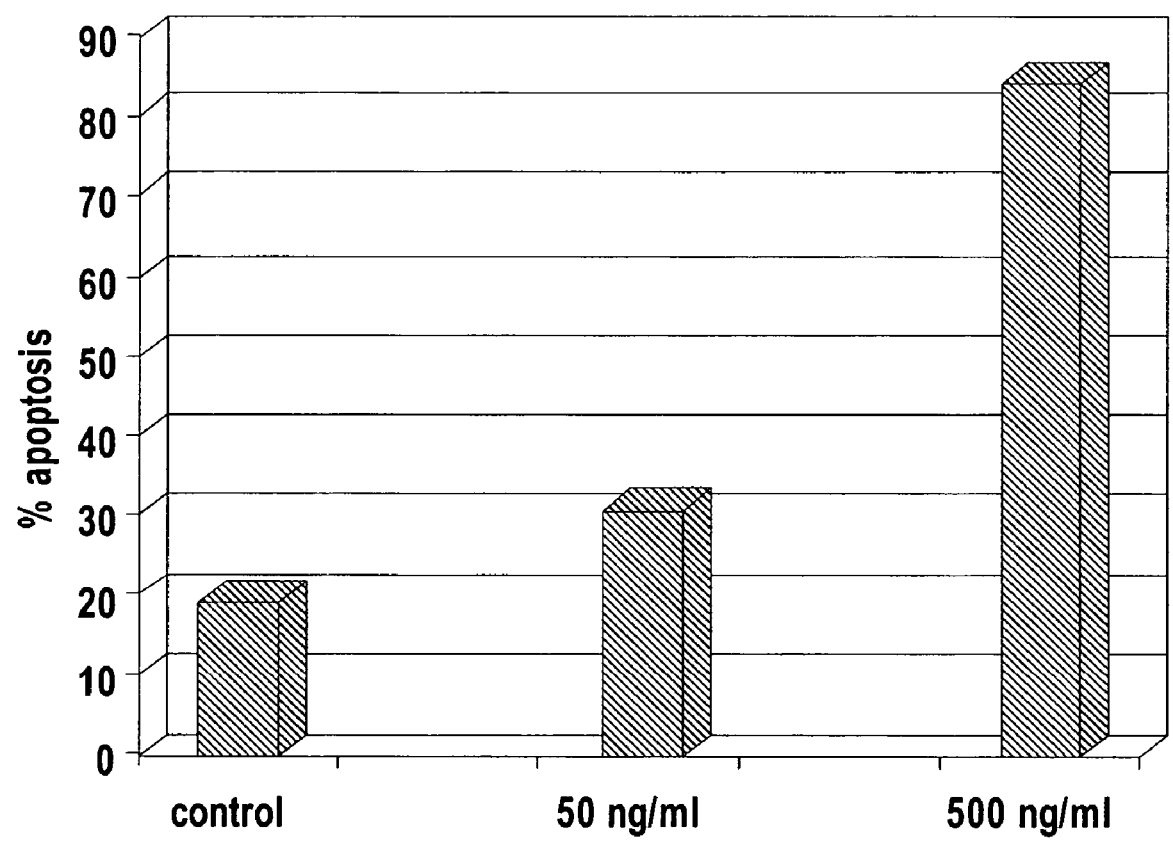
FIG. 15 shows that recombinant WIF-1 domain (WD) protein from serum-free conditional medium induces dose-dependent apoptosis in the melanoma cell line LOX.
Figure 16:
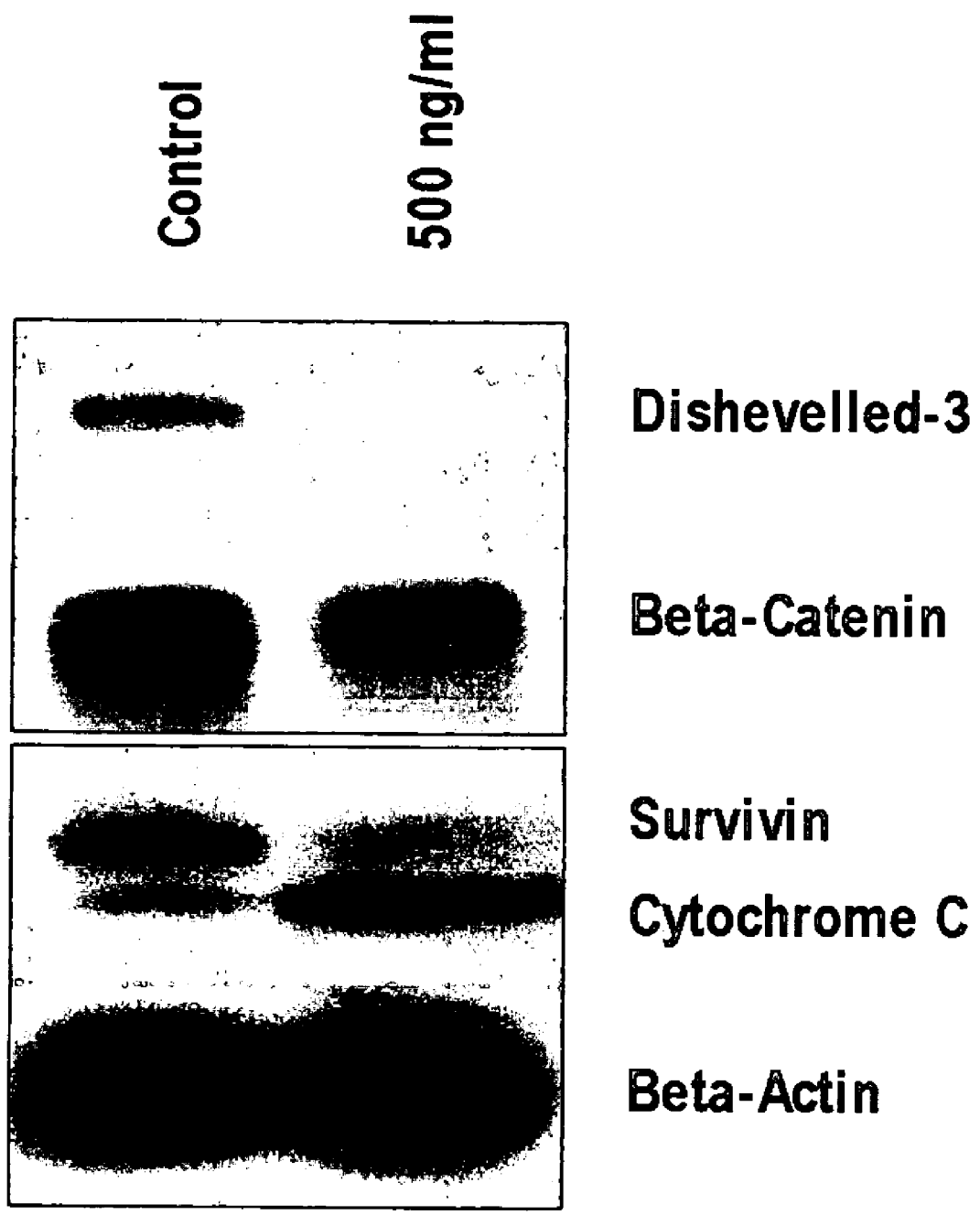
FIG. 16 shows that recombinant WIF-1 domain (WD) protein inhibits Wnt signaling pathway in the melanoma cell line LOX. Expression of dishevelled-3, β-catenin, Survivin, and Cytochrome C was analyzed. β-Actin served as a loading control.

Serum-Free Conditioned Medium from Cells Transfected with a WIF-1 Expression Plasmid Induces Apoptosis in Non-Lung Cancer Cell Lines To demonstrate that the apoptotic effect of WIF-1 is not limited to NSCLC cells, we treated other cancer cells with serum-free conditioned medium from cells transfected with a WIF-1 expression plasmid (generated as described above). It was found that the apoptotic effect mediated by WIF-1 and observed in NSCLC cells is not limited to NSCCLC cells. Recombinant WIF-1 protein from serum-free conditional medium induced dose-dependent apoptosis in the melanoma cell line LOX (FIG. 13) and the melanoma cell line FEMX (FIG. 14). As observed for NSCLC cells, the WIF-1 domain (WD) also sufficient for inducing apoptosis in the melanoma cell line LOX (FIG. 15). In addition to inducing apoptosis, WIF-1 (WD) also inhibited the Wnt signaling pathway in the melanoma cell line LOX as evidenced, for example, by the reduced expression of dishevelled-3 (FIG. 16).

Example 11

Purified Human WIF-1 Induces Apoptosis in NSCLC Cell Lines

Figure 8C:
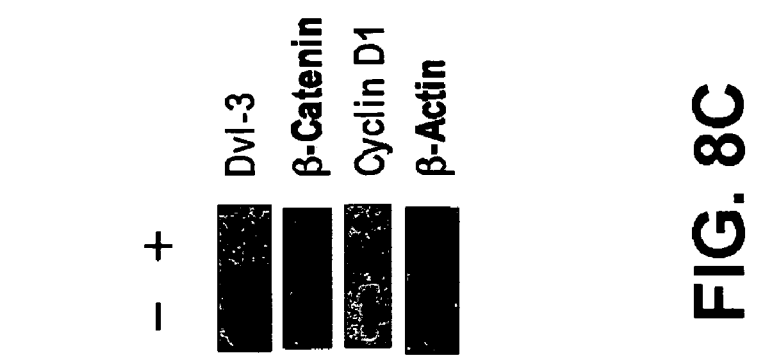
FIG. 8 shows that the purified human WIF-1 protein induces apoptosis in NSCLC cell lines. Panel A shows a flow cytometry analysis demonstrating that the WIF-1 protein causes cell death of H460 cells in a dose-dependent fashion. H460 cells were treated with WIF-1 protein for about 7 days. Bottom panel shows 0.5% Crystal Violet staining of H460 cells. Panel B shows that WIF-1 protein induces dose-dependent apoptosis induction in H460 cells. FL1-H represents Annexin V-FITC staining. Panel C shows a Western analysis with ("+") or without ("−") WIF-1 CM treatment of H460 cells for 72 hrs. Expression of Dvl-3, β-catenin, and Cyclin D1 was analyzed. β-Actin served as a loading control. Cytosolic proteins were prepared. Whole cell protein was used for cyclin D1 analysis.
Figure 8B:
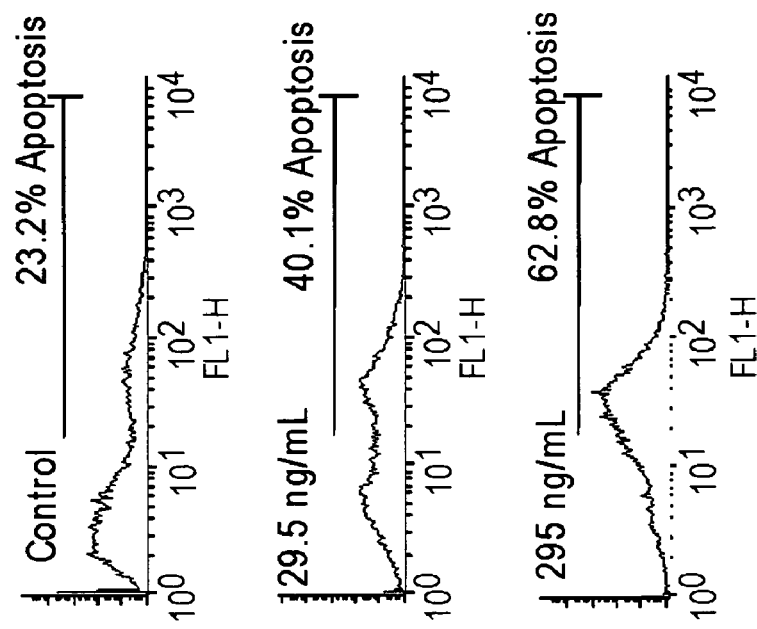
Figure 8A:
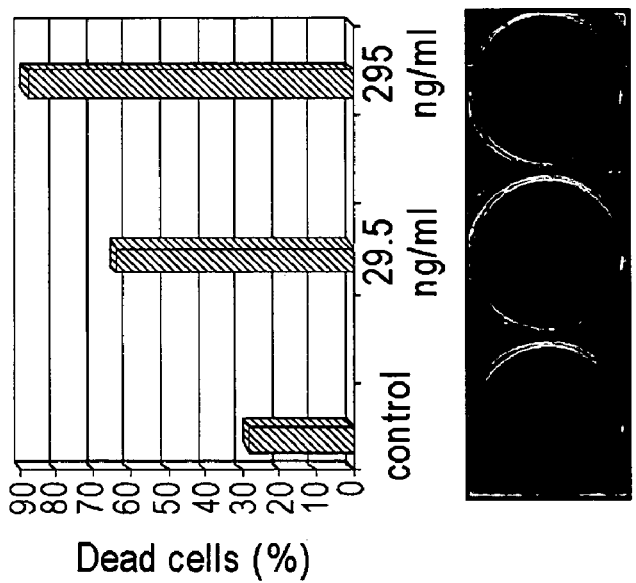
Figure 11:
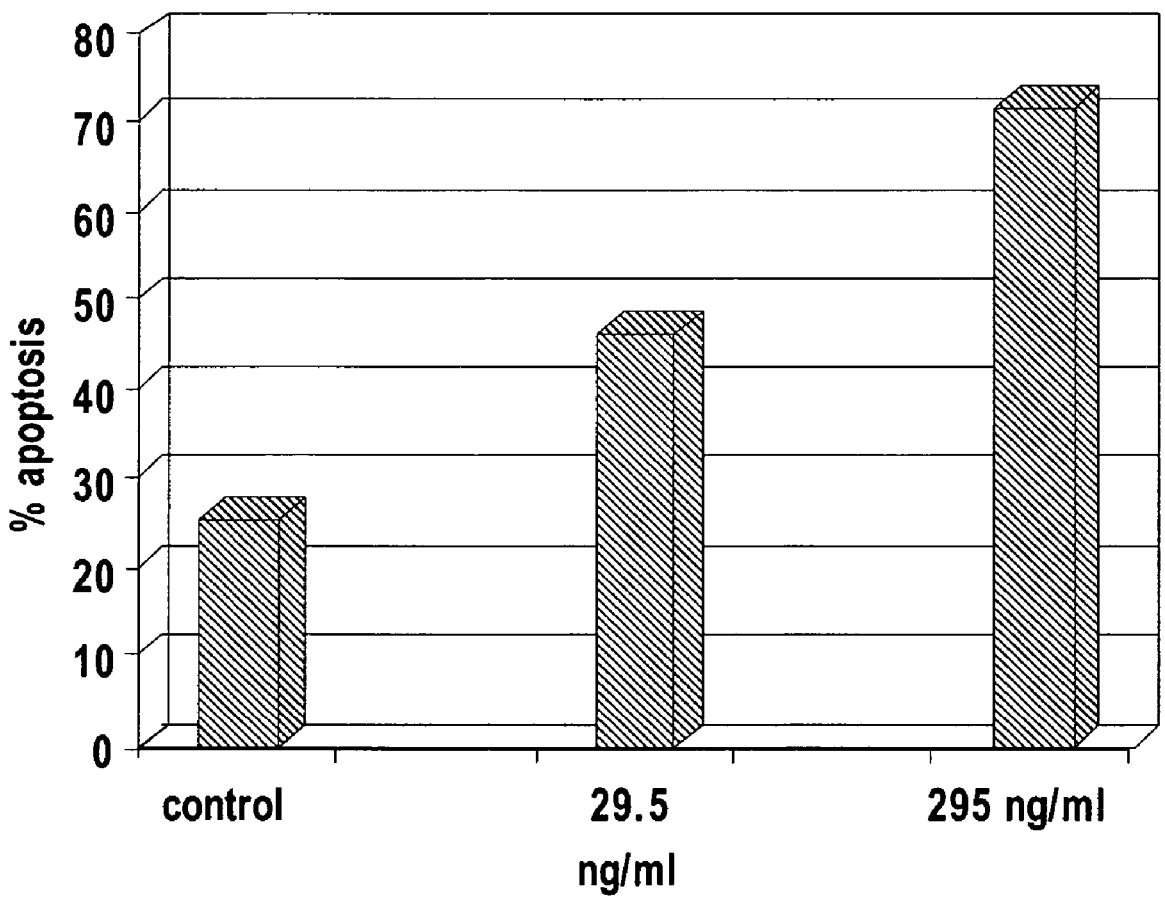
FIG. 11 shows that purified recombinant human WIF-1 protein (Abnova Corp.) induces dose-dependent apoptosis in the lung cancer cell line H460.

Purified recombinant human WIF-1 was used to validate the effect of WIF-1 in NSCLC cells. Purified rhWIF-1 protein was used to treat NSCLC cell line H460. After 7 days of incubation a cytopathic effect assay was used to determine the percentage of dead H460 cells. A dramatic cell death was observed (FIG. 8A). Cell killing was due largely to induction of apoptosis (40.1-62.8% of apoptotic cells after 7 days of incubation) (FIG. 8B). Previously, Uematsu et al. showed that Dvl-3 is over-expressed in NSCLC cells (Uematsu et al., *Oncogene* 22:7218-7221 (2003)). Further, He et al. and You et al. showed that the inhibition of the Wnt signaling pathway led to the down regulation of Dvl-3 and induced apoptosis in NSCLC cells (He et al., *Neoplasia* 6:7-14 (2004); You et al., *Oncogene* 23:6170-6174 (2004)). Here it is demonstrated that both cytosolic β-catenin and Dvl-3 were down-regulated after contacting the NSCLC cell line H460 with purified WIF-1 (FIG. 8C). One of the β-catenin-TCF key targeted genes, cyclinD1, was also found to be down-regulated after the addition of rhWIF-1 to H460 cells (FIG. 8C). Consistent with the WIF-1 CM data (see above and FIG. 7), the purified human WIF-1 induces apoptosis and inhibits Wnt signaling in NSCLC cells. Further, purified recombinant human WIF-1 protein induced dose-dependent apoptosis in the lung cancer cell line H460 (FIG. 11).

Example 12

Figure 18:
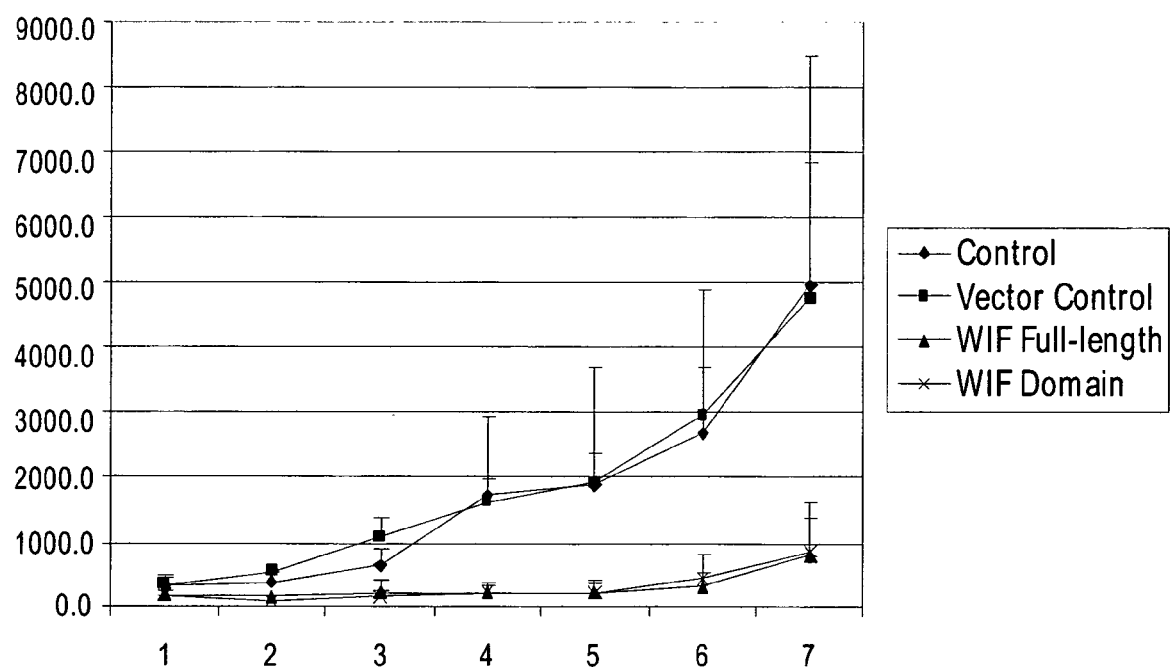
FIG. 18 shows that DNA encoding WIF-1 full-length (triangles) and DNA encoding WIF-1 domain (WD; asterisks) reduce tumor size in vivo. Control groups included non-vector control (diamonds) and vector control (squares). Tumor size was measured twice per week.

DNA Encoding WIF-1 Full-Length and DNA Encoding WIF-1 Domain (WD) Reduce Tumor Size In Vivo To demonstrate that WIF-1 can reduce tumor size in a mammal, in vivo testing with pcDNA3.1 WIF-1 full-length (amino acids 1-379; SEQ ID NO:2) and pcDNA3.1 WIF-1 domain (WD; amino acids 1-180; SEQ ID NO:16) was performed. $3 \times 10^6$ LOX cells were injected subcutaneously into athymic nude mice. Three days later (day 3), expression vectors were injected adjacent to tumors (5 mm). Injection of expression vectors was repeated on day 10. The following expression vectors and controls were used (FIG. 18): (i) Control, 501 µl of PBS; Vector Control, 200 µg of pcDNA3.1 in 50 µl lipofectamine; 200 µg of pcDNA3.1 WIF-1 full-length in 50 µl lipofectamine; and 200 µg of pcDNA3.1 WIF-1 Domain (WD) in 50 µl lipofectamine. Tumor size was measured with caliper twice per week and the volume was calculated using the equation $x^2y$ (where x<y). The difference of tumor volumes between WIF-1 treated animals (both for WIF-1 full-length and for WIF-1 domain (WD)) and control groups (i.e., non-vector and vector control) were statistically significant (P<0.01, Student t test). While tumors progressed in control animals, a significant reduction in tumor growth was observed in WIF-1 treated animals (FIG. 18). The tumor growth progressed similarly in non-vector and in vector control animals. Tumor growth suppression was also similar for WIF-1 full-length and for WIF-1 domain (WD).

Example 13

Recombinant WIF-1 Domain (WD) Protein Reduces Tumor Size In Vivo

Figure 19:
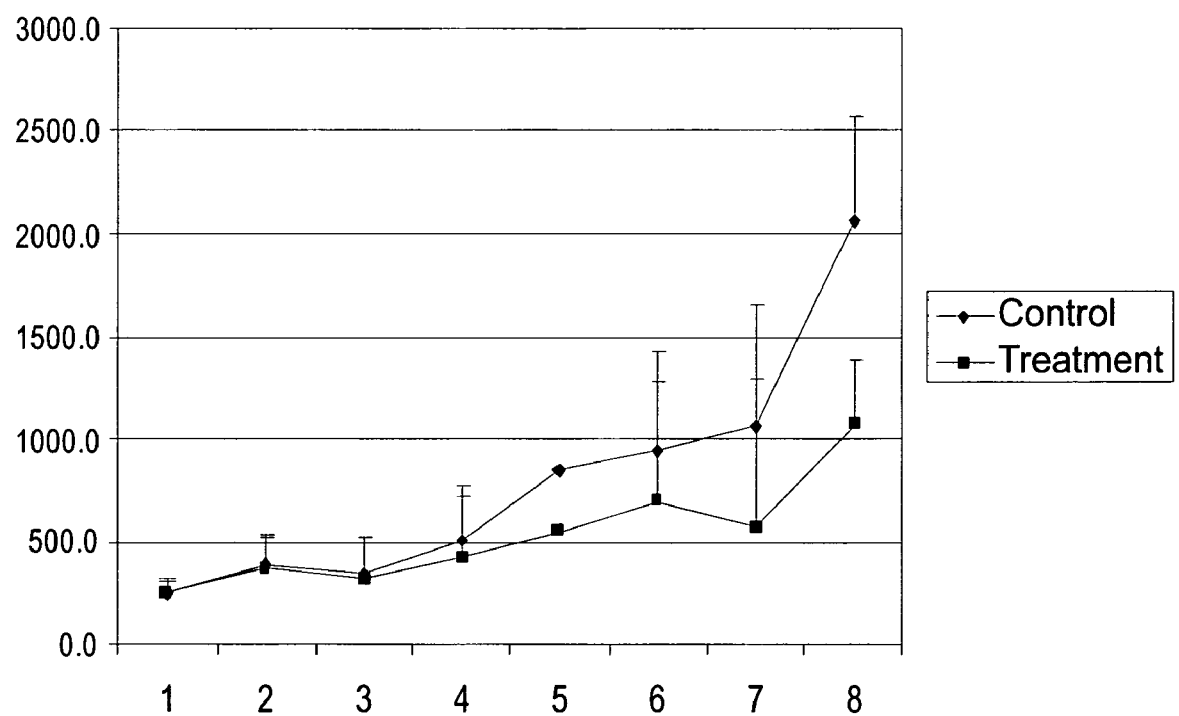
FIG. 19 shows that recombinant protein of WIF-1 domain (WD; squares) reduces tumor size in vivo. Control, diamonds. Tumor size was measured twice per week.

To demonstrate that WIF-1 domain protein (WD; amino acids 29-180 of SEQ ID NO: 16) can reduce tumor size in a mammal, in vivo testing was performed. $3 \times 10^6$ LOX cells were injected subcutaneously into athymic nude mice. Three days later (day 3), recombinant WIF-1 domain protein was injected on the tumor. Injections were repeated daily for 14 days. Recombinant WIF-1 domain protein was generated, as described herein, from 293 cells transfected with pcDNA3.1 WIF-1 domain (WD) expression vector comprising the sequence of SEQ ID NO: 18. Control animals were injected with supernatants from 293 cells transfected with pcDNA3.1 vector. Tumor size was measured with caliper twice per week and the last measurement was on day 18. Tumor volume was calculated using the equation $x^2y$ (where x<y). The difference of tumor volume between WIF-1 domain (WD) treated animals and control animals on day 18 was statistically significant (P<0.02, Student t test, n=3). While tumors progressed in control animals, a significant reduction in tumor growth was observed in WIF-1 domain (WD) protein treated animals (FIG. 19).

What is claimed is:

1. A method of inhibiting proliferation of a cancer cell, the method comprising;
   administering to a cancer cell exhibiting reduced WIF-1 expression an effective amount of a polypeptide comprising amino acids 39-176 of SEQ ID NO:2;
   wherein said administering inhibits cancer cell proliferation.

2. The method of claim 1, wherein the polypeptide is operably linked to a signal sequence.

3. The method of claim 1, wherein the polypeptide is fused to a heterologous amino acid sequence.

4. The method of claim 1, wherein the cancer cell is selected from the group consisting of lung cancer, breast cancer, colorectal cancer, melanoma, colon cancer, mesothelioma, ovarian cancer, gastric cancer, kidney cancer, bladder cancer, prostate cancer, uterine cancer, thyroid cancer, pancreatic cancer, cervical cancer, esophageal cancer, head and neck cancer, hepatocellular cancer, brain cancer, vulval cancer, testicular cancer, sarcoma, leukemia, lymphoma, glioma, and glioblastoma cell.

5. The method of claim 4, wherein the cancer cell is a lung cancer cell.

6. The method of claim 1, wherein the cancer cell is present in a mammal.

7. The method of claim 1, comprising administering an anti-cancer drug or therapeutic agent in addition to the polypeptide.

8. A method of inducing apoptosis in a cell, the method comprising;
   administering to a cell exhibiting reduced WIF-1 expression an effective amount of a polypeptide comprising amino acids 39-176 of SEQ ID NO:2;
   wherein said administering induces apoptosis in the cell.

9. The method of claim 8, wherein the polypeptide is operably linked to a signal sequence.

10. The method of claim 8, wherein the polypeptide is fused to a heterologous amino acid sequence.

11. The method of claim 8, wherein the cell is a cancer cell.

12. The method of claim 11, wherein the cancer cell is selected from the group consisting of lung cancer, breast cancer, colorectal cancer, melanoma, colon cancer, mesothelioma, ovarian cancer, gastric cancer, kidney cancer, bladder cancer, prostate cancer, uterine cancer, thyroid cancer, pancreatic cancer, cervical cancer, esophageal cancer, head and neck cancer, hepatocellular cancer, brain cancer, vulval cancer, testicular cancer, sarcoma, leukemia, lymphoma, glioma, and glioblastoma cell.

13. The method of claim 12, wherein the cancer cell is a lung cancer cell.

14. The method of claim 8, wherein the cell is present in a mammal.

15. The method of claim 8 further comprising an anti-cancer drug or therapeutic agent.

16. A method of inhibiting proliferation of a cancer cell that underexpresses a WIF-1 polypeptide, the method comprising:
    contacting the cancer cell with an amount of a polypeptide comprising a Wnt binding domain effective to inhibit proliferation of the cancer cell,
    wherein the polypeptide is a WIF-1 polypeptide comprising amino acids 39-176 of SEQ ID NO:2.

17. The method of claim 16, wherein the polypeptide is fused to an amino acid sequence that is heterologous to the polypeptide.

18. The method of claim 16, wherein said contacting is in vitro.

19. The method of claim 16, wherein said contacting is in vivo.

20. The method of claim 16, in which the cancer cell is selected from the group consisting of lung cancer, breast cancer, colorectal cancer, melanoma, colon cancer, mesothelioma, ovarian cancer, gastric cancer, kidney cancer, bladder cancer, prostate cancer, uterine cancer, thyroid cancer, pancreatic cancer, cervical cancer, esophageal cancer, head and neck cancer, hepatocellular cancer, brain cancer, vulval cancer, testicular cancer, sarcoma, leukemia, lymphoma, glioma, and glioblastoma cell.

21. The method of claim 20, wherein the cancer cell is a lung cancer cell.

22. The method of claim 16, wherein the cancer cell comprises a hypermethylated WIF-1 promoter.

23. The method of claim 16, comprising contacting the cancer cell with an expression vector encoding the polypeptide.

24. The method of claim 16, wherein the polypeptide comprises amino acids 29-176 of SEQ ID NO:2.

25. The method of claim 24, wherein the polypeptide comprises amino acids 1-176 of SEQ ID NO:2.

26. The method of claim 24, wherein the polypeptide comprises amino acids 29-180 of SEQ ID NO:2.

27. The method of claim 26, wherein the polypeptide comprises amino acids 1-180 of SEQ ID NO:2.

28. The method of claim 27, wherein the polypeptide comprises the amino acid sequence set forth in SEQ ID NO:2.

29. A method of inducing apoptosis of a cancer cell that underexpresses WIF-1, the method comprising:
    contacting the cancer cell with an amount of a polypeptide comprising a Wnt binding domain effective to induce apoptosis in the cancer cell,
    wherein the polypeptide is a WIF-1 polypeptide comprising amino acids 39-176 of SEQ ID NO:2.

30. The method of claim 29, wherein the polypeptide is fused to a heterologous an amino acid sequence.

31. The method of claim 29, wherein said contacting is in vitro.

32. The method of claim 29, wherein said contacting is in vivo.

33. The method of claim 29, in which the cancer cell is selected from the group consisting of lung cancer, breast cancer, colorectal cancer, melanoma, colon cancer, mesothelioma, ovarian cancer, gastric cancer, kidney cancer, bladder cancer, prostate cancer, uterine cancer, thyroid cancer, pancreatic cancer, cervical cancer, esophageal cancer, head and neck cancer, hepatocellular cancer, brain cancer, vulval cancer, testicular cancer, sarcoma, leukemia, lymphoma, glioma, and glioblastoma cell.

34. The method of claim 33, wherein the cancer cell is a lung cancer cell.

35. The method of claim 29, wherein the cancer cell comprises a hypermethylated WIF-1 promoter.

36. The method of claim 29 comprising contacting the cancer cell with an expression vector encoding the polypeptide.

37. The method of claim 29, wherein the polypeptide comprises amino acids 29-176 of SEQ ID NO:2.

38. The method of claim 37, wherein the polypeptide comprises amino acids 1-176 of SEQ ID NO:2.

39. The method of claim 37, wherein the polypeptide comprises amino acids 29-180 of SEQ ID NO:2.

40. The method of claim 39, wherein the polypeptide comprises amino acids 1-180 of SEQ ID NO:2.

41. The method of claim 40, wherein the polypeptide comprises the amino acid sequence set forth in SEQ ID NO:2.

* * * * *

UNITED STATES PATENT AND TRADEMARK OFFICE
CERTIFICATE OF CORRECTION

| | | |
|---|---|---|
| PATENT NO. | : 7,618,936 B2 | Page 1 of 1 |
| APPLICATION NO. | : 11/136619 | |
| DATED | : November 17, 2009 | |
| INVENTOR(S) | : Liang You | |

It is certified that error appears in the above-identified patent and that said Letters Patent is hereby corrected as shown below:

In Claim 15 (Originally Claim 70), Section 91, line 15, after the word "comprising" insert the word --administering--.

In Claim 30 (Originally Claim 81), Section 92, line 17, after the word "heterologous" delete the word "an".

Signed and Sealed this

Sixteenth Day of February, 2010

David J. Kappos
*Director of the United States Patent and Trademark Office*

SEQUENCE LISTING

```
<160> NUMBER OF SEQ ID NOS: 30

<210> SEQ ID NO 1
<211> LENGTH: 2020
<212> TYPE: DNA
<213> ORGANISM: Homo sapiens

<400> SEQUENCE: 1
gtctaaacgg gaacagccct ggctgaggga gctgcagcgc agcagagtat ctgacggcgc      60
caggttgcgt aggtgcggca cgaggagttt tcccggcagc gaggaggtcc tgagcagcat     120
ggcccggagg agcgccttcc ctgccgccgc gctctggctc tggagcatcc tcctgtgcct     180
gctggcactg cgggcggagg ccgggccgcc gcaggaggag agcctgtacc tatggatcga     240
```

| | |
|---|---|
| tgctcaccag gcaagagtac tcataggatt tgaagaagat atcctgattg tttcagaggg | 300 |
| gaaaatggca cctttacac atgatttcag aaaagcgcaa cagagaatgc cagctattcc | 360 |
| tgtcaatatc cattccatga attttacctg gcaagctgca gggcaggcag aatacttcta | 420 |
| tgaattcctg tccttgcgct ccctggataa aggcatcatg gcagatccaa ccgtcaatgt | 480 |
| ccctctgctg ggaacagtgc ctcacaaggc atcagttgtt caagttggtt cccatgtct | 540 |
| tggaaaacag gatggggtgg cagcatttga agtggatgtg attgttatga attctgaagg | 600 |
| caacaccatt ctccaaacac ctcaaaatgc tatcttcttt aaaacatgtc tacaagctga | 660 |
| gtgcccaggc gggtgccgaa atggaggctt ttgtaatgaa agacgcatct gcgagtgtcc | 720 |
| tgatgggttc cacggacctc actgtgagaa agccctttgt accccacgat gtatgaatgg | 780 |
| tggactttgt gtgactcctg gtttctgcat ctgcccacct ggattctatg gagtgaactg | 840 |
| tgacaaagca aactgctcaa ccacctgctt taatggaggg acctgtttct accctggaaa | 900 |
| atgtatttgc cctccaggac tagggggaga gcagtgtgaa atcagcaaat gcccacaacc | 960 |
| ctgtcgaaat ggaggtaaat gcattggtaa aagcaaatgt aagtgttcca aaggttacca | 1020 |
| gggagacctc tgttcaaagc ctgtctgcga gcctggctgt ggtgcacatg gaacctgcca | 1080 |
| tgaacccaac aaatgccaat gtcaagaagg ttggcatgga agacactgca ataaaggta | 1140 |
| cgaagccagc ctcatacatg ccctgaggcc agcaggcgcc cagctcaggc agcacacgcc | 1200 |
| ttcacttaaa aaggccgagg agcggcggga tccacctgaa tccaattaca tctggtgaac | 1260 |
| tccgacatct gaaacgtttt aagttacacc aagttcatag cctttgttaa cctttcatgt | 1320 |
| gttgaatgtt caaataatgt tcattacact taagaatact ggcctgaatt ttattagctt | 1380 |
| cattataaat cactgagctg atatttactc ttccttttaa gttttctaag tacgtctgta | 1440 |
| gcatgatggt atagatttc ttgtttcagt gctttgggac agattttata ttatgtcaat | 1500 |
| tgatcaggtt aaaattttca gtgtgtagtt ggcagatatt ttcaaaatta caatgcattt | 1560 |
| atggtgtctg ggggcagggg aacatcagaa aggttaaatt gggcaaaaat gcgtaagtca | 1620 |
| caagaatttg gatggtgcag ttaatgttga agttacagca tttcagattt tattgtcaga | 1680 |
| tatttagatg tttgttacat ttttaaaaat tgctcttaat ttttaaactc tcaatacaat | 1740 |
| atattttgac cttaccatta ttccagagat tcagtattaa aaaaaaaaaa aattacactg | 1800 |
| tggtagtggc atttaaacaa tataatatat tctaaacaca atgaaatagg gaatataatg | 1860 |
| tatgaacttt ttgcattggc ttgaagcaat ataatatatt gtaaacaaaa cacagctctt | 1920 |
| acctaataaa cattttatac tgtttgtatg tataaaataa aggtgctgct ttagttttca | 1980 |
| aaaaaaaaa aaaaaaaaa aaaaaaaaa aaaaaaaaa | 2020 |

<210> SEQ ID NO 2
<211> LENGTH: 379
<212> TYPE: PRT
<213> ORGANISM: Homo sapiens

<400> SEQUENCE: 2

Met Ala Arg Arg Ser Ala Phe Pro Ala Ala Leu Trp Leu Trp Ser
1               5                   10                  15

Ile Leu Leu Cys Leu Leu Ala Leu Arg Ala Glu Ala Gly Pro Pro Gln
            20                  25                  30

Glu Glu Ser Leu Tyr Leu Trp Ile Asp Ala His Gln Ala Arg Val Leu
        35                  40                  45

Ile Gly Phe Glu Glu Asp Ile Leu Ile Val Ser Glu Gly Lys Met Ala
    50                  55                  60

Pro Phe Thr His Asp Phe Arg Lys Ala Gln Gln Arg Met Pro Ala Ile
65                  70                  75                  80

Pro Val Asn Ile His Ser Met Asn Phe Thr Trp Gln Ala Ala Gly Gln
                85                  90                  95

Ala Glu Tyr Phe Tyr Glu Phe Leu Ser Leu Arg Ser Leu Asp Lys Gly
            100                 105                 110

Ile Met Ala Asp Pro Thr Val Asn Val Pro Leu Leu Gly Thr Val Pro
        115                 120                 125

His Lys Ala Ser Val Val Gln Val Gly Phe Pro Cys Leu Gly Lys Gln
    130                 135                 140

Asp Gly Val Ala Ala Phe Glu Val Asp Val Ile Val Met Asn Ser Glu
145                 150                 155                 160

Gly Asn Thr Ile Leu Gln Thr Pro Gln Asn Ala Ile Phe Phe Lys Thr
                165                 170                 175

Cys Leu Gln Ala Glu Cys Pro Gly Gly Cys Arg Asn Gly Gly Phe Cys
            180                 185                 190

Asn Glu Arg Arg Ile Cys Glu Cys Pro Asp Gly Phe His Gly Pro His
        195                 200                 205

Cys Glu Lys Ala Leu Cys Thr Pro Arg Cys Met Asn Gly Gly Leu Cys
    210                 215                 220

Val Thr Pro Gly Phe Cys Ile Cys Pro Pro Gly Phe Tyr Gly Val Asn
225                 230                 235                 240

Cys Asp Lys Ala Asn Cys Ser Thr Thr Cys Phe Asn Gly Gly Thr Cys
                245                 250                 255

Phe Tyr Pro Gly Lys Cys Ile Cys Pro Pro Gly Leu Glu Gly Glu Gln
            260                 265                 270

Cys Glu Ile Ser Lys Cys Pro Gln Pro Cys Arg Asn Gly Gly Lys Cys
        275                 280                 285

Ile Gly Lys Ser Lys Cys Lys Cys Ser Lys Gly Tyr Gln Gly Asp Leu
    290                 295                 300

Cys Ser Lys Pro Val Cys Glu Pro Gly Cys Gly Ala His Gly Thr Cys
305                 310                 315                 320

His Glu Pro Asn Lys Cys Gln Cys Gln Glu Gly Trp His Gly Arg His
                325                 330                 335

Cys Asn Lys Arg Tyr Glu Ala Ser Leu Ile His Ala Leu Arg Pro Ala
            340                 345                 350

Gly Ala Gln Leu Arg Gln His Thr Pro Ser Leu Lys Lys Ala Glu Glu
        355                 360                 365

Arg Arg Asp Pro Pro Glu Ser Asn Tyr Ile Trp
370                 375

<210> SEQ ID NO 3
<211> LENGTH: 1662
<212> TYPE: DNA
<213> ORGANISM: Homo sapiens

<400> SEQUENCE: 3
aattcggcaa cttttaaaaa attattttat ttatttattt atatattttt tgagacggag      60
tctcgctcta tcgcccaggc tggagtgcag tgccacgatc ttggcttaat gcaacctccg     120
cctcccggtt caagtgattc tcctgcctca gcctcccggg tagctaggac tacaggcccc     180
cgccaccatg cccagctaat ttttgcattt ttagtagaga cggggtttca ccacgctggc     240
caagctggtc tcgaactcct gacctcaggt gatccgcccg ccttggcctc ccaaagtgca     300

-continued

```
gggattacag gcgtgagcca tcgcgcccgg ccgaattcag caacttttaa aaaatatcag    360
caaacgtgaa gatatccacg atgttagagg agccctaccc cggagggtca ggtacagcta    420
tcgtccaggg cccagggcac tcttccgggc actgccgggt tatcagggag acagacggga    480
atccccaaat gctgggtgtc gggcaagtac cagctggacg ccctgcgcct cgagccaagg    540
ccagcgcctg ccatcggcac catcggacag tcgagcctcg agttttaact gcttgggagc    600
gcgcaaagtg ccagcctatc gcagaacgga gcgcataggt tggcggaga gaggaatcct    660 actggctgaa agggagacga agggcaattt gcgccttcag tgagcgccgg aggaggaaca    720
ggagtcatca cctcatcatc atcatcatca tcatcatcac catcaccatc accatcatca    780
gcactcagtc aagcccagcg ttgtctgctc tccccatttc cctcccccga agcctcccctt    840 ggcccgagga ggtggcgagt gatgtcccag gggtctctga gtgcccttct ccgggtccgc    900
cagccctaca cgcccacttc gcgggcgctc cactgggcgc accgcactgt gaatgcagcc    960 tcggggtcc ctcgcggccc cgccccggg ggggccccac agcgcccca agtggcggcc    1020 gcccaggcct cgcgggcccc actcctcgct cgcacctcgc tcgcgccagc ccttcccgct    1080
cttctgttct cgctctattt gccccgctga ctgctggcct cgccagcttt gccagtctta    1140
cgtctctgcc gcccccactc ccgcccgcgc ccatcttct tgcgcgactc gcgcccgctg    1200
gtccccccct cctcctcccg cgtcctgcct gccccctcct cctgctctcg caggctcctt    1260
ggcacccagg ccgggaggcg acgcgcccag ccgtctaaac gggaacagcc ctggctgagg    1320
gagctgcagc gcagcagagt atctgacggc gccaggttgc gtaggtgcgg cacgaggagt    1380
tttcccggca gcgaggaggt cctgagcagc atggcccgga ggagcgcctt ccctgccgcc    1440
gcgctctggc tctggagcat cctcctgtgc ctgctggcac tgcgggcgga ggccgggccg    1500
ccgcaggagg agagcctgta cctatggatc gatgctcacc aggcaagagt actcatagga    1560
tttgaagaag atatcctgat tgtttcagag gggaaaatgg cacctttac acatgatttc    1620 agaaaagcgc aacagagaat gccagctatt cctgtcaata tc                      1662
```

<210> SEQ ID NO 4
<211> LENGTH: 20
<212> TYPE: DNA
<213> ORGANISM: Artificial
<220> FEATURE:
<223> OTHER INFORMATION: Methylation-specific primer

<400> SEQUENCE: 4
gggcgtttta ttgggcgtat                                                 20

<210> SEQ ID NO 5
<211> LENGTH: 19
<212> TYPE: DNA
<213> ORGANISM: Artificial
<220> FEATURE:
<223> OTHER INFORMATION: Methylation-specific primer

<400> SEQUENCE: 5
aaaccaacaa tcaacgaac                                                  19

<210> SEQ ID NO 6
<211> LENGTH: 20
<212> TYPE: DNA
<213> ORGANISM: Artificial
<220> FEATURE:
<223> OTHER INFORMATION: Unmethylation-specific primer

<400> SEQUENCE: 6

```
gggtgtttta ttgggtgtat                                                20
```

<210> SEQ ID NO 7
<211> LENGTH: 20
<212> TYPE: DNA
<213> ORGANISM: Artificial
<220> FEATURE:
<223> OTHER INFORMATION: Unmethylation-specific primer

<400> SEQUENCE: 7

```
aaaccaacaa tcaacaaaac                                                20
```

<210> SEQ ID NO 8
<211> LENGTH: 20
<212> TYPE: DNA
<213> ORGANISM: Artificial
<220> FEATURE:
<223> OTHER INFORMATION: PCR primer to amplify promotor region

<400> SEQUENCE: 8

```
gagtgatgtt ttaggggttt                                                20
```

<210> SEQ ID NO 9
<211> LENGTH: 21
<212> TYPE: DNA
<213> ORGANISM: Artificial
<220> FEATURE:
<223> OTHER INFORMATION: PCR primer to amplify promotor region

<400> SEQUENCE: 9

```
cctaaatacc aaaaaaccta c                                              21
```

<210> SEQ ID NO 10
<211> LENGTH: 21
<212> TYPE: DNA
<213> ORGANISM: Artificial
<220> FEATURE:
<223> OTHER INFORMATION: PCR primer to amplify promotor region

<400> SEQUENCE: 10

```
gtaggttttt tggtatttag g                                              21
```

<210> SEQ ID NO 11
<211> LENGTH: 22
<212> TYPE: DNA
<213> ORGANISM: Artificial
<220> FEATURE:
<223> OTHER INFORMATION: PCR primer to amplify promotor region

<400> SEQUENCE: 11

```
tccataaata caaactctcc tc                                             22
```

<210> SEQ ID NO 12
<211> LENGTH: 20
<212> TYPE: DNA
<213> ORGANISM: Artificial
<220> FEATURE:
<223> OTHER INFORMATION: Human WIF-1 Primer

<400> SEQUENCE: 12

```
ccgaaatgga ggcttttgta                                                20
```

<210> SEQ ID NO 13
<211> LENGTH: 20
<212> TYPE: DNA

<213> ORGANISM: Artificial
<220> FEATURE:
<223> OTHER INFORMATION: Human WIF-1 Primer

<400> SEQUENCE: 13
tggttgagca gtttgctttg                                          20

<210> SEQ ID NO 14
<211> LENGTH: 351
<212> TYPE: PRT
<213> ORGANISM: Homo sapiens

<400> SEQUENCE: 14

Gly Pro Pro Gln Glu Glu Ser Leu Tyr Leu Trp Ile Asp Ala His Gln
1               5                   10                  15

Ala Arg Val Leu Ile Gly Phe Glu Glu Asp Ile Leu Ile Val Ser Glu
            20                  25                  30

Gly Lys Met Ala Pro Phe Thr His Asp Phe Arg Lys Ala Gln Gln Arg
        35                  40                  45

Met Pro Ala Ile Pro Val Asn Ile His Ser Met Asn Phe Thr Trp Gln
    50                  55                  60

Ala Ala Gly Gln Ala Glu Tyr Phe Tyr Glu Phe Leu Ser Leu Arg Ser
65                  70                  75                  80

Leu Asp Lys Gly Ile Met Ala Asp Pro Thr Val Asn Val Pro Leu Leu
                85                  90                  95

Gly Thr Val Pro His Lys Ala Ser Val Val Gln Val Gly Phe Pro Cys
            100                 105                 110

Leu Gly Lys Gln Asp Gly Val Ala Ala Phe Glu Val Asp Val Ile Val
        115                 120                 125

Met Asn Ser Glu Gly Asn Thr Ile Leu Lys Thr Pro Gln Asn Ala Ile
    130                 135                 140

Phe Phe Lys Thr Cys Gln Gln Ala Glu Cys Pro Gly Gly Cys Arg Asn
145                 150                 155                 160

Gly Gly Phe Cys Asn Glu Arg Arg Ile Cys Glu Cys Pro Asp Gly Phe
                165                 170                 175

His Gly Pro His Cys Glu Lys Ala Leu Cys Thr Pro Arg Cys Met Asn
            180                 185                 190

Gly Gly Leu Cys Val Thr Pro Gly Phe Cys Ile Cys Pro Pro Gly Phe
        195                 200                 205

Tyr Gly Val Asn Cys Asp Lys Ala Asn Cys Ser Thr Thr Cys Phe Asn
    210                 215                 220

Gly Gly Thr Cys Phe Tyr Pro Gly Lys Cys Ile Cys Pro Pro Gly Leu
225                 230                 235                 240

Glu Gly Glu Gln Cys Glu Ile Ser Lys Cys Pro Gln Pro Cys Arg Asn
                245                 250                 255

Gly Gly Lys Cys Ile Gly Lys Ser Lys Cys Lys Cys Ser Lys Gly Tyr
            260                 265                 270

Gln Gly Asp Leu Cys Ser Lys Pro Val Cys Glu Pro Gly Cys Gly Ala
        275                 280                 285

His Gly Thr Cys His Glu Pro Asn Lys Cys Gln Cys Gln Glu Gly Trp
    290                 295                 300

His Gly Arg His Cys Asn Lys Arg Tyr Glu Ala Ser Leu Ile His Ala
305                 310                 315                 320

Leu Arg Pro Ala Gly Ala Gln Leu Arg Gln His Thr Pro Ser Leu Lys
                325                 330                 335

Lys Ala Glu Glu Arg Arg Asp Pro Pro Glu Ser Asn Tyr Ile Trp
                340                 345                 350

<210> SEQ ID NO 15
<211> LENGTH: 139
<212> TYPE: PRT
<213> ORGANISM: Homo sapiens

<400> SEQUENCE: 15

Trp Ile Asp Ala His Gln Ala Arg Val Leu Ile Gly Phe Glu Glu Asp
1               5                   10                  15

Ile Leu Ile Val Ser Glu Gly Lys Met Ala Pro Phe Thr His Asp Phe
            20                  25                  30

Arg Lys Ala Gln Gln Arg Met Pro Ala Ile Pro Val Asn Ile His Ser
        35                  40                  45

Met Asn Phe Thr Trp Gln Ala Ala Gly Gln Ala Glu Tyr Phe Tyr Glu
    50                  55                  60

Phe Leu Ser Leu Arg Ser Leu Asp Lys Gly Ile Met Ala Asp Pro Thr
65                  70                  75                  80

Val Asn Val Pro Leu Leu Gly Thr Val Pro His Lys Ala Ser Val Val
                85                  90                  95

Gln Val Gly Phe Pro Cys Leu Gly Lys Gln Asp Gly Val Ala Ala Phe
            100                 105                 110

Glu Val Asp Val Ile Val Met Asn Ser Glu Gly Asn Thr Ile Leu Lys
        115                 120                 125

Thr Pro Gln Asn Ala Ile Phe Phe Lys Thr Cys
    130                 135

<210> SEQ ID NO 16
<211> LENGTH: 180
<212> TYPE: PRT
<213> ORGANISM: Homo sapiens

<400> SEQUENCE: 16

Met Ala Arg Arg Ser Ala Phe Pro Ala Ala Ala Leu Trp Leu Trp Ser
1               5                   10                  15

Ile Leu Leu Cys Leu Leu Ala Leu Arg Ala Glu Ala Gly Pro Pro Gln
            20                  25                  30

Glu Glu Ser Leu Tyr Leu Trp Ile Asp Ala His Gln Ala Arg Val Leu
        35                  40                  45

Ile Gly Phe Glu Glu Asp Ile Leu Ile Val Ser Glu Gly Lys Met Ala
    50                  55                  60

Pro Phe Thr His Asp Phe Arg Lys Ala Gln Gln Arg Met Pro Ala Ile
65                  70                  75                  80

Pro Val Asn Ile His Ser Met Asn Phe Thr Trp Gln Ala Ala Gly Gln
                85                  90                  95

Ala Glu Tyr Phe Tyr Glu Phe Leu Ser Leu Arg Ser Leu Asp Lys Gly
            100                 105                 110

Ile Met Ala Asp Pro Thr Val Asn Val Pro Leu Leu Gly Thr Val Pro
        115                 120                 125

His Lys Ala Ser Val Val Gln Val Gly Phe Pro Cys Leu Gly Lys Gln
    130                 135                 140

Asp Gly Val Ala Ala Phe Glu Val Asp Val Ile Val Met Asn Ser Glu
145                 150                 155                 160

Gly Asn Thr Ile Leu Lys Thr Pro Gln Asn Ala Ile Phe Phe Lys Thr
                165                 170                 175

Cys Gln Gln Ala
        180

<210> SEQ ID NO 17
<211> LENGTH: 1140
<212> TYPE: DNA
<213> ORGANISM: Homo sapiens

<400> SEQUENCE: 17

| | | | | | | |
|---|---|---|---|---|---|---|
| atggcccgga | ggagcgcctt | ccctgccgcc | gcgctctggc | tctggagcat | cctcctgtgc | 60 |
| ctgctggcac | tgcgggcgga | ggccgggccg | ccgcaggagg | agagcctgta | cctatggatc | 120 |
| gatgctcacc | aggcaagagt | actcatagga | tttgaagaag | atatcctgat | tgtttcagag | 180 |
| gggaaaatgg | cacctttttac | acatgatttc | agaaaagcgc | aacagagaat | gccagctatt | 240 |
| cctgtcaata | tccattccat | gaattttacc | tggcaagctg | cagggcaggc | agaatacttc | 300 |
| tatgaattcc | tgtccttgcg | ctccctggat | aaaggcatca | tggcagatcc | aaccgtcaat | 360 |
| gtccctctgc | tgggaacagt | gcctcacaag | gcatcagttg | ttcaagttgg | tttcccatgt | 420 |
| cttgaaaaac | aggatggggt | ggcagcattt | gaagtggatg | tgattgttat | gaattctgaa | 480 |
| ggcaacacca | ttctccaaac | acctcaaaat | gctatcttct | ttaaaacatg | tctacaagct | 540 |
| gagtgcccag | gcgggtgccg | aaatggaggc | ttttgtaatg | aaagacgcat | ctgcgagtgt | 600 |
| cctgatgggt | tccacggacc | tcactgtgag | aaagcccttt | gtaccccacg | atgtatgaat | 660 |
| ggtggacttt | gtgtgactcc | tggtttctgc | atctgcccac | tggattcta | tggagtgaac | 720 |
| tgtgacaaag | caaactgctc | aaccacctgc | tttaatggag | ggacctgttt | ctaccctgga | 780 |
| aaatgtattt | gccctccagg | actagaggga | gagcagtgtg | aaatcagcaa | atgcccacaa | 840 |
| ccctgtcgaa | atggaggtaa | atgcattggt | aaaagcaaat | gtaagtgttc | caaaggttac | 900 |
| cagggagacc | tctgttcaaa | gcctgtctgc | gagcctggct | gtggtgcaca | tggaacctgc | 960 |
| catgaaccca | caaatgcca | atgtcaagaa | ggttggcatg | gaagacactg | caataaaagg | 1020 |
| tacgaagcca | gcctcataca | tgccctgagg | ccagcaggcg | cccagctcag | gcagcacacg | 1080 |
| ccttcactta | aaaaggccga | ggagcggcgg | gatccacctg | aatccaatta | catctggtga | 1140 |

<210> SEQ ID NO 18
<211> LENGTH: 540
<212> TYPE: DNA
<213> ORGANISM: Homo sapiens

<400> SEQUENCE: 18

| | | | | | | |
|---|---|---|---|---|---|---|
| atggcccgga | ggagcgcctt | ccctgccgcc | gcgctctggc | tctggagcat | cctcctgtgc | 60 |
| ctgctggcac | tgcgggcgga | ggccgggccg | ccgcaggagg | agagcctgta | cctatggatc | 120 |
| gatgctcacc | aggcaagagt | actcatagga | tttgaagaag | atatcctgat | tgtttcagag | 180 |
| gggaaaatgg | cacctttttac | acatgatttc | agaaaagcgc | aacagagaat | gccagctatt | 240 |
| cctgtcaata | tccattccat | gaattttacc | tggcaagctg | cagggcaggc | agaatacttc | 300 |
| tatgaattcc | tgtccttgcg | ctccctggat | aaaggcatca | tggcagatcc | aaccgtcaat | 360 |
| gtccctctgc | tgggaacagt | gcctcacaag | gcatcagttg | ttcaagttgg | tttcccatgt | 420 |
| cttgaaaaac | aggatggggt | ggcagcattt | gaagtggatg | tgattgttat | gaattctgaa | 480 |
| ggcaacacca | ttctccaaac | acctcaaaat | gctatcttct | ttaaaacatg | tctacaagct | 540 |

<210> SEQ ID NO 19
<211> LENGTH: 417
<212> TYPE: DNA

<213> ORGANISM: Homo sapiens

<400> SEQUENCE: 19

```
tggatcgatg ctcaccaggc aagagtactc ataggatttg aagaagatat cctgattgtt    60
tcagagggga aaatggcacc ttttacacat gatttcagaa aagcgcaaca gagaatgcca   120
gctattcctg tcaatatcca ttccatgaat tttacctggc aagctgcagg gcaggcagaa   180
tacttctatg aattcctgtc cttgcgctcc ctggataaag gcatcatggc agatccaacc   240
gtcaatgtcc ctctgctggg aacagtgcct cacaaggcat cagttgttca agttggtttc   300
ccatgtcttg gaaacagga tggggtggca gcatttgaag tggatgtgat tgttatgaat   360
tctgaaggca acaccattct ccaaacacct caaaatgcta tcttctttaa aacatgt     417
```

<210> SEQ ID NO 20
<211> LENGTH: 28
<212> TYPE: PRT
<213> ORGANISM: Homo sapiens

<400> SEQUENCE: 20

Met Ala Arg Arg Ser Ala Phe Pro Ala Ala Ala Leu Trp Leu Trp Ser
1               5                   10                  15

Ile Leu Leu Cys Leu Leu Ala Leu Arg Ala Glu Ala
            20                  25

<210> SEQ ID NO 21
<211> LENGTH: 414
<212> TYPE: DNA
<213> ORGANISM: Homo sapiens

<400> SEQUENCE: 21

```
tggatcgatg ctcaccaggc aagagtactc ataggatttg aagaagatat cctgattgtt    60
tcagagggga aaatggcacc ttttacacat gatttcagaa aagcgcaaca gagaatgcca   120
gctattcctg tcaatatcca ttccatgaat tttacctggc aagctgcagg gcaggcagaa   180
tacttctatg aattcctgtc cttgcgctcc ctggataaag gcatcatggc agatccaacc   240
gtcaatgtcc ctctgctggg aacagtgcct cacaaggcat cagttgttca agttggtttc   300
ccatgtcttg gaaacagga tggggtggca gcatttgaag tggatgtgat tgttatgaat   360
tctgaaggca acaccattct ccaaacacct caaaatgcta tcttctttaa aaca        414
```

<210> SEQ ID NO 22
<211> LENGTH: 379
<212> TYPE: PRT
<213> ORGANISM: Mus musculus

<400> SEQUENCE: 22

Met Ala Arg Arg Arg Ala Phe Pro Ala Phe Ala Leu Arg Leu Trp Ser
1               5                   10                  15

Ile Leu Pro Cys Leu Leu Leu Arg Ala Asp Ala Gly Gln Pro Pro
            20                  25                  30

Glu Glu Ser Leu Tyr Leu Trp Ile Asp Ala His Gln Ala Arg Val Leu
35                  40                  45

Ile Gly Phe Glu Glu Asp Ile Leu Ile Val Ser Glu Gly Lys Met Ala
50                  55                  60

Pro Phe Thr His Asp Phe Arg Lys Ala Gln Gln Arg Met Pro Ala Ile
65                  70                  75                  80

Pro Val Asn Ile His Ser Met Asn Phe Thr Trp Gln Ala Ala Gly Gln
                85                  90                  95

Ala Glu Tyr Phe Tyr Glu Phe Leu Ser Leu Arg Ser Leu Asp Lys Gly
            100                 105                 110

Ile Met Ala Asp Pro Thr Val Asn Val Pro Leu Leu Gly Thr Val Pro
            115                 120                 125

His Lys Ala Ser Val Val Gln Val Gly Phe Pro Cys Leu Gly Lys Gln
            130                 135                 140

Asp Gly Val Ala Ala Phe Glu Val Asn Val Ile Val Met Asn Ser Glu
145                 150                 155                 160

Gly Asn Thr Ile Leu Arg Thr Pro Gln Asn Ala Ile Phe Phe Lys Thr
            165                 170                 175

Cys Gln Gln Ala Glu Cys Pro Gly Gly Cys Arg Asn Gly Gly Phe Cys
            180                 185                 190

Asn Glu Arg Arg Val Cys Glu Cys Pro Asp Gly Phe Tyr Gly Pro His
            195                 200                 205

Cys Glu Lys Ala Leu Cys Ile Pro Arg Cys Met Asn Gly Gly Leu Cys
            210                 215                 220

Val Thr Pro Gly Phe Cys Ile Cys Pro Pro Gly Phe Tyr Gly Val Asn
225                 230                 235                 240

Cys Asp Lys Ala Asn Cys Ser Thr Thr Cys Phe Asn Gly Gly Thr Cys
            245                 250                 255

Phe Tyr Pro Gly Lys Cys Ile Cys Pro Pro Gly Leu Glu Gly Glu Gln
            260                 265                 270

Cys Glu Leu Ser Lys Cys Pro Gln Pro Cys Arg Asn Gly Gly Lys Cys
            275                 280                 285

Ile Gly Lys Ser Lys Cys Lys Cys Pro Lys Gly Tyr Gln Gly Asp Leu
            290                 295                 300

Cys Ser Lys Pro Val Cys Glu Pro Gly Cys Gly Ala His Gly Thr Cys
305                 310                 315                 320

His Glu Pro Asn Lys Cys Gln Cys Arg Glu Gly Trp His Gly Arg His
            325                 330                 335

Cys Asn Lys Arg Tyr Gly Ala Ser Leu Met His Ala Pro Arg Pro Ala
            340                 345                 350

Gly Ala Gly Leu Glu Arg His Thr Pro Ser Leu Lys Lys Ala Glu Asp
            355                 360                 365

Arg Arg Asp Pro Pro Glu Ser Asn Tyr Ile Trp
            370                 375

<210> SEQ ID NO 23
<211> LENGTH: 379
<212> TYPE: PRT
<213> ORGANISM: Rattus rattus

<400> SEQUENCE: 23

Met Ala Arg Arg Arg Ala Phe Pro Ala Phe Val Leu Arg Leu Trp Ser
1               5                   10                  15

Ile Leu Pro Cys Leu Leu Leu Arg Ala Asp Ala Gly Gln Pro Pro
            20                  25                  30

Glu Glu Ser Leu Tyr Leu Trp Ile Asp Ala His Gln Ala Arg Val Leu
            35                  40                  45

Ile Gly Phe Glu Glu Asp Ile Leu Ile Val Ser Glu Gly Lys Met Ala
            50                  55                  60

Pro Phe Thr His Asp Phe Arg Lys Ala Gln Gln Arg Met Pro Ala Ile
65                  70                  75                  80

Pro Val Asn Ile His Ser Met Asn Phe Thr Trp Gln Ala Ser Gly Gln

```
                85                  90                  95
Ala Glu Tyr Phe Tyr Glu Phe Leu Ser Leu Arg Ser Leu Asp Lys Gly
            100                 105                 110

Ile Met Ala Asp Pro Thr Val Asn Val Pro Arg Leu Gly Thr Val Pro
            115                 120                 125

His Lys Ala Ser Val Val Gln Val Gly Phe Pro Cys Leu Gly Lys Gln
        130                 135                 140

Asp Gly Val Ala Ala Phe Glu Val Asn Val Ile Val Met Asn Ser Glu
145                 150                 155                 160

Gly Asn Pro Ile Leu Arg Thr Pro Gln Asn Ala Ile Phe Phe Lys Thr
                165                 170                 175

Cys Gln Gln Ala Glu Cys Pro Gly Gly Cys Arg Asn Gly Phe Cys
            180                 185                 190        Cys

Asn Glu Arg Arg Val Cys Glu Cys Pro Asp Gly Phe Tyr Gly Pro His
            195                 200                 205

Cys Glu Lys Ala Leu Cys Ile Pro Arg Cys Met Asn Gly Gly Leu Cys
            210                 215                 220

Val Thr Pro Gly Phe Cys Ile Cys Pro Pro Gly Phe Tyr Gly Val Asn
225                 230                 235                 240

Cys Asp Lys Ala Asn Cys Ser Ala Thr Cys Phe Asn Gly Gly Thr Cys
                245                 250                 255

Phe Tyr Pro Gly Lys Cys Ile Cys Pro Pro Gly Leu Glu Gly Glu Gln
            260                 265                 270

Cys Glu Leu Ser Lys Cys Pro Gln Pro Cys Arg Asn Gly Gly Lys Cys
            275                 280                 285

Ile Gly Lys Ser Lys Cys Lys Cys Pro Lys Gly Tyr Gln Gly Asp Leu
        290                 295                 300

Cys Ser Lys Pro Val Cys Glu Pro Gly Cys Gly Ala His Gly Thr Cys
305                 310                 315                 320

His Glu Pro Asn Lys Cys Gln Cys Arg Glu Gly Trp His Gly Arg His
                325                 330                 335

Cys Asn Lys Arg Tyr Gly Ala Ser Leu Met His Ala Pro Arg Pro Ala
            340                 345                 350

Gly Ala Gly Leu Glu Arg His Thr Pro Ser Leu Lys Lys Ala Glu Gly
            355                 360                 365

Arg Arg Asp Pro Pro Glu Ser Asn Tyr Ile Trp
            370                 375

<210> SEQ ID NO 24
<211> LENGTH: 374
<212> TYPE: PRT
<213> ORGANISM: Xenopus sp.

<400> SEQUENCE: 24

Met Ser Leu Thr Gly Tyr Phe Ala Ala Pro Leu Cys Ser Ile Phe Leu
1               5                   10                  15

Phe Ile Leu Ala His Ala Asp Ala Gly Gln Gln Glu Asp Ser Leu Tyr
            20                  25                  30

Met Trp Ile Asp Ala His Gln Ala Arg Val Leu Ile Gly Phe Glu Glu
        35                  40                  45

Asp Ile Leu Ile Val Ala Glu Gly Lys Met Ala Pro Phe Thr His Asp
    50                  55                  60

Phe Arg Lys Ala Gln Gln Arg Met Pro Ala Ile Pro Val Asn Ile His
65                  70                  75                  80
```

```
Ala Met Asn Phe Thr Trp Gln Ala Thr Gly Gln Ala Glu Tyr Phe Tyr
                85                  90                  95

Glu Phe Leu Ser Leu Arg Ser Leu Asp Lys Gly Ile Met Ala Asp Pro
            100                 105                 110

Thr Val Asn Met Pro Leu Leu Gly Thr Val Pro His Lys Ala Thr Val
        115                 120                 125

Ile Gln Val Gly Phe Pro Cys Leu Gly Asn Gln Asp Gly Val Ala Ala
    130                 135                 140

Phe Glu Val Asn Val Ile Val Met Asn Ser Glu Gly Asn Val Ile Leu
145                 150                 155                 160

Gln Thr Pro Gln Asn Ala Ile Phe Phe Lys Thr Cys Gln Gln Ala Lys
                165                 170                 175

Cys Thr Gly Gly Cys Arg Asn Gly Gly Phe Cys Asn Asp Arg His Val
            180                 185                 190

Cys Glu Cys Pro Asp Gly Phe Tyr Gly Pro His Cys Glu Lys Ala Leu
        195                 200                 205

Cys Met Pro Arg Cys Met Asn Gly Gly Leu Cys Val Thr Pro Gly Leu
    210                 215                 220

Cys Ile Cys Pro Pro Gly Tyr Tyr Gly Ile Asn Cys Asp Lys Val Asn
225                 230                 235                 240

Cys Thr Thr His Cys Leu Asn Gly Gly Thr Cys Phe Tyr Pro Gly Lys
                245                 250                 255

Cys Ile Cys Pro Ser Gly Tyr Glu Gly Glu Gln Cys Glu Thr Ser Lys
            260                 265                 270

Cys Gln Gln Pro Cys Arg Asn Gly Gly Lys Cys Ser Gly Lys Asn Lys
        275                 280                 285

Cys Lys Cys Ser Lys Gly Tyr Gln Gly Asp Leu Cys Ser Lys Pro Val
    290                 295                 300

Cys Glu Pro Ser Cys Gly Ala His Gly Thr Cys Ile Glu Pro Asn Lys
305                 310                 315                 320

Cys Gln Cys Lys Glu Gly Trp Asn Gly Arg Tyr Cys Asn Lys Lys Tyr
                325                 330                 335

Gly Ser Asn Leu Met Asn Ala Leu Arg Pro Thr Gly Ser Arg Asn Arg
            340                 345                 350

Gln His Thr Pro Ser Pro Lys Arg Thr Glu Asp Arg Gln Ala Leu Pro
        355                 360                 365

Glu Ser Asn Tyr Ile Trp
    370

<210> SEQ ID NO 25
<211> LENGTH: 378
<212> TYPE: PRT
<213> ORGANISM: Danio rerio

<400> SEQUENCE: 25

Met Ala Phe Arg Thr Pro Ala Val Gln Leu His Leu Lys Ala Cys Val
1               5                   10                  15

Leu Leu Leu Leu Gly Gly Leu Leu Glu Ala Ala Tyr Gln Glu Arg Gly
            20                  25                  30

Thr Met Tyr Met Trp Ile Asp Ala Asn Gln Ala Arg Ile Leu Ile Gly
        35                  40                  45

Phe Glu Glu Asp Ile Leu Ile Val Ser Glu Gly Lys Met Ala Pro Phe
    50                  55                  60

Thr His Asp Phe Arg Lys Ala Gln Gln Arg Met Pro Ala Ile Pro Val
65                  70                  75                  80
```

```
Asn Ile His His Val Asn Phe Thr Trp Gln Ala Thr Asp Gln Ala Glu
                85                  90                  95

Tyr Phe Tyr Glu Phe Gln Thr Leu Arg Ser Leu Asp Lys Asp Ile Met
           100                 105                 110

Asp Asp Pro Thr Val Asn Val Pro Leu Leu Gly Ser Val Pro His Lys
       115                 120                 125

Ala Ser Val Val Gln Val Gly Phe Pro Cys Arg Gly Asp Gln Asp Gly
   130                 135                 140

Val Ala Ala Phe Glu Val Thr Ile Leu Val Met Asp Ala Gly Gly Asn
145                 150                 155                 160

Ile Ile Leu Arg Thr Pro His Asn Ala Ile Phe Phe Lys Thr Cys Gln
               165                 170                 175

Arg Ala Lys Cys Pro Gly Gly Cys Arg Asn Gly Gly Tyr Cys Asn Glu
           180                 185                 190

Arg Gln Val Cys Glu Cys Gln Asp Gly Phe Tyr Gly Val His Cys Glu
       195                 200                 205

Lys Ala Leu Cys Ser Pro Arg Cys Leu Asn Gly Gly Leu Cys Met Ser
   210                 215                 220

Pro Gly Val Cys Ile Cys Pro Pro Gly Tyr Phe Gly Ser Ser Cys Glu
225                 230                 235                 240

Arg Ala Asn Cys Ser Thr Thr Cys Leu Asn Gly Gly Thr Cys Phe His
               245                 250                 255

Pro Gly Lys Cys Ile Cys Ala Val Ser Phe Glu Gly Val Arg Cys Glu
           260                 265                 270

Leu Ser Lys Cys Arg Gln Pro Cys Arg Asn Gly Gly Lys Cys Thr Gly
       275                 280                 285

Arg Asn Lys Cys Lys Cys Ser Lys Gly Tyr His Gly Asp Leu Cys Ser
   290                 295                 300

Lys Ala Val Cys Glu Pro Ser Cys Gly Ala His Gly Thr Cys Val Glu
305                 310                 315                 320

Pro Asn Arg Cys Gln Cys Arg Glu Gly Trp His Gly Arg His Cys Asn
               325                 330                 335

Lys Arg Phe Arg Gly Gly Val Ser Asn Ser Gln Arg Val Ser Pro Ser
           340                 345                 350

Lys His Lys Ser Pro Ser Val Ala Ala Lys Glu Ala Pro Glu Thr
       355                 360                 365

Ser Gln Pro Ser Glu Thr Asn Tyr Val Val
   370                 375

<210> SEQ ID NO 26
<211> LENGTH: 180
<212> TYPE: PRT
<213> ORGANISM: Homo sapiens

<400> SEQUENCE: 26

Met Ala Arg Arg Ser Ala Phe Pro Ala Ala Ala Leu Trp Leu Trp Ser
1               5                   10                  15

Ile Leu Leu Cys Leu Leu Ala Leu Arg Ala Glu Ala Gly Pro Pro Gln
               20                  25                  30

Glu Glu Ser Leu Tyr Leu Trp Ile Asp Ala His Gln Ala Arg Val Leu
           35                  40                  45

Ile Gly Phe Glu Glu Asp Ile Leu Ile Val Ser Glu Gly Lys Met Ala
       50                  55                  60

Pro Phe Thr His Asp Phe Arg Lys Ala Gln Gln Arg Met Pro Ala Ile
```

```
                65                  70                  75                  80
Pro Val Asn Ile His Ser Met Asn Phe Thr Trp Gln Ala Ala Gly Gln
                    85                  90                  95

Ala Glu Tyr Phe Tyr Glu Phe Leu Ser Leu Arg Ser Leu Asp Lys Gly
                100                 105                 110

Ile Met Ala Asp Pro Thr Val Asn Val Pro Leu Leu Gly Thr Val Pro
                115                 120                 125

His Lys Ala Ser Val Val Gln Val Gly Phe Pro Cys Leu Gly Lys Gln
            130                 135                 140

Asp Gly Val Ala Ala Phe Glu Val Asp Val Ile Val Met Asn Ser Glu
145                 150                 155                 160

Gly Asn Thr Ile Leu Gln Thr Pro Gln Asn Ala Ile Phe Phe Lys Thr
                165                 170                 175

Cys Leu Gln Ala
            180

<210> SEQ ID NO 27
<211> LENGTH: 152
<212> TYPE: PRT
<213> ORGANISM: Homo sapiens

<400> SEQUENCE: 27

Gly Pro Pro Gln Glu Glu Ser Leu Tyr Leu Trp Ile Asp Ala His Gln
1               5                   10                  15

Ala Arg Val Leu Ile Gly Phe Glu Glu Asp Ile Leu Ile Val Ser Glu
                20                  25                  30

Gly Lys Met Ala Pro Phe Thr His Asp Phe Arg Lys Ala Gln Gln Arg
            35                  40                  45

Met Pro Ala Ile Pro Val Asn Ile His Ser Met Asn Phe Thr Trp Gln
    50                  55                  60

Ala Ala Gly Gln Ala Glu Tyr Phe Tyr Glu Phe Leu Ser Leu Arg Ser
65                  70                  75                  80

Leu Asp Lys Gly Ile Met Ala Asp Pro Thr Val Asn Val Pro Leu Leu
                85                  90                  95

Gly Thr Val Pro His Lys Ala Ser Val Val Gln Val Gly Phe Pro Cys
                100                 105                 110

Leu Gly Lys Gln Asp Gly Val Ala Ala Phe Glu Val Asp Val Ile Val
            115                 120                 125

Met Asn Ser Glu Gly Asn Thr Ile Leu Gln Thr Pro Gln Asn Ala Ile
    130                 135                 140

Phe Phe Lys Thr Cys Leu Gln Ala
145                 150

<210> SEQ ID NO 28
<211> LENGTH: 176
<212> TYPE: PRT
<213> ORGANISM: Homo sapiens

<400> SEQUENCE: 28

Met Ala Arg Arg Ser Ala Phe Pro Ala Ala Ala Leu Trp Leu Trp Ser
1               5                   10                  15

Ile Leu Leu Cys Leu Leu Ala Leu Arg Ala Glu Ala Gly Pro Pro Gln
                20                  25                  30

Glu Glu Ser Leu Tyr Leu Trp Ile Asp Ala His Gln Ala Arg Val Leu
            35                  40                  45

Ile Gly Phe Glu Glu Asp Ile Leu Ile Val Ser Glu Gly Lys Met Ala
```

-continued

```
            50                  55                  60
Pro Phe Thr His Asp Phe Arg Lys Ala Gln Gln Arg Met Pro Ala Ile
65                  70                  75                  80

Pro Val Asn Ile His Ser Met Asn Phe Thr Trp Gln Ala Ala Gly Gln
                85                  90                  95

Ala Glu Tyr Phe Tyr Glu Phe Leu Ser Leu Arg Ser Leu Asp Lys Gly
            100                 105                 110

Ile Met Ala Asp Pro Thr Val Asn Val Pro Leu Leu Gly Thr Val Pro
            115                 120                 125

His Lys Ala Ser Val Val Gln Val Gly Phe Pro Cys Leu Gly Lys Gln
        130                 135                 140

Asp Gly Val Ala Ala Phe Glu Val Asp Val Ile Val Met Asn Ser Glu
145                 150                 155                 160

Gly Asn Thr Ile Leu Gln Thr Pro Gln Asn Ala Ile Phe Phe Lys Thr
                165                 170                 175

<210> SEQ ID NO 29
<211> LENGTH: 148
<212> TYPE: PRT
<213> ORGANISM: Homo sapiens

<400> SEQUENCE: 29

Gly Pro Pro Gln Glu Glu Ser Leu Tyr Leu Trp Ile Asp Ala His Gln
1               5                   10                  15

Ala Arg Val Leu Ile Gly Phe Glu Glu Asp Ile Leu Ile Val Ser Glu
            20                  25                  30

Gly Lys Met Ala Pro Phe Thr His Asp Phe Arg Lys Ala Gln Gln Arg
        35                  40                  45

Met Pro Ala Ile Pro Val Asn Ile His Ser Met Asn Phe Thr Trp Gln
    50                  55                  60

Ala Ala Gly Gln Ala Glu Tyr Phe Tyr Glu Phe Leu Ser Leu Arg Ser
65                  70                  75                  80

Leu Asp Lys Gly Ile Met Ala Asp Pro Thr Val Asn Val Pro Leu Leu
                85                  90                  95

Gly Thr Val Pro His Lys Ala Ser Val Val Gln Val Gly Phe Pro Cys
            100                 105                 110

Leu Gly Lys Gln Asp Gly Val Ala Ala Phe Glu Val Asp Val Ile Val
        115                 120                 125

Met Asn Ser Glu Gly Asn Thr Ile Leu Gln Thr Pro Gln Asn Ala Ile
    130                 135                 140

Phe Phe Lys Thr
145

<210> SEQ ID NO 30
<211> LENGTH: 335
<212> TYPE: PRT
<213> ORGANISM: Homo sapiens

<400> SEQUENCE: 30

Gly Pro Pro Gln Glu Glu Ser Leu Tyr Leu Trp Ile Asp Ala His Gln
1               5                   10                  15

Ala Arg Val Leu Ile Gly Phe Glu Glu Asp Ile Leu Ile Val Ser Glu
            20                  25                  30

Gly Lys Met Ala Pro Phe Thr His Asp Phe Arg Lys Ala Gln Gln Arg
        35                  40                  45

Met Pro Ala Ile Pro Val Asn Ile His Ser Met Asn Phe Thr Trp Gln
```

-continued

```
              50                  55                  60
Ala Ala Gly Gln Ala Glu Tyr Phe Tyr Glu Phe Leu Ser Leu Arg Ser
65                  70                  75                  80

Leu Asp Lys Gly Ile Met Ala Asp Pro Thr Val Asn Val Pro Leu Leu
                85                  90                  95

Gly Thr Val Pro His Lys Ala Ser Val Val Gln Val Gly Phe Pro Cys
                100                 105                 110

Leu Gly Lys Gln Asp Gly Val Ala Ala Phe Glu Val Asp Val Ile Val
            115                 120                 125

Met Asn Ser Glu Gly Asn Thr Ile Leu Gln Thr Pro Gln Asn Ala Ile
            130                 135                 140

Phe Phe Lys Thr Cys Leu Gln Ala Glu Cys Pro Gly Gly Cys Arg Asn
145                 150                 155                 160

Gly Gly Phe Cys Asn Glu Arg Arg Ile Cys Glu Cys Pro Asp Gly Phe
                165                 170                 175

His Gly Pro His Cys Glu Lys Ala Leu Cys Thr Pro Arg Cys Met Asn
                180                 185                 190

Gly Gly Leu Cys Val Thr Pro Gly Phe Cys Ile Cys Pro Pro Gly Phe
            195                 200                 205

Tyr Gly Val Asn Cys Asp Lys Ala Asn Cys Ser Thr Thr Cys Phe Asn
    210                 215                 220

Gly Gly Thr Cys Phe Tyr Pro Gly Lys Cys Ile Cys Pro Pro Gly Leu
225                 230                 235                 240

Glu Gly Glu Gln Cys Glu Ile Ser Lys Cys Pro Gln Pro Cys Arg Asn
                245                 250                 255

Gly Gly Lys Cys Ile Gly Lys Ser Lys Cys Lys Cys Ser Lys Gly Tyr
                260                 265                 270

Gln Gly Asp Leu Cys Ser Lys Pro Val Cys Glu Pro Gly Cys Gly Ala
            275                 280                 285

His Gly Thr Cys His Glu Pro Asn Lys Cys Gln Cys Gln Glu Gly Trp
    290                 295                 300

His Gly Pro Ala Gly Ala Gln Leu Arg Gln His Thr Pro Ser Leu Lys
305                 310                 315                 320

Lys Ala Glu Glu Arg Arg Asp Pro Pro Glu Ser Asn Tyr Ile Trp
                325                 330                 335
```